(12) United States Patent
Liu et al.

(10) Patent No.: US 6,686,450 B1
(45) Date of Patent: Feb. 3, 2004

(54) IMMUNOSUPPRESSIVE AGENTS THAT INHIBIT CALCINEURIN FUNCTION AND USES OF THESE AGENTS

(75) Inventors: Jun O. Liu, Cambridge, MA (US); Luo Sun, Watertown, MA (US); Hong-Duk Youn, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/335,011

(22) Filed: Jun. 17, 1999

Related U.S. Application Data

(60) Provisional application No. 60/089,786, filed on Jun. 18, 1998.

(51) Int. Cl.[7] ............................................. A61K 38/16
(52) U.S. Cl. ........................................ 530/352; 530/350
(58) Field of Search ................................. 530/350, 352

(56) References Cited

FOREIGN PATENT DOCUMENTS

WO     WO 88/06630     3/1998

OTHER PUBLICATIONS

Baughman et al, FKBP51, a novel T–cell–specific immunophilin capable of cacineurin inhibition, Aug. 1995, Molecular & Cellular Biology 15(8): 4395–4402.*
Nagase et al, Prediction of the coding sequence of unidentified human genes VII. The complete sequences of 100 new cDNA clones from brain which can code for large proteins in vitro. Apr. 1997, DNA Res 4(2): 141–150.*
Ngo et al., in The Protein Folding Problem and Tertiary Structure Prediction, 1994, Marz, et al., (ed.), Birkhauser, Boston, MA, pp. 433 and 492–495).*
Sambrook et al., in Molecular Cloning, 1989, Cold Spring Harbor Laboratory, CSH, NY, Ch. 17.*
Henderson et al., Therapeutic Modulation of Cytokines, 1995, Annals of Rheumatic Disease 54: 519–523.*
U.S. patent application Ser. No. 60/089,786, Liu et al., filed Jun. 18, 1998.
U.S. patent application Ser. No. 09/420,638, Liu et al., filed Oct. 21, 1999.
Bierer, et al., "Two Distinct Signal Transmission Pathways in T Lymphocytes are Inhibited by Complexes Formed Between an Immunophilin and Either FK506 or Rapamycin" *Proc Natl. Acad Sci. USA*, 87: 9231–9235, 1990.
Cardenas, et al., "Immunophilins Interact Calcineurin in the Absence of Exogenous Immunosuppressive Ligands" *EMBO J* .13: 5944–5957, 1994.
Hsu, et al., "Formation of *in vivo* Complexes Between the TAL1 and E2A Polypeptides of Leukemic T Cells", *Proc. Natl. Acid Sci USA*. 91: 3181–3185, 1994.
Jiang et al., "Distinct Tissue and Cellular Distribution of Two Major Isoforms of Calcineurin", *Mol. Immunol.* 34: 663–669, 1997.
Kino, et al., FK–506, A Novel Immunosuppresant Isolated From a Streptomyces I. Fermentation, Isolation, and Physico–Chemical and Biological Characteristics, *J. Antibiotics*, 40: 1249–1255, 1987.
Lai, et al., "Cain, A Novel Physiological Protein Inhibitor of Calcinuerin", *The Journal of Biological Chemistry*, 273(29): 18325–18331, 1998.
Liu, et al., "Calcineurin Is A Common Target of Cyclophilin–Cyclosporin A and FKBP–FK506 Complexes," *Cell.* 66: 807–815, 1991.
Sehgal, et al., "Rapamycin (AY–22,989), A New Antifungal Antibiotic, II. Fermentation, Isolation and Characterization", *J. Antibiol.*, 28: 727–724, 1975.
Toullec, et al., "The Bisindolylmaleimide GF 109203X is a Potent and Selective Inhibitor of Protein Kinase C" *J. Biol. Chem.* 266: 15771–15781, 1991.
Youn, et al., "Apoptosis of T Cells Mediated by $Ca^{2+}$—Induced Release of the Transcription Factor MEF2", *Science*, 286: 790–793, 1999.

* cited by examiner

*Primary Examiner*—Christina Chan
*Assistant Examiner*—Phuong N Huynh
(74) *Attorney, Agent, or Firm*—Choate, Hall & Stewart

(57) ABSTRACT

The present invention provides novel immunosuppressive agents. In particular, the invention provides immunosuppressive agents that bind calcineurin and/or that inhibit interaction between calcineurin and NF-AT. The invention also provides analogs of these agents, nucleic acids encoding the agents and/or their analogs, gene therapy vectors, etc., and methods of making and using them.

9 Claims, 40 Drawing Sheets

FIG.1D

| Cabin # | DNA INSERT | Size (aa) |
|---------|------------|-----------|
| 1-154   |            | 184       |
| 1-6     |            | 166       |
| 1-97    |            | 96        |
| 1-14    |            | 77        |

FIG.2A-1

```
MIRIAALNASSTIEDDHEGSFKSHKTQTKEAQEAEAFALYHKALDLQKHDRFEESAKAYH   60
ELLEASLLREAVSSGDEKEGLKHPGLILKYSTYKNLAQLAAQREDLETAMEFYLEAVMLD  120
STDVNLWYKIGHVALRLIRIPLARHAFEEGLRCNPDHWPCLDNLITVLYTLSDYTTCLYF  180
ICKALEKDCRYSKGLVLKEKIFEEQPCLRKDSLRMFLKCDMSIHDVSVSAAETQAIVDEA  240
LGLRKRQALIVREKEPDLKLVQPIPFFTWKCLGESLLAMYNHLTTCEPPRPSLGKRIDL   300
SDYQDPSQPLESSMVVTPVNIQPSTVSTNPAVAVAEPVVSYTSVATTSFPLHSPGLLET   360
GAPVGDISGGDKSKKGVKRKKISEESGETAKRRSARVRNTKCKKEEKVDFQELLMKFLPS  420
RLRKLDPEEEDDSFNNYEVQSEAKLESEPSIGPQRLSFDSATFMESEKQDVHEFLLENLT  480
NGGILELMMRYLKAMGHKFLVRWPPGLAEVVLSVYHSWRRHSTSLPNPLLRDCSNKHIKD  540
MMLMSLSCMELQLDQWLLTKGRSSAVSPRNCPAGMVNGRFGPDFPGTHCLGDLLQLSFAS  600
SQRDLFEDGWLEFVVRVYWLKARFLALQGDMEQALENYDICTEMLQSSTAIQVEAGAERR  660
DIVIRLPNLHNDSVVSLEEIDKNLKSLERCQSLEEIQRLYEAGDYKAVHLLRPTLCTSG   720
FDRAKHLEFMTSIPERPAQLLLLQDSLLRLKDYRQCFECSDVALNEAVQQMVNSGEAAAK  780
EEWVATVTQLLMGIEQALSADSSGSILKVSSTTGLVRLTNNLIQVIDCSMAVQEEAKEP   840
HVSSVLPWIILHRIIWQEEDTFHSLCHQQQLQNPAEEGMSETPMLPSSLMLLNTAHEYLG  900
```

```
RRSWCCNSDGALLRFYVRVLQKELAASTSEDTHPYKEELETALEQCFYCLYSFPSKKSKA  960
RYLEEHSAQQVDLIWEDALFMFEYFKPKTLPEFDSYKTSTVSADLANLLKRIATIVPRTE  1020
RPALSLDKVSAYIEGTSTEVPCLPEGADPSPPVVNELYLLADYHFKNKEQSKAIKFYMH   1080
DICICPNRFDSWAGMALARASRIQDKLNSNELKSDGPIWKHATPVLNCFRRALEIDSSNL  1140
SLWIEYGTMSYALHSFASRQLKQWRGELPPELVQQMEGRRDSMLETAKHCFTSAARCEGD  1200
GDEEEWLIHYMLGKVAEKQQQPPTVYLLHYRQAGHYLHEEAARYPKKIHYHNPPELAMEA  1260
LEVYFRLHASILKLLGKPDSGVGAEVLVNFMKEAAEGPFARGEEKNTPKASEKEKACLVD  1320
EDSHSSAGTLPGPGASLPSSSGPGLISPPYTATPIDHDYVKCKKPHQQATPDDRSQDSTA  1380
VALSDSSSTQDFFNEPTSLLEGSRKSYTEKRLPILSSQAGATGKDLQGATEERGKNEESL  1440
ESTEGFRAAEQGVQKPAAETPASACIPGKPSASTPTLWDGKKRGDLPGEPVAFPQGLPAG  1500
AEEQRQFLTEQCIASFRLCLSRFPQHYKSLYRLAFLYTYSKTHRNLQWARDVLLGSSIPW  1560
QQLQHMPAQGLFCERNKTNFFNGIWRIPVDEIDRPGSFAWHMNRSIVLLKVLAQLRDHS   1620
TLLKVSSMLQRTPDQGKKYLRDADRQVLAQRAFILTVKVLEDTLSELAEGSERPGPKVCG  1680
LPGARMTTDVSHKASPEDGQEGLPQPKKPPLADGSGPGPEPGGKVGLLNHRPVAMDAGDS  1740
ADQSGERKDKESPRAGPTEPMDTSEATVCHSDLERTPPLLPGRPARDRGPESRPTELSLE  1800
```

FIG. 2A-3

FROM Fig.2A-2

```
ELSISARQQPTPLTPAQPAPAPAPATTTGTRAGGHPEEPLS RLSRKRK LLEDTESGKTLL   1860
LDAYRVWQQGQKGVAYDLGRVERIMSETYMLIKQVDEEAALEQAVKFCQVHLGAAAQRQA    1920
SGDTPTTPKHPKDSRENFFPVTVVPTAPDPVPADSVQRPSDAHTKPRPALAAATTIITCP    1980
                                                        ↑
                                                       154
PSASASTLDQSKDPGPPRHRPEATPSMASLGPEGEELARVAEGTSFPPQEPRHSPQVKM     2040

APTSSPAEPHCWPAEAALGTGAEPTCSQEGKLRPEPRRDGEAQEAASETQPLSSPPTAAS    2100
                                                 ↑
                                                14
SKAPSSGSAQPPEGHPGKPEPSRAKS RPLPNMP KLVIPSAATKFPPEITVTPPTPLLSP    2160
                     ↑
                    97
KGSISEETKQKLKSAILSAQSAANVRKESLCQPALEVLETSSQESSLESETDEDDDYMDI    2220
```
                            ↑
                            6

| | | | | | |
|---|---|---|---|---|---|
| + | + | − | + | + | + | Ionomycin
| + | + | + | + | − | + | PMA
| + | − | + | + | + | − | pSG–HACN
| − | + | + | + | + | + | pSG–Cabin 1–14

Cabin 1 cDNA Sequence (full length)

tagccggacgcgcggtggtcgggacagactggccgttgctgtgggagacgcctggagagttgtggactggggcaacctttt
gccagtgatgagaagtgatgctcgtggcagtgctgcagctctctgaatctctgaatatgattgcagcttaaatgccagctc
caccattgagagtgatcatgaaggaagcttaaaagtcacaaaaccagacaaggaggctcaggaagcagaggcttttg
cattgtaccacaaggccctgatctgcagaaacatgaccggtttgaggagtctgccaaagcctaccatgacctcttggag
gcgagcctgctgcggggaggcagtttcatccgtgatgagaagaggggttgaaacaccctgggctgatactgaaatattc
cacttataagaacttgcccagctggcagcccagcggaggatctggagacagccatggagttctacttagaggcagtga
tgctggactccacagatgtcaacctctgtataagattgacatgacatgtgccctcatccggatccccctggctcgc
catgctttgaggaagggctgcggtgcgtgtactcgtcatcatctgcaaagcttggaagaagattgccggtacagcaagg ctcctca
cagtgattacacaacatgtctgtactcatctgcaaagcttggaagaagattgccggtacagcaagg ctcctca
aggagaagatttttgaggagaccagcctgtctccggaaggactctctcagaatgttcctcaaatgtgacatgtcgatcac
gatgttcggtgagtgagtcagctgagacacaggcgattgtagatgaggccttgggggctgcgaaaaagaaagcgctgat
tgtgcgggaggaggccggaccctgaaacttgtgcagcccattcctttcttcacctggaagtgcctcggagagagcttgc
tggccatgtacaatcatctccaccgtgagcccacgtccagccagtccaaaaggattgatttgtcggactaccag
gaccccagccagcctcttgagtctccatggtgtgacgccagttaacgtgacgccagcactgtcagccacaacc
agctgtggctgtcgcgagcctgtgggtgtcctacacctctgtggctacaccagcttccacctgcacagtcctggtctgt
tggagacaggcgcctgtggtgggtgatatttctggggagtaaatccaaagaagggtaaacgaagaagatttcagaa
gagagtggagaacagcaaagcgggtccgtgtccgaaacaccaagtgcaaaaaagagaaagaagtagacttcca To Fig. 7B

FIG. 7B

FROM FIG. 7A ggagcttctgatgaagttcttgccgtccaggttaagaaagctggacctgaggaggagatgattccttaataactatg
aagtccagtcagaagccaaactggaaagcttccaagcattgggcctcaaaggctgtcatttgactcagccacattcatg
gaatctgaaaagcaggacgtgctgagttcctgctgggaaccaccacgggggcatcctggagctgatgatgcta
cctgaaaagccatgggccacaagttcttggtaagtggcctccagctggccggagtcgtctcagcgtctaccacagct
gggaggcacagccagcctgcccaaccgctgctgaggactgcagcaacaagcacatcaaggacatgatgctgatg
tctctctcctgcatgaactccagctggaccgtgctgaccagtggctgtgaccagagctctgcagtgtctcctcggaactg
ccctgctggtatgtgtggcagattggacctgacttccagggacccactgcctggtgaccctctacagctgtcat
ttgcctcgtcccagcgcgacctgttcgagatggcagttggctggaagtttgtgtgtccgtgtttactgctgaaggctcgcttc
ctggcgctgcaggagacatggagcgagcagggaaggacctggagaatctgacatctgcacagaaatgctccaccgcat
ccaggtgggggctgaacgagaaccgaagtcgctggagctgccagtgccagtccctggaggagatgtcagcggctgtgaagcaggac
agagattgataagaccgaagtcgatctgctccgcccactgcttcttctgcagcagatgtccagcagatggtgaacctggagttatgac
tacaaggctgttgtgcatctgctccgccagtgctggggttcctcttctgcgagcttgaccgcttgcctccggctgaggactatcggagttttg
ttccattcctgagagtggctctgaacgaggctgtccagagatggtgaactcaggtgaggctgaggctgccgccaaggaggggtgggtg
agtgttccgatgtgctctgaacgaggctgtccagagatggtgaactcaggtgaggctgaggctgccgccaaggaggggtgggtg
gccacagtgaccaactgctgatgggcatcgagagcaggagcccctctgcgacagcagtggtagcatcctgaagtatcatc To Fig. 7C

FIG. 7C

FROM FIG. 7B ctccaccactggccttgtgcggctcaccaacaacctcatccagtcattgactgcagcatggctgctgtgcaggaggagcca
aggagcccacgtctcttcagtgctaccctggatcattctacacgcggatcatctggcaggagaagacacttccattct
ctgtgccaccagcagctccaaaaccagcggagaggatgtcagagacgccatgctccatcctccctcatgct
gctgaacacagcccacgtatttgggcagaaggtcctggtgctgcaattcagtggggctctgctgcgattctatgtgc
gagtactccagaaggaactggctgcatccacctctgaagacacgcaccctacaaggagagctggagacagcttggag
cagtgcttctactgctgtacagcttccccagcaagaagagtaaggcaggtaaggtacctggaggacactcggcccagcagt
ggatcttatatggggaggatgcactgttcatgtttggagtatttaagccaagaccctcctgaatttgacagctataaga
ccagcacgtgtctgctgacttggccaacctactgaagagaattgccaccattgtgcctcgcagagaggccagcctt
agcctggacaaagtctctgcctactggagggaactcaactgaggctctgattatcattcaaaaacaaggagcgtcaaggccatcaagttct
tccagtggtgaacgagctttactactctgcccaataggtttgattcctgggcagcatggctctggccggccagccgcattcag
acatgcatgacatctgcatctgaagctgaagctgaactccaatgagctgaagatgggaagcatgcatgccacgccgtcttgaactgcttccgtcg
gacaagctgaactccaatgagctgaagctgaagctgaactccaatggcccattggaagcatgaacatgccaccatgtcctatgccttgcactcattcgcct
ggcctggagattgacagctccaacttgacagctccaacctgtgccccctgccctgtgcagcagatggagggccgacagcatgcta
cacgtcaattgaagcagtggaggcgagctgcagcagcgtgatggtgacgagggtgtggacgaggagcgcgacagcatcatccactacat
gagacagccaagcactgtttcacatcagcagcagcagcagcagccgctgcgagggtttacttgctcactacaggcagctgccactacctgc
gctgggcaagtggctgagaaggtgctgcgagcagcagcagccaccgcgtttacttgctcactacaggcagctgccactacctgc
acgagaggctgccgctacccgagaagagatccactaccaaccacccctgagctggaggtgtgccatggagggtgtac To Fig. 7D

FIG. 7D

FROM FIG. 7C tttcggctccatgcttccatcctgaagctcctggggaagccgattctggggttggtgcagaggtcctgtgtcaactttat
gaaggagctgcagaaggaggacccttgccaggggagagaagaacacaccaagcttcagaaaggagaaggcctgcc
tggtggacgaggactccactcttcagctggtgggacactgccgggccgagcctccctcctcctctgccagt
ctgacatcccccacctt acacagccactccgat tgaccacgat tacgtcaaat gtaaaaaccccacagcaagaacgcc
ggacgaccgaagcaggacagcaggaccgtagcactctcagact cttcagccagacttcttt aat gagccacca
gcttactggaaggctccagaaatcctacacagagaagaggctgccat tctcagt tccaagcaggagacgggtaaa
gatcttcaggggggccacagaaggagaaaacgaggagtcattggagagtacagaaggcttccgggctgcagagca
aggtgtccagaagccgcagaaacctccagggagacctcctgccatccctgcaagcctcagcatccacccaccctgt
gggatgggaagaagaggggaacctccaggggagcccttcccccagggctgtgcctgagccgcttccccagcactataagagtctcta
cggcagttctcacagagcagtgcatcgcctcctgtgcctgagcgctgcccagcactataagagtctcta
ccgtctgccttcctctacacctacagcaagacccaccagggctcttctgcagaggaacaagaccattcttcaacgcatc
tcccgtggcaacaactgcagcacatgccggcacaggaccatgaacctcatgaccgtccatgtgctgctcaa
tggcggatcccgtggacgagat tgaccggccggcagct ttgcctggcacat gaacctcatgtgctgtcaa
ggtgctgcccagctgccggaccacacccctgctgaaggtgtcctccagcagccttcagcggaccaggcaaga To Fig. 7E

FIG. 7E

FROM FIG. 7D agtatctgcgagatgctgaccgccaggtcctggcgcagcgggccttcatcctcactgtgaagtgtcgaagacacgctg
agcgagctcgcagaggggtcagaacgcccaaggtctgtggcctcccggaccaggtgaccaccgatgtctc
acacaaggccagtcctgaggatgcaggaggcctcccagccgaagagcccctctggctgatggctcaggccag
ggcccgagccagggggcaaagtgggcctcctcaaccaccgcctgtggcatggatgcaggaacagtgcagaccaagc
gggggagcgggaaggataaagagagccacggccaggcccactggagccactgtttgccactc
agacttggagcgggacaccaccctgctgccagtgccccgcaaggacgggccccgagacgtgccactgagctgt
cctggagagctgagcatcagtgcccgagcagccagcccccgctcacccccgaggagcgcccagcccgcccccc
gccaccaccaggacaggcaggggccacggagagcgctcccggctcagccgtgtgtggcagcaggaagtcctgga
ggacacagagtcaggcaggacacttctgtttggatgcctacatgctcatcaagcagtggatgaggctgcgctggcagget
tgggccgtgtgtggagagatcattcctgggcttcttcctgtgacagttgtgccccagagacaggcctcgtgccagctccaaagcaccc
gtgaagttctgccaggagaacttcttcctgtgacagtggtgcccacagccgtcgggagcctcgtgccagctgactctgtccagc
caaagacgcgagagaacttctcacagaacagtcctgtgtgcccacagccgtcgggagcctcgtgccagctgactctgtccagc
ggcccagtgatgtctcacaccagctgccgccactagctgccgccactagctgccgccactatatcctcttcctccgtcagcatca
gcttccaccctggccagtccccggacccctcccggcacctgaagctaccccagctaccccccagcatggcctctct To Fig. 7F

FIG. 7F gggcccagagggagaagagctggcgagagtggcagagagggcaccagcttcccgcctcaggacgcacgtccgcagg
tgagatgccccacaagttccccgcagagagctgcctgtgccggcacagcgtgcctggcacagcgctgagccc
acctgccaggagggaaactgagccctgagccggagagggatggggaggctcaggagctgagctgagactcagcc
cctgagctctccccacagctgccagtccaagctcaaggcagtgggagtgccagcagagggtcaccaggca
agcctgagccagccggctaagtcccgcccctgcccaacatgccaaactggtcatccctccgccgccaccaagttc
ccccctgagatcacgtcacgccaccccaccccaacctgctctccccaaggcagatctcgaggagaccaagcagaa
gctgaagtcagccatcctttctgccagtcctgctgccaacgtgaggaggagagcctatgccagccagcctgggtcc
tggagacatccagcggagtctcgctggagacagagagagagcgacgactacatggacatttgaggggccact
gcagccccacgccaggagacccagcagcccccaggcctgaatgccccctgccagccacctcctcatgcatcctcctgtaccagtcag
cacatgatgccactcccacacagccccgcctgccaggcccacctttagccatgtgaagtgatggtcgcatctgcacg
gctgtccacacacatggagccagagagggggcccgcctagtgtgactttgactttgtaaatctgccacaccccagctgccatatccaccctcgacgcc
ccaggcggcatcctttctatgaagtgttgctttgacagtggaggggtcctttagggcaggtcacccctcaccctttttttggttgct
gggatgagccggctctgcctgtcacagtggaacagtt (SEQ ID NO:8)
tttctaataaagatggaacagtt

FROM FIG. 7E

Cabin 1cDNA coding sequence

```
caccattgaggatgatcatgaaggaagctttaaaagtcacaaaaccagacaaaggaggctcaggaagcagaggctttg
cattgtaccacaagccctgatctgcagaaacatgaccggtttgagggagtctgccaagcctaccatgagctcttggag
gcgagcctgctgcggggaggcagtttcatccggtgatgagaaagagggggttgaaacaccctggctgatactgaaatattc
cacttataagaacttggccagctgccagctggcagcagccagcagccatggagtctggagtcttctactagagcagtga
tgctggactccacagatgtcaacctctggtataagattggacatggcctgaggctcatccgatccccctgctcgc
catgctttgaggaaggctgcggtgcaatcctgaccactggcctgttttggataatcactgtcctgtacaccct
cagtgattacacacaacatgtctgtacttcatctgcaaagctttgaggaaggattgccgtacagcaaagggctggtcctca
aggagaagattttttgaggagcagcctgtctccggaagccttgagatgaggcctgtagatgaggccattcctcctcaaatgtgacatgtcgattcac
gatgttttcggtgagtgcagtgcagtgagacacaggcgattgtgcagccatggtgtgcagccccattccttccttctttcctttctcacctggagtgcctcggagagcgctgat
tgtgcgggagaaggagccggaccctgaaacttgtgcagccccaccactctgcccagccttccagctgtgggcgctgaaaaagaggcaagcgctgc
tggccatgtacaatcatctcaccacctgtgagccccacgtcccagcctggcaaaaggattgatttgtcggactaccag
```

FROM FIG. 8A gaccccagccagctcttggatcctccatggtggtgacgccagttaacgtgatccagcaagcactgtcagcaccaccc
agctggctgcgccgagctgtggtctcctacacctctgtggctacaaccagcttccactgcacagtcctggtctgt
tggagacaggcgctcctgtgggtgatattctggggagataatccaagaaagggtaaaacgaagaagattcagaa
gagagtggagaaacagcaaagcgcgtctgccgtccgaacaccaagtgcaaaaagaagagaaagtagacttcca
ggagcttctgatgaagttcttgccgtccaggttaagaaagctggaccctgaggaggaagatgattcctttaataactatg
aagtccagtcagaaacctgaaagcttccaaggcatggcctcaaaggctgtcattgactcagccacattcatg
gaatctgaaaagaggacgtgcatgagttcctgctgagaacctaaccaacaagccatcctggagctgatgatgcta
cctgaaagccatgggccacaagttctcttggtaaggtggcctccaggctcgtgctgtcgcaggacacatgotgatg
gggaggaggcacagcctgccaaaccgctgcctgagggactgctgagcagtggctgtgaccaaagccagagctctgcagtgtctcctcggaactg
tctctctcctgcatgaactccagctggacctgactgactttggacttccagagaccctgcgcagtcctacagctgtcat
cctgctggtatgtgaatgcagat tggccagtggttggctggattggtggtccgtgtttactggctgaaggctcgctc
ttgcctcgtcccagcgacctgttcgaggatggttggctggatggcccctggagaactatgacatctgcacagaaatgtccacagagttccaccgccat To Fig. 8C

FIG. 8C

FROM FIG. 8B ccagtggaggcagggctgaacgaagagacattgtcatccggctgccaacctccataatgactctgtggtttccctgg
agggattgataagaacctgaagtcgctggagcggtgccagtccctggaggagattcaggctgtgtatgaagcaggcgac
tacaaggctgttgtgcatctgctccgccccactttgtgccacagtgggtttgaccggccaaacacctggagtttatgac
ttccattcctgagagaggccagcccagctgctcttcttctgcgaggactatcgcagcagtgtttg
agtgttccgatgtggctctgaacgaggctgtcagcgagctgaactcaggtgaactcaggaggagtgggtg
gccacagtgaccactgctgatgggcgctcaccaacctcatccaggtcattgactgcagcatggctgtgcaggaggagcca
ctccaccactgcctttgtgcggctcaccaacctcatccaggtcattgactgcagcatggctgtgcaggaggagcca
aggagcccacgtctcttcagtgctacccctggatcattctacaccgatcatctggcagaggaagacaccttccattct
ctgtgccaccagcagctccaaaaccagtggagggagatgtcagagacgcccatgctcccatcctcccctgct
gctgaacacagccacagtatttgggcagagtcctggctgcaatcagatgggctctgctgcgattctatgtgc
gagtactccagaaggaactggctgcatccacctctgaagacacgcaccctacaagaggagctggagacactcggcccttggag
cagtgcttctactgcctgtacagcttcccccaagagaagtaccggaacactcggcccagccagt
ggatcttatatggggaggatgcactgttcatgtttgagtatttaagcccaagacccttcctgaatttgacagctataaga To Fig. 8D

FIG. 8D

```
ccagcaccgtgtctgctgacttggccaacctactgaagagaattgccaccattgtgcctcgcacagagaggcagccctt
agcctggacaagtctctgcctacattgagggaacttcaactgaggtaccctgcctcccagagggggctgaccctcccc
tccagtgtgaacgagcttttactacctcctggctgatcattcaaaaacaaggagcagtccaaggccatcaagttct
acatgcatgacatctgcatctgcccaataggttttgattcctggcaggcatggctctggcccggccagccgatcag
gacaagctgaactccaatgagctgaagagtgatggccatttggaagcatgaagccacgcccgtcttgaactgcttccgtcg
ggccctgggatttgacagctccaacttgtcctatggattgagtatgcaccatgtcctatgcttgcactcattgcct
cacgtcaattgaagcagtggagggagagctgagctgtgcagcagatgagggccgacagcatgcta
gagacagccaagcactgtttcacatcagcagcagcagccccaagaagatccataccaccaccacctgagctggccactacctgc
gctgggcaagtggctgagaagcagcagccgctaccccaagaagatccataccaccaccacctgagctggccactacctgc
acgaggaggctgcccgctaccccagaagatccataccaccaccacctgagctggccactacctgc
tttcggctccatgcttccatctcctgaagctcctggggaagcccgattctgggtggtgcagggtcctggtcaacttat
```

FROM FIG. 8C

```
gaaggagctgcagaggaccctttgccaggggcgaggagaggaacacaccaaagcttcagaaaaggagaggcctgcc
tgtggacgaggactcccactcttcagctggagacactgccggcctccctccctcctctctggccaggt
ctgacatcccacctacacagccactccgattgaccacgtaaaaacccacagcaggcaacgcc
ggacgccgaagcaggagcagcagccgtagcactctcagactctcaacgcaggacttctttaatgagccaca
gcttactggaaggctccaggaaatcctacacagagaagaggctgccattctcagttccaagcaggaggacgggtaaa
gatcttcaggggcacagaagaagaggaaaaacgaggagtcattggagagtacagaggcttccgggctgcagagca
agtgtccagaagcctgctgcagaacccagcctctgcttgcatccctgcaagcctcagcatccacacccctgt
gggatgggaagagaggggacctcccagggccttccccagggctgcgtgctgccggctggtgctgaggagcag
cggcagtttctcacagcagtgcatcgtgctacacctacagcaagaccacggaacctccagtgggccgcgacgtgttgctaggcagta
ccgtctgcctctacccctacacgaggcacacatgccgcacacagggctctctgcgagaggaacaagaccaattctcaacggatc
tcccgtggcaacactgcagcacaactgccgcacacacaaatgaaccgctcaatgaaccgcatc
tggcgggatccccgtggacgagattgaccggccagctttgcctggcctggcacatgaaccgctcaatgtgctgtgctcaa
```

FIG. 8F

```
ggtgctggccagctgcgggaccacagcaccctgctgaaggtgtcctccatgcttcagcgaccccagaccagggcaaga
agtatctgcgagatgctgaccgccagtcctgagcgcaggccttcatcctcactgtgaaggtgctgaagacacgctg
agcgagctcgagagggtcagaacgccaaggtctgtggcctcccgagccaggatgaccacgatgtctc
acacaaggccagtcctgaggatggccaggagggcctccccagccgaagaagccctctggctgatggctcagggccag
ggcccgagccaggaggcaaagtgggcctcctcaaccacccgctgtggccatggatgcagaagacagtgcagaccaaagc
gggagcggaaggataaagagagccaggccccatggacacgagtgaggccactgtttgccactc
agacttggagcggacaccccctgctgccaggtcgcccaaggagcccgagacgggcccagccagctgagctgt
ccctggaggctgagcatcagtgccggacacagccaccccgctcaccccagggagcgctcacccgaggagcttcctgga
gccaccacaggaccaggagcaggagggccaccagccagcccgtcatcaggcaggtgatgaggctgcctggagcaggct
ggacagagtcaggcaagacacttctgttggatgcctacgtgtccagagactacatgctcatcaagcaggtgatgacc
tgggccgtgtgtggagaggtcaggcatcatgtcgagactacatgctcatcaagcaggtgatgaggctgcctggagcaggct
gtgaagttctgccaggtccatctcggggctgccgccagagacaggcctcggggagacaggcctcggggagacacccc
```

FROM FIG. 8E

To Fig. 8G

FROM FIG. 8F

FIG. 8G caagagcagcgagagagaacttctttcctgtgacagtggtgccacagccctgaccctgtgcagctgactctgtccagc
ggccagtgatgctcacaccaagcctgccctgcactagctgcacctgccgccacaactattatcacctgccctcgtcagcatca
gcttccaccctggaccagtccaaggaccctgggcctcccgccacacaggcctgaagctaccccagcatgcctctct
gggcccagaggagaagagctggcgagagtggcagagggcaccagctcccgcctcaggagcagagctgcacaggcgctgagccc
tgaagatggccccacacaagtccccgcagccacactgctgccgcagaaggggatgggggctcaggggctgcgagtgagactcagcc
acctgcagccagggggaaactgaggcctgagcgcagagccccaggcccccaagcccagggggtcaccaggca
cctgagctctccccaacagctgccagtcccgcccagctgggagtgccagccaccagaggggtcaccaggca
agcctgagccagggctaagtccggccaagctggtcatccctccgccaccaagttc
cccctgagatcacgtcacgccaccccaccaaccctgctgccaacgtgaggaggagcagcatctcggaggcagcagcagaa
gctgaagtcagcatccttctgccagtctgctgccagtcctgctgagagcagcaggagccgagcctgaggtcc
tggagacatccagcaggagtcctcgctggagagcagcggagacgagcgagagcagcgacatttga (SEQ ID NO:15)

FIG. 9A

Cabin 1 Polypeptide Sequence (Full Length)

MIRIAALNASSTIEDDHEGSFKSHKTQTKEAQEAEEAFALYHKALDLQKHDRFEESAKAYH
ELLEASLLREAVSSGDEKEGLKHPGLILKYSTYKNLAQLAAQREDLETAMEFYLEAVMLD
STDVNLWYKIGHVALRLIRIPLARHAFEEGLRCNPDHWPCLDNLITVLYTLSDYTTCLYF
ICKALEKDCRYSKGLVLKEKIFEEQPCLRKDSLRMFLKCDMSIHDVSVSAAETQAIVDEA
LGLRKKRQALIVREKEPDLKLVQPIPFFTWKCLGESLLAMYNHLTTCEPPRPSLGKRIDL
SDYQDPSQPLESSMVVTPVNVIQPSTVSTVATTSFPLHSPGLLET
GAPVGDISGGDKSKKGVKRKKISEESGETAKRRSARVRNTKCKKEEKVDFQELLMKFLPS
RLRKLDPEEEDDSFNNYEVQSEAKLESFPSIGPQRLSFDSATFMESEKQDVHEFLLENLT
NGGILELMMRYLKAMGHKFLVRWPPGLAEVVLSVYHSWRRHSTSLPNPLLRDCSNKHIKD
MMLMSLSCMELQLDQWLLTKGRSSAVSPRNCPAGMVNGRFGPDFPGTHCLGDLLQLSFAS
SQRDLFEDGWLEFVVRVYWLKARFLALQGDMEQALENYDICTEMLQSSTAIQVEAGAERR
DIVIRLPNLHNDSVVSLEEIDKNLKSLERCQSLEEIQRLYEAGDYKAVVHLLRPTLCTSG

FROM FIG. 9A

FDRAKHLEFMTSIPERPAQLLLLQDSLLRLKDYRQCFECSDVALNEAVQQMVNSGEAAAK
EEWVATVTQLLMGIEQALSADSSGSILKVSSSTTGLVRLTNNLIQVIDCSMAVQEEAKEP
HVSSVLPWIILHRIIWQEEDTFHSLCHQQQLQNPAEEGMSETPMLPSSLMLLNTAHEYLG
RRSWCCNSDGALLRFYVRVLQKELAASTSEDTHPYKEELETALEQCFYCLYSFPSKKSKA
RYLEEHSAQQVDLIWEDALFMFEYFKPKTLPEFDSYKTSTVSADLANLLKRIATIVPRTE
RPALSLDKVSAYIEGTSTEVPCLPEGADPSPPVVNELYYLLADYHFKNKEQSKAIKFYMH
DICICPNRFDSWAGMALARASRIQDKLNSNELKSDGPIWKHATPVLNCFRRALEIDSSNL
SLWIEYGTMSYALHSFASRQLKQWRGELPPELVQQMEGRRDSMLETAKHCFTSAARCEGD
GDEEEWLIHYMLGKVAEKQQQPPTVYLLHYRQAGHYLHEEAARYPKKIHYHNPPELAMEA
LEVYFRLHASILKLLLGKPDSGVGAEVLVNFMKEAAEGPFARGEEKNTPKASEKEKACLVD
EDSHSSAGTLPGPGASLPSSSGPGLTSPPYTATPIDHDYVKCKKPHQQATPDDRSQDSTA
VALSDSSSTQDFFNEPTSLLEGSRKSYTEKRLPILSSQAGATGKDLQGATEERGKNEESL
ESTEGFRAAEQGVQKPAAETPASACIPGKPSASTPTLWDGKKRGDLPGEPVAFPQGLPAG

FROM FIG. 9B

AEEQRQFLTEQCIASFRLCLSRFPQHYKSLYRLAFLYTYSKTHRNLQWARDVLLGSSIPW
QQLQHMPAQGLFCERNKTNFFNGIWRIPVDEIDRPGSFAWHMNRSIVLLLKVLAQLRDHS
TLLKVSSMLQRTPDQGKKYLRDADRQVLAQRAFILTVKVLEDTLSELAEGSERPGPKVCG
LPGARMTTDVSHKASPEDGGQEGLPQPKKPPLADGSGPGPEPGGKVGLLNHRPVAMDAGDS
ADQSGERKDKESPRAGPTEPMDTSEATVCHSDLERTPPLLPGRPARDRGPESRPTELSLE
ELSISARQQPTPLTPAQPAPAPAPATTTGTRAGGHPEEPLSRKRKLLEDTESGKTLL
LDAYRVWQQGQQKGVAYDLGRVERIMSETYMLIKQVDEEAALEQAVKFCQVHLGAAAQRQA
SGDTPTTPKHPKDSRENFFPVTVVPTAPDPVPADSVQRPSDAHTKPRPALAAATTIITCP
PSASASTLDQSKDPGPPRPHRPEATPSMASLGPEGEELARVAEGTSFPPQEPRHSPQVKM
APTSSPAEPHCWPAEAALGTGAEPTCSQEGKLRPEPRRDGEAQEAASETQPLSSPPTAAS
SKAPSSGSAQPPEGHPGKPEPSRAKSRPLPNMPKLVIPSAATKFPPEITVTPPTLLSP
KGSISEETKQKLKSAILSAQSAANVRKESLCQPALEVLETSSQESSLESETDEDDDYMDI
(SEQ ID NO:1)

FIG. 10

Cabin 1–154 cDNA Sequence caggtgaagatggccccacagttccccggcagagccacactgctggccggcagaggctgcctgggcacaggcgctgagc
ccacctgcagcggagggaactgaggctgaggctcaaggctgcgagggagggatgggaggctcaggaggctgcgagtgagactcagcc
cctgagctctccccaacagctgccagtccaaggctcaaggccaccagagggtcaccaggca
agcctgagccagcggctaagtccgccgccagccaccaagtggtcatccctccgccaccagttc
ccccctgagatcaccgtcacgcccaccaccccacccgtctctcccccaaggcagcatctcggaggagaccaagcagaa
gctgaagtcagcatcctttctgccagtctgctgcaaacgtgaggaggagcatgccagccagactggaggtcc
tggagacatccagccaggagtcctcgctggagggacgagacgaggacgacgactccatggacatt (SEQ ID NO:9)

FIG. 11

Cabin 1–154 Polypeptide Sequence

QVKMAPTSSPAEPHCWPAEAALGTGAEPTCSQEGKLRPEPRRDGEAQEAASETQPLSSPPTAAS
SKAPSSGSAQPPEGHPGKPEPSRAKSRPLPNMPKLVIPSAATKFPPEITVTPPTPTLLSPKGSI
SEETKQKLKSAILSAQSAANVRKESLCQPALEVLETSSQESSLESETDEDDDYMDI
(SEQ ID NO:2)

FIG. 12
Cabin 1-6 cDNA Sequence gcagaggctgccctgggcacaggcgctgagccacctgcagccaggagggaaactgaggcctgagccgagaggatgg
ggaggctcaggaggctgcgagtgagactcagcctgagctctccccacagctgccagtccaaggcctcaaggcccccagcagtggg
agtgccagcagagggtcaccaggagctgagccaggccggctaagtccgccccctgccaacatgccaaagc
tggtcatccctccgcgccaccaagttccccctgagatcacgtcacgcaccaccaccccctgctctccccaagg
cagcatctcggagagagaccaagcagaagctgaagtcagccatcctttctgccagtcctgctgccaacgtggagggagagc
ctatgccagccagccctggagtcctggagacatccagccagccaggagtcctcgctgagagcgagcggagacgaggacgact
acatggacatttga (SEQ ID NO:10)

FIG. 13
Cabin 1-6 Polypeptide Sequence

AEAALGTGAEPTCSQEGKLRPEPRRDGEAQEAASETQPLSSPPTAAS
SKAPSSGSAQPPEGHPGKPEPSRAKSRPLPNMPKLVIPSAATKFPPEITVTPPTPTLLSPKGSI
SEETKQKLKSAILSAQSAANVRKESLCQPALEVLETSSQESSLESETDEDDDYMDI (SEQ ID NO:3)

FIG. 14
Cabin 1-97 cDNA Sequence gctaagtcccgcccctgccaacatgccaaagctggtcatccctccgccgccaccaagttcccccctgagatcaccgtca
cgccaccaccaccctgctctccccaaggcagcatctcggaggagaccaagcaagaagctgaagtcagccatccttc
tgccagtctgctgccaacgtgtgaggaaggagagctatgccagcaggcctggggtcctggagacatccagccaggagtcc
tcgctggagagcgagagcgagacgaggacgactacatggacatttga (SEQ ID NO:11)

FIG. 15
Cabin 1-97 Polypeptide Sequence

AKSRPLPNMPKLVIPSAATKFPPEITVTPPTPTLLSPKGSISEETKQKLKSAILSAQSAANVRKESLCQ
PALEVLETSSQESSLESETDEDDDYMDI (SEQ ID NO:4)

FIG.16
Cabin 1-14 cDNA Sequence aagttccccctgagatcaccgtcacgccaccaccccaccctgtctcccccaaggcagcatctcggaggagaccaagc
agaagtgaagtcagcatccttctgccagtctgctgccaacgtgaggaggagcctatgccagccagccctggaggt
cctggagacatccagccaggagtcctcgctggagagcgagcaggacgaggacgactacatggacatttga (SEQ ID NO:12)

FIG.17
Cabin 1-14 Polypeptide Sequence

KFPPEITVTPPTPTLLSPKGSISEETKQKLKSAILSAQSAANVRKESLCQPALEVLETSSQESSLESET
DEDDDYMDI (SEQ ID NO:5)

FIG. 18
Cabin 1-CNBD23 cDNA Sequence ttcccctgagatcacgtcaccgcaccccaccctgctctacccaaggcagcatctcggag (SEQ ID NO:13)

FIG. 19
Cabin 1-CNBD23 Polypeptide Sequence

FPPEITVTPPTPTLLSPKGSISE (SEQ ID NO:6)

FIG. 20
Cabin 1-CNBD13 cDNA Sequence ttcccctgagatcaccgtcacgtcacgccacccaacc
(SEQ ID NO:14)

FIG. 21
Cabin 1-CNBD13 Polypeptide Sequence

FPPEITVTPPTPT
(SEQ ID NO:7)

SEQUENCE LISTING

<160> NUMBER OF SEQ ID NOS: 15

<210> SEQ ID NO 1
<211> LENGTH: 2220
<212> TYPE: PRT
<213> ORGANISM: Homo sapiens

<400> SEQUENCE: 1

```
Met Ile Arg Ile Ala Ala Leu Asn Ala Ser Ser Thr Ile Glu Asp Asp
 1               5                  10                  15

His Glu Gly Ser Phe Lys Ser His Lys Thr Gln Thr Lys Glu Ala Gln
                20                  25                  30

Glu Ala Glu Ala Phe Ala Leu Tyr His Lys Ala Leu Asp Leu Gln Lys
            35                  40                  45

His Asp Arg Phe Glu Glu Ser Ala Lys Ala Tyr His Glu Leu Leu Glu
        50                  55                  60

Ala Ser Leu Leu Arg Glu Ala Val Ser Ser Gly Asp Glu Lys Glu Gly
 65                 70                  75                  80

Leu Lys His Pro Gly Leu Ile Leu Lys Tyr Ser Thr Tyr Lys Asn Leu
                85                  90                  95

Ala Gln Leu Ala Ala Gln Arg Glu Asp Leu Glu Thr Ala Met Glu Phe
            100                 105                 110

Tyr Leu Glu Ala Val Met Leu Asp Ser Thr Asp Val Asn Leu Trp Tyr
        115                 120                 125

Lys Ile Gly His Val Ala Leu Arg Leu Ile Arg Ile Pro Leu Ala Arg
    130                 135                 140

His Ala Phe Glu Glu Gly Leu Arg Cys Asn Pro Asp His Trp Pro Cys
145                 150                 155                 160

Leu Asp Asn Leu Ile Thr Val Leu Tyr Thr Leu Ser Asp Tyr Thr Thr
                165                 170                 175

Cys Leu Tyr Phe Ile Cys Lys Ala Leu Glu Lys Asp Cys Arg Tyr Ser
            180                 185                 190

Lys Gly Leu Val Leu Lys Glu Lys Ile Phe Glu Gln Pro Cys Leu
        195                 200                 205

Arg Lys Asp Ser Leu Arg Met Phe Leu Cys Asp Met Ser Ile His
    210                 215                 220

Asp Val Ser Val Ser Ala Ala Glu Thr Gln Ala Ile Val Asp Glu Ala
225                 230                 235                 240

Leu Gly Leu Arg Lys Lys Arg Gln Ala Leu Ile Val Arg Glu Lys Glu
                245                 250                 255

Pro Asp Leu Lys Leu Val Gln Pro Ile Pro Phe Thr Trp Lys Cys
            260                 265                 270

Leu Gly Glu Ser Leu Leu Ala Met Tyr Asn His Leu Thr Thr Cys Glu
        275                 280                 285

Pro Pro Arg Pro Ser Leu Gly Lys Arg Ile Asp Leu Ser Asp Tyr Gln
    290                 295                 300

Asp Pro Ser Gln Pro Leu Glu Ser Ser Met Val Val Thr Pro Val Asn
305                 310                 315                 320

Val Ile Gln Pro Ser Thr Val Ser Thr Asn Pro Ala Val Ala Val Ala
                325                 330                 335

Glu Pro Val Ser Tyr Thr Ser Val Ala Thr Thr Ser Phe Pro Leu
            340                 345                 350

His Ser Pro Gly Leu Leu Glu Thr Gly Ala Pro Val Gly Asp Ile Ser
```

-continued

```
                355                 360                 365
Gly Gly Asp Lys Ser Lys Lys Gly Val Lys Arg Lys Lys Ile Ser Glu
        370                 375                 380
Glu Ser Gly Glu Thr Ala Lys Arg Arg Ser Ala Arg Val Arg Asn Thr
385                 390                 395                 400
Lys Cys Lys Lys Glu Glu Lys Val Asp Phe Gln Glu Leu Leu Met Lys
                405                 410                 415
Phe Leu Pro Ser Arg Leu Arg Lys Leu Asp Pro Glu Glu Asp Asp
                420                 425                 430
Ser Phe Asn Asn Tyr Glu Val Gln Ser Glu Ala Lys Leu Glu Ser Phe
        435                 440                 445
Pro Ser Ile Gly Pro Gln Arg Leu Ser Phe Asp Ser Ala Thr Phe Met
450                 455                 460
Glu Ser Glu Lys Gln Asp Val His Glu Phe Leu Leu Glu Asn Leu Thr
465                 470                 475                 480
Asn Gly Gly Ile Leu Glu Leu Met Met Arg Tyr Leu Lys Ala Met Gly
                485                 490                 495
His Lys Phe Leu Val Arg Trp Pro Pro Gly Leu Ala Glu Val Val Leu
                500                 505                 510
Ser Val Tyr His Ser Trp Arg Arg His Ser Thr Ser Leu Pro Asn Pro
        515                 520                 525
Leu Leu Arg Asp Cys Ser Asn Lys His Ile Lys Asp Met Met Leu Met
        530                 535                 540
Ser Leu Ser Cys Met Glu Leu Gln Leu Asp Gln Trp Leu Leu Thr Lys
545                 550                 555                 560
Gly Arg Ser Ser Ala Val Ser Pro Arg Asn Cys Pro Ala Gly Met Val
                565                 570                 575
Asn Gly Arg Phe Gly Pro Asp Phe Pro Gly Thr His Cys Leu Gly Asp
                580                 585                 590
Leu Leu Gln Leu Ser Phe Ala Ser Ser Gln Arg Asp Leu Phe Glu Asp
        595                 600                 605
Gly Trp Leu Glu Phe Val Val Arg Val Tyr Trp Leu Lys Ala Arg Phe
        610                 615                 620
Leu Ala Leu Gln Gly Asp Met Glu Gln Ala Leu Glu Asn Tyr Asp Ile
625                 630                 635                 640
Cys Thr Glu Met Leu Gln Ser Ser Thr Ala Ile Gln Val Glu Ala Gly
                645                 650                 655
Ala Glu Arg Arg Asp Ile Val Ile Arg Leu Pro Asn Leu His Asn Asp
                660                 665                 670
Ser Val Val Ser Leu Glu Glu Ile Asp Lys Asn Leu Lys Ser Leu Glu
        675                 680                 685
Arg Cys Gln Ser Leu Glu Glu Ile Gln Arg Leu Tyr Glu Ala Gly Asp
        690                 695                 700
Tyr Lys Ala Val Val His Leu Leu Arg Pro Thr Leu Cys Thr Ser Gly
705                 710                 715                 720
Phe Asp Arg Ala Lys His Leu Glu Phe Met Thr Ser Ile Pro Glu Arg
                725                 730                 735
Pro Ala Gln Leu Leu Leu Leu Gln Asp Ser Leu Leu Arg Leu Lys Asp
                740                 745                 750
Tyr Arg Gln Cys Phe Glu Cys Ser Asp Val Ala Leu Asn Glu Ala Val
        755                 760                 765
Gln Gln Met Val Asn Ser Gly Glu Ala Ala Lys Glu Glu Trp Val
        770                 775                 780
```

-continued

```
Ala Thr Val Thr Gln Leu Leu Met Gly Ile Glu Gln Ala Leu Ser Ala
785                 790                 795                 800

Asp Ser Ser Gly Ser Ile Leu Lys Val Ser Ser Thr Thr Gly Leu
            805                 810                 815

Val Arg Leu Thr Asn Asn Leu Ile Gln Val Ile Asp Cys Ser Met Ala
            820                 825                 830

Val Gln Glu Glu Ala Lys Glu Pro His Val Ser Ser Val Leu Pro Trp
            835                 840                 845

Ile Ile Leu His Arg Ile Ile Trp Gln Glu Asp Thr Phe His Ser
850                 855                 860

Leu Cys His Gln Gln Gln Leu Gln Asn Pro Ala Glu Glu Gly Met Ser
865                 870                 875                 880

Glu Thr Pro Met Leu Pro Ser Ser Leu Met Leu Asn Thr Ala His
                885                 890                 895

Glu Tyr Leu Gly Arg Arg Ser Trp Cys Cys Asn Ser Asp Gly Ala Leu
                900                 905                 910

Leu Arg Phe Tyr Val Arg Val Leu Gln Lys Glu Leu Ala Ala Ser Thr
            915                 920                 925

Ser Glu Asp Thr His Pro Tyr Lys Glu Glu Leu Glu Thr Ala Leu Glu
    930                 935                 940

Gln Cys Phe Tyr Cys Leu Tyr Ser Phe Pro Ser Lys Lys Ser Lys Ala
945                 950                 955                 960

Arg Tyr Leu Glu Glu His Ser Ala Gln Gln Val Asp Leu Ile Trp Glu
                965                 970                 975

Asp Ala Leu Phe Met Phe Glu Tyr Phe Lys Pro Lys Thr Leu Pro Glu
            980                 985                 990

Phe Asp Ser Tyr Lys Thr Ser Thr Val Ser Ala Asp Leu Ala Asn Leu
            995                 1000                1005

Leu Lys Arg Ile Ala Thr Ile Val Pro Arg Thr Glu Arg Pro Ala Leu
    1010                1015                1020

Ser Leu Asp Lys Val Ser Ala Tyr Ile Glu Gly Thr Ser Thr Glu Val
1025                1030                1035                1040

Pro Cys Leu Pro Glu Gly Ala Asp Pro Ser Pro Pro Val Val Asn Glu
                1045                1050                1055

Leu Tyr Tyr Leu Leu Ala Asp Tyr His Phe Lys Asn Lys Glu Gln Ser
                1060                1065                1070

Lys Ala Ile Lys Phe Tyr Met His Asp Ile Cys Ile Cys Pro Asn Arg
            1075                1080                1085

Phe Asp Ser Trp Ala Gly Met Ala Leu Ala Arg Ala Ser Arg Ile Gln
    1090                1095                1100

Asp Lys Leu Asn Ser Asn Glu Leu Lys Ser Asp Gly Pro Ile Trp Lys
1105                1110                1115                1120

His Ala Thr Pro Val Leu Asn Cys Phe Arg Arg Ala Leu Glu Ile Asp
                1125                1130                1135

Ser Ser Asn Leu Ser Leu Trp Ile Glu Tyr Gly Thr Met Ser Tyr Ala
            1140                1145                1150

Leu His Ser Phe Ala Ser Arg Gln Leu Lys Gln Trp Arg Gly Glu Leu
    1155                1160                1165

Pro Pro Glu Leu Val Gln Gln Met Glu Gly Arg Arg Asp Ser Met Leu
    1170                1175                1180

Glu Thr Ala Lys His Cys Phe Ser Ala Ala Arg Cys Glu Gly Asp
1185                1190                1195                1200
```

```
Gly Asp Glu Glu Glu Trp Leu Ile His Tyr Met Leu Gly Lys Val Ala
            1205                1210                1215
Glu Lys Gln Gln Gln Pro Pro Thr Val Tyr Leu Leu His Tyr Arg Gln
            1220                1225                1230
Ala Gly His Tyr Leu His Glu Glu Ala Ala Arg Tyr Pro Lys Lys Ile
            1235                1240                1245
His Tyr His Asn Pro Pro Glu Leu Ala Met Glu Ala Leu Glu Val Tyr
    1250                1255                1260
Phe Arg Leu His Ala Ser Ile Leu Lys Leu Leu Gly Lys Pro Asp Ser
1265                1270                1275                1280
Gly Val Gly Ala Glu Val Leu Val Asn Phe Met Lys Glu Ala Ala Glu
            1285                1290                1295
Gly Pro Phe Ala Arg Gly Glu Glu Lys Asn Thr Pro Lys Ala Ser Glu
            1300                1305                1310
Lys Glu Lys Ala Cys Leu Val Asp Glu Asp Ser His Ser Ser Ala Gly
            1315                1320                1325
Thr Leu Pro Gly Pro Gly Ala Ser Leu Pro Ser Ser Ser Gly Pro Gly
            1330                1335                1340
Leu Thr Ser Pro Pro Tyr Thr Ala Thr Pro Ile Asp His Asp Tyr Val
1345                1350                1355                1360
Lys Cys Lys Lys Pro His Gln Gln Ala Thr Pro Asp Asp Arg Ser Gln
            1365                1370                1375
Asp Ser Thr Ala Val Ala Leu Ser Asp Ser Ser Ser Thr Gln Asp Phe
            1380                1385                1390
Phe Asn Glu Pro Thr Ser Leu Leu Glu Gly Ser Arg Lys Ser Tyr Thr
            1395                1400                1405
Glu Lys Arg Leu Pro Ile Leu Ser Ser Gln Ala Gly Ala Thr Gly Lys
    1410                1415                1420
Asp Leu Gln Gly Ala Thr Glu Glu Arg Gly Lys Asn Glu Glu Ser Leu
1425                1430                1435                1440
Glu Ser Thr Glu Gly Phe Arg Ala Ala Glu Gln Gly Val Gln Lys Pro
            1445                1450                1455
Ala Ala Glu Thr Pro Ala Ser Ala Cys Ile Pro Gly Lys Pro Ser Ala
            1460                1465                1470
Ser Thr Pro Thr Leu Trp Asp Gly Lys Lys Arg Gly Asp Leu Pro Gly
            1475                1480                1485
Glu Pro Val Ala Phe Pro Gln Gly Leu Pro Ala Gly Ala Glu Glu Gln
    1490                1495                1500
Arg Gln Phe Leu Thr Glu Gln Cys Ile Ala Ser Phe Arg Leu Cys Leu
1505                1510                1515                1520
Ser Arg Phe Pro Gln His Tyr Lys Ser Leu Tyr Arg Leu Ala Phe Leu
            1525                1530                1535
Tyr Thr Tyr Ser Lys Thr His Arg Asn Leu Gln Trp Ala Arg Asp Val
            1540                1545                1550
Leu Leu Gly Ser Ser Ile Pro Trp Gln Gln Leu Gln His Met Pro Ala
    1555                1560                1565
Gln Gly Leu Phe Cys Glu Arg Asn Lys Thr Asn Phe Phe Asn Gly Ile
    1570                1575                1580
Trp Arg Ile Pro Val Asp Glu Ile Asp Arg Pro Gly Ser Phe Ala Trp
1585                1590                1595                1600
His Met Asn Arg Ser Ile Val Leu Leu Leu Lys Val Leu Ala Gln Leu
            1605                1610                1615
Arg Asp His Ser Thr Leu Leu Lys Val Ser Ser Met Leu Gln Arg Thr
```

-continued

```
                    1620                1625                1630
    Pro Asp Gln Gly Lys Lys Tyr Leu Arg Asp Ala Asp Arg Gln Val Leu
            1635                1640                1645
    Ala Gln Arg Ala Phe Ile Leu Thr Val Lys Val Leu Glu Asp Thr Leu
    1650                1655                1660
    Ser Glu Leu Ala Glu Gly Ser Glu Arg Gly Pro Lys Val Cys Gly
    1665                1670                1675                1680
    Leu Pro Gly Ala Arg Met Thr Thr Asp Val Ser His Lys Ala Ser Pro
            1685                1690                1695
    Glu Asp Gly Gln Glu Gly Leu Pro Gln Pro Lys Lys Pro Pro Leu Ala
            1700                1705                1710
    Asp Gly Ser Gly Pro Gly Pro Glu Pro Gly Gly Lys Val Gly Leu Leu
            1715                1720                1725
    Asn His Arg Pro Val Ala Met Asp Ala Gly Asp Ser Ala Asp Gln Ser
            1730                1735                1740
    Gly Glu Arg Lys Asp Lys Glu Ser Pro Arg Ala Gly Pro Thr Glu Pro
    1745                1750                1755                1760
    Met Asp Thr Ser Glu Ala Thr Val Cys His Ser Asp Leu Glu Arg Thr
            1765                1770                1775
    Pro Pro Leu Leu Pro Gly Arg Pro Ala Arg Asp Arg Gly Pro Glu Ser
            1780                1785                1790
    Arg Pro Thr Glu Leu Ser Leu Glu Glu Leu Ser Ile Ser Ala Arg Gln
            1795                1800                1805
    Gln Pro Thr Pro Leu Thr Pro Ala Gln Pro Ala Pro Ala Pro
            1810                1815                1820
    Ala Thr Thr Thr Gly Thr Arg Ala Gly Gly His Pro Glu Glu Pro Leu
    1825                1830                1835                1840
    Ser Arg Leu Ser Arg Lys Arg Lys Leu Leu Glu Asp Thr Glu Ser Gly
            1845                1850                1855
    Lys Thr Leu Leu Leu Asp Ala Tyr Arg Val Trp Gln Gln Gly Gln Lys
            1860                1865                1870
    Gly Val Ala Tyr Asp Leu Gly Arg Val Glu Arg Ile Met Ser Glu Thr
            1875                1880                1885
    Tyr Met Leu Ile Lys Gln Val Asp Glu Glu Ala Ala Leu Glu Gln Ala
            1890                1895                1900
    Val Lys Phe Cys Gln Val His Leu Gly Ala Ala Ala Gln Arg Gln Ala
    1905                1910                1915                1920
    Ser Gly Asp Thr Pro Thr Thr Pro Lys His Pro Lys Asp Ser Arg Glu
            1925                1930                1935
    Asn Phe Phe Pro Val Thr Val Val Pro Thr Ala Pro Asp Pro Val Pro
            1940                1945                1950
    Ala Asp Ser Val Gln Arg Pro Ser Asp Ala His Thr Lys Pro Arg Pro
            1955                1960                1965
    Ala Leu Ala Ala Ala Thr Thr Ile Ile Thr Cys Pro Pro Ser Ala Ser
            1970                1975                1980
    Ala Ser Thr Leu Asp Gln Ser Lys Asp Pro Gly Pro Pro Arg Pro His
    1985                1990                1995                2000
    Arg Pro Glu Ala Thr Pro Ser Met Ala Ser Leu Gly Pro Glu Gly Glu
                    2005                2010                2015
    Glu Leu Ala Arg Val Ala Glu Gly Thr Ser Phe Pro Pro Gln Glu Pro
            2020                2025                2030
    Arg His Ser Pro Gln Val Lys Met Ala Pro Thr Ser Ser Pro Ala Glu
            2035                2040                2045
```

```
Pro His Cys Trp Pro Ala Glu Ala Ala Leu Gly Thr Gly Ala Glu Pro
    2050                2055                2060

Thr Cys Ser Gln Glu Gly Lys Leu Arg Pro Glu Pro Arg Arg Asp Gly
2065                2070                2075                2080

Glu Ala Gln Glu Ala Ala Ser Glu Thr Gln Pro Leu Ser Ser Pro Pro
            2085                2090                2095

Thr Ala Ala Ser Ser Lys Ala Pro Ser Ser Gly Ser Ala Gln Pro Pro
        2100                2105                2110

Glu Gly His Pro Gly Lys Pro Glu Pro Ser Arg Ala Lys Ser Arg Pro
    2115                2120                2125

Leu Pro Asn Met Pro Lys Leu Val Ile Pro Ser Ala Ala Thr Lys Phe
        2130                2135                2140

Pro Pro Glu Ile Thr Val Thr Pro Pro Thr Pro Thr Leu Leu Ser Pro
2145                2150                2155                2160

Lys Gly Ser Ile Ser Glu Glu Thr Lys Gln Lys Leu Lys Ser Ala Ile
            2165                2170                2175

Leu Ser Ala Gln Ser Ala Ala Asn Val Arg Lys Glu Ser Leu Cys Gln
        2180                2185                2190

Pro Ala Leu Glu Val Leu Glu Thr Ser Ser Gln Glu Ser Ser Leu Glu
        2195                2200                2205

Ser Glu Thr Asp Glu Asp Asp Asp Tyr Met Asp Ile
    2210                2215                2220

<210> SEQ ID NO 2
<211> LENGTH: 184
<212> TYPE: PRT
<213> ORGANISM: Homo sapiens

<400> SEQUENCE: 2

Gln Val Lys Met Ala Pro Thr Ser Ser Pro Ala Glu Pro His Cys Trp
 1               5                  10                  15

Pro Ala Glu Ala Ala Leu Gly Thr Gly Ala Glu Pro Thr Cys Ser Gln
            20                  25                  30

Glu Gly Lys Leu Arg Pro Glu Pro Arg Arg Asp Gly Glu Ala Gln Glu
        35                  40                  45

Ala Ala Ser Glu Thr Gln Pro Leu Ser Ser Pro Pro Thr Ala Ala Ser
    50                  55                  60

Ser Lys Ala Pro Ser Ser Gly Ser Ala Gln Pro Pro Glu Gly His Pro
65                  70                  75                  80

Gly Lys Pro Glu Pro Ser Arg Ala Lys Ser Arg Pro Leu Pro Asn Met
                85                  90                  95

Pro Lys Leu Val Ile Pro Ser Ala Ala Thr Lys Phe Pro Pro Glu Ile
            100                 105                 110

Thr Val Thr Pro Pro Thr Pro Thr Leu Leu Ser Pro Lys Gly Ser Ile
        115                 120                 125

Ser Glu Glu Thr Lys Gln Lys Leu Lys Ser Ala Ile Leu Ser Ala Gln
    130                 135                 140

Ser Ala Ala Asn Val Arg Lys Glu Ser Leu Cys Gln Pro Ala Leu Glu
145                 150                 155                 160

Val Leu Glu Thr Ser Ser Gln Glu Ser Ser Leu Glu Ser Glu Thr Asp
                165                 170                 175

Glu Asp Asp Asp Tyr Met Asp Ile
            180
```

```
<210> SEQ ID NO 3
<211> LENGTH: 167
<212> TYPE: PRT
<213> ORGANISM: Homo sapiens

<400> SEQUENCE: 3

Ala Glu Ala Ala Leu Gly Thr Gly Ala Glu Pro Thr Cys Ser Gln Glu
 1               5                  10                  15

Gly Lys Leu Arg Pro Glu Pro Arg Arg Asp Gly Glu Ala Gln Glu Ala
            20                  25                  30

Ala Ser Glu Thr Gln Pro Leu Ser Ser Pro Thr Ala Ala Ser Ser
        35                  40                  45

Lys Ala Pro Ser Ser Gly Ser Ala Gln Pro Pro Glu Gly His Pro Gly
 50                  55                  60

Lys Pro Glu Pro Ser Arg Ala Lys Ser Arg Pro Leu Pro Asn Met Pro
 65                  70                  75                  80

Lys Leu Val Ile Pro Ser Ala Ala Thr Lys Phe Pro Pro Glu Ile Thr
                85                  90                  95

Val Thr Pro Pro Thr Pro Thr Leu Leu Ser Pro Lys Gly Ser Ile Ser
               100                 105                 110

Glu Glu Thr Lys Gln Lys Leu Lys Ser Ala Ile Leu Ser Ala Gln Ser
           115                 120                 125

Ala Ala Asn Val Arg Lys Glu Ser Leu Cys Gln Pro Ala Leu Glu Val
130                 135                 140

Leu Glu Thr Ser Ser Gln Glu Ser Leu Glu Ser Glu Thr Asp Glu
145                 150                 155                 160

Asp Asp Asp Tyr Met Asp Ile
                165

<210> SEQ ID NO 4
<211> LENGTH: 97
<212> TYPE: PRT
<213> ORGANISM: Homo sapiens

<400> SEQUENCE: 4

Ala Lys Ser Arg Pro Leu Pro Asn Met Pro Lys Leu Val Ile Pro Ser
 1               5                  10                  15

Ala Ala Thr Lys Phe Pro Pro Glu Ile Thr Val Thr Pro Pro Thr Pro
            20                  25                  30

Thr Leu Leu Ser Pro Lys Gly Ser Ile Ser Glu Glu Thr Lys Gln Lys
        35                  40                  45

Leu Lys Ser Ala Ile Leu Ser Ala Gln Ser Ala Ala Asn Val Arg Lys
 50                  55                  60

Glu Ser Leu Cys Gln Pro Ala Leu Glu Val Leu Glu Thr Ser Ser Gln
 65                  70                  75                  80

Glu Ser Ser Leu Glu Ser Glu Thr Asp Glu Asp Asp Asp Tyr Met Asp
                85                  90                  95

Ile

<210> SEQ ID NO 5
<211> LENGTH: 78
<212> TYPE: PRT
<213> ORGANISM: Homo sapiens

<400> SEQUENCE: 5

Lys Phe Pro Pro Glu Ile Thr Val Thr Pro Pro Thr Pro Thr Leu Leu
 1               5                  10                  15
```

```
Ser Pro Lys Gly Ser Ile Ser Glu Glu Thr Lys Gln Lys Leu Lys Ser
            20                  25                  30

Ala Ile Leu Ser Ala Gln Ser Ala Ala Asn Val Arg Lys Glu Ser Leu
        35                  40                  45

Cys Gln Pro Ala Leu Glu Val Leu Glu Leu Thr Ser Ser Gln Glu Ser Ser
    50                  55                  60

Leu Glu Ser Glu Thr Asp Glu Asp Asp Tyr Met Asp Ile
65                  70                  75

<210> SEQ ID NO 6
<211> LENGTH: 23
<212> TYPE: PRT
<213> ORGANISM: Homo sapiens

<400> SEQUENCE: 6

Phe Pro Pro Glu Ile Thr Val Thr Pro Pro Thr Pro Thr Leu Leu Ser
1               5                   10                  15

Pro Lys Gly Ser Ile Ser Glu
            20

<210> SEQ ID NO 7
<211> LENGTH: 13
<212> TYPE: PRT
<213> ORGANISM: Homo sapiens

<400> SEQUENCE: 7

Phe Pro Pro Glu Ile Thr Val Thr Pro Pro Thr Pro Thr
1               5                   10

<210> SEQ ID NO 8
<211> LENGTH: 7223
<212> TYPE: DNA
<213> ORGANISM: Homo sapiens

<400> SEQUENCE: 8
tagccggacg gcgcggtggt cgggacagac tggccgttgc tgtggagacg cctggagagt      60
tgtggactgg ggcaaccttt gccagtgatg agaagtgatg ctcgtggcag tgctgaatct     120
ctctgaatat gattcgaatt gcagccttaa atgccagctc caccattgag gatgatcatg     180
aaggaagctt taaaagtcac aaaacccaga caaaggaggc tcaggaagca gaggcttttg     240
cattgtacca aaggccctt gatctgcaga acatgaccg gtttgaggag tctgccaaag      300
cctaccatga gctcttggag gcgagcctgc tgcgggaggc agtttcatcc ggtgatgaga     360
agaggggtt gaaacaccct gggctgatac tgaaatattc cacttataag aacttggccc     420
agctggcagc ccagcgggag gatctggaga cagccatgga gttctactta gaggcagtga     480
tgctggactc cacagatgtc aacctctggt ataagattgg acatgtggcc ctgaggctca     540
tccggatccc cctggctcgc catgcttttg aggaagggct gcggtgcaat cctgaccact     600
ggccctgttt ggataaccta atcactgtcc tgtacaccct cagtgattac acaacatgtc     660
tgtacttcat ctgcaaagct ttggagaagg attgccggta cagcaaaggg ctggtcctca     720
aggagaagat ttttgaggag cagccttgtc tccggaagga ctctctcaga atgttcctca     780
aatgtgacat gtcgattcac gatgtttcgg tgagtgcagc tgagacacag gcgattgtag     840
atgaggcctt ggggctgcga aaaaagaggc aagcgctgat tgtgcgggag aaggagccgg     900
acctgaaaact tgtgcagccc attccttttct tcacctggaa gtgcctcgga gagagcttgc     960
tggccatgta caatcatctc accacctgtg agccccacg tcccagcctt ggcaaaagga    1020
```

-continued

```
ttgatttgtc ggactaccag gaccccagcc agcctcttga gtcctccatg gtggtgacgc    1080
cagttaacgt gatccagcca agcactgtca gcaccaaccc agctgtggct gtcgccgagc    1140
ctgtggtctc ctacacctct gtggctacaa ccagcttccc actgcacagt cctggtctgt    1200
tggagacagg cgctcctgtg ggtgatattt ctgggggaga taaatccaag aaagggtaa     1260 aacggaagaa gatttcagaa gagagtggag aaacagcaaa gcggcggtct gcccgtgtcc    1320
gaaacaccaa gtgcaaaaaa gaagagaaag tagacttcca ggagcttctg atgaagttct    1380
tgccgtccag gttaagaaag ctggaccctg aggaggaaga tgattccttt aataactatg    1440
aagtccagtc agaagccaaa ctggaaagct cccaagcat tgggcctcaa aggctgtcat     1500
ttgactcagc cacattcatg gaatctgaaa agcaggacgt gcatgagttc ctgctggaga    1560
acctaaccaa cggggggcatc ctggagctga tgatgcgcta cctgaaagcc atgggccaca   1620
agttcttggt aaggtggcct ccaggcttgg cggaggtcgt gctcagcgtc taccacagct    1680
ggaggaggca cagcaccagc ctgcccaacc cgctgctgag ggactgcagc aacaagcaca    1740
tcaaggacat gatgctgatg tctctctcct gcatggaact ccagctggac cagtggctgc    1800
tgaccaaagg cagaagctct gcagtgtctc ctcggaactg ccctgctggt atggtgaatg    1860
gcagatttgg acctgacttc ccagggaccc actgcctggg tgacctccta cagctgtcat    1920
ttgcctcgtc ccagcgcgac ctgttcgagg atggttggct ggagtttgtg gtccgtgttt    1980
actggctgaa ggctcgcttc ctggcgctga agggagacat ggagcaggcc ctggagaact    2040
atgacatctg cacagaaatg ctccagagtt ccaccgccat ccagtggag gcaggggctg      2100 aacgaagaga cattgtcatc cggctgccca acctccataa tgactctgtg gtttccctgg    2160
aggagattga taagaacctg aagtcgctgg agcggtgcca gtccctggag agattcagc      2220 ggctgtatga agcaggcgac tacaaggctg ttgtgcatct gctccgcccc actttgtgca    2280
ccagtgggtt tgaccgggcc aaacacctgg agtttatgac ttccattcct gagaggccag    2340
cccagctgct tcttctgcag gactccttgc tccggctgaa ggactatcgg cagtgttttg    2400
agtgttccga tgtggctctg aacgaggctg tccagcagat ggtgaactca ggtgaggctg    2460
ccgccaagga ggagtggggtg gccacagtga cccaactgct gatgggcatc gagcaggccc   2520
tctctgcgga cagcagtggt agcatcctga aggtatcatc ctccaccact ggccttgtgc    2580
ggctcaccaa caacctcatc caggtcattg actgcagcat ggctgtgcag gaggaggcca    2640
aggagcccca cgtctcttca gtgctaccct ggatcattct acaccggatc atctggcagg    2700
aggaagacac cttccattct ctgtgccacc agcagcagct ccaaaaccca gcggaggaag    2760
ggatgtcaga gacgcccatg ctcccatcct ccctcatgct gctgaacaca gcccacgagt    2820
atttgggcag aaggtcctgg tgctgcaatt cagatggggc tctgctgcga ttctatgtgc    2880
gagtactcca gaaggaactg gctgcatcca cctctgaaga cacgcaccct tacaaggagg    2940
agctggagac agccttggag cagtgcttct actgcctgta cagcttcccc agcaagaaga    3000
gtaaggccag gtacctggag gaacactcgg cccagcaggg ggatcttata tgggaggatg    3060
cactgttcat gttttgagtat tttaagccca agacccttcc tgaatttgac agctataaga    3120
ccagcaccgt gtctgctgac ttggccaacc tactgaagag aattgccacc attgtgcctc    3180
gcacagagag gccagccctt agcctggaca aagtctctgc ctacattgag ggaacttcaa    3240
ctgaggtacc ctgcctccca gagggggctg accctccc tccagtggtg aacgagcttt      3300
actacctcct ggctgattat catttcaaaa acaaggagca gtccaaggcc atcaagttct    3360
acatgcatga catctgcatc tgccccaata ggtttgattc ctgggcaggc atggctctgg    3420
```

-continued

```
cccgggccag ccgcattcag gacaagctga actccaatga gctgaagagt gatgggccca    3480
tttggaagca tgccacgccc gtcttgaact gcttccgtcg ggccctggag attgacagct    3540
ccaacttgtc cctatggatt gagtatggca ccatgtccta tgccttgcac tcattcgcct    3600
cacgtcaatt gaagcagtgg agaggcgagc tgcccctga gctcgtgcag cagatggagg      3660
gccggcgcga cagcatgcta gagacagcca agcactgttt cacatcagca gcccgctgcg    3720
agggtgatgg tgacgaggag gagtggctca tccactacat gctgggcaag gtggctgaga    3780
agcagcagca gccacccacc gtttacttgc tgcactacag gcaggctggc cactacctgc    3840
acgaggaggc tgcccgctac cccaagaaga tccactacca caacccacct gagctggcca    3900
tggaggccct ggaggtgtac tttcggctcc atgcttccat cctgaagctc ctggggaagc    3960
ccgattctgg ggttggtgca gaggtcctgg tcaactttat gaaggaggct gcagaaggac    4020
cctttgccag gggcgaggag aagaacacac ccaaagcttc agaaaaggag aaggcctgcc    4080
tggtggacga ggactccac tcttcagctg gacactgcc gggccccgga gcctccctcc      4140
cctcctcctc tggcccaggt ctgacatccc caccttacac agccactccg attgaccacg    4200
attacgtcaa atgtaaaaaa ccccaccagc aggcaacgcc ggacgaccga agccaggaca    4260
gcacagccgt agcactctca gactctagct caacgcagga cttctttaat gagcccacca    4320
gcttactgga aggctccagg aaatcctaca cagagaagag gctgcccatt ctcagttccc    4380
aagcaggagc gacgggtaaa gatcttcagg gggccacaga agaaagagga aaaacgagg     4440 agtcattgga gagtacagaa ggcttccggg ctgcagagca aggtgtccag aagcctgctg    4500
cagaaacccc agcctctgct tgcatccctg gcaagccctc agcatccaca cccaccctgt    4560
gggatgggaa gaagagaggg gacctcccag gggagccagt ggccttcccc caggggctgc    4620
cggctggtgc tgaggagcag cggcagtttc tcacagagca gtgcatcgcc tccttccgcc    4680
tgtgcctgag ccgcttcccc cagcactata agagtctcta ccgtctggcc ttcctctaca    4740
cctacagcaa gacccaccgg aacctccagt gggcccgcga cgtgttgcta ggcagcagta    4800
tcccgtggca acaactgcag cacatgccgg cacagggct cttctgcgag aggaacaaga     4860
ccaatttctt caacggcatc tggcggatcc ccgtggacga gattgaccgg ccgggcagct    4920
ttgcctggca catgaaccgc tccatcgtgc tgctgctcaa ggtgctggcc cagctgcggg    4980
accacagcac cctgctgaag gtgtcctcca tgcttcagcg gacccagac cagggcaaga     5040 agtatctgcg agatgctgac cgccaggtcc tggcgcagcg ggccttcatc ctcactgtga    5100
aggtgctcga agacacgctg agcgagctcg cagaggggtc agaacgccca gggcccaagg    5160
tctgtggcct cccccggagcc aggatgacca ccgatgtctc acacaaggcc agtcctgagg   5220
atggccagga gggcctcccc cagccgaaga agccccctct ggctgatggc tcagggccag    5280
ggcccgagcc aggaggcaaa gtgggcctcc tcaaccaccg gcctgtggcc atggatgcag    5340
gagacagtgc agaccaaagc ggggagcgga aggataaaga gagcccacgg gcagggccca    5400
ctgagcccat ggacacgagt gaggccactg tttgccactc agacttggag cggacaccac    5460
ccctgctgcc aggtcgcccc gcaagggacc ggggccccga gagccggccc actgagctgt    5520
ccctggagga gctgagcatc agtgcccggc agcagcccac cccgctcacc ccagcccagc    5580
cagcccccgc cccgcccccc gccaccacca gggaccag ggcaggggc caccggagg        5640 agccgctctc ccgctcagc cgcaagagga agctcctgga ggacagagag tcaggcaaga    5700
cacttctgtt ggatgcctac cgtgtgtggc agcagggcca gaagggtgtg gcctatgacc    5760
```

-continued

```
tgggccgtgt ggagaggatc atgtcggaga cctacatgct catcaagcag gtggatgagg    5820
aggctgcgct ggagcaggct gtgaagttct gccaggtcca tcttgggct gccgcccaga    5880 gacaggcctc gggggacacc cccaccactc aaagcaccc caaagacagc cgagagaact    5940
tctttcctgt gacagtggtg cccacagccc ctgaccctgt gccagctgac tctgtccagc    6000
ggcccagtga tgctcacacc aagcctcgcc ctgcactagc tgccgccaca actattatca    6060
cctgccctcc gtcagcatca gcttccaccc tggaccagtc caaggaccct gggcctcccc    6120
ggccacacag gcctgaagct acccccagca tggcctctct gggcccagag ggagaagagc    6180
tggcgagagt ggcagagggc accagcttcc cgcctcagga gccacggcac agtccgcagg    6240
tgaagatggc cccacaagt tccccggcag agccacactg ctggccggca gaggctgccc    6300
tgggcacagg cgctgagccc acctgcagcc aggagggaa actgaggcct gagccgagaa    6360
gggatgggga ggctcaggag gctgcgagtg agactcagcc cctgagctct cccccaacag    6420
ctgccagctc caaggccccc agcagtggga gtgcccagcc accagaggt cacccaggca    6480 agcctgagcc cagccgggct aagtcccgcc cctgcccaa catgccaaag ctggtcatcc    6540
cctccgccgc caccaagttc ccccctgaga tcaccgtcac gccacccacc caaccctgc    6600 tctcccccaa aggcagcatc tcggaggaga ccaagcagaa gctgaagtca gccatccttt    6660
ctgcccagtc tgctgccaac gtgaggaagg agagcctatg ccagccagcc ctggaggtcc    6720
tggagacatc cagccaggag tcctcgctgg agcgagac agacgaggac gacgactaca    6780
tggacatttg aggggccact gcagcccac cgccacgccc caggggacca gccaggcctg    6840
gaatgccccc tggcaggac cctgggcagg accagaggcc acatggatg ccactcccca    6900 cacagccccc aggcctgccc agcccacctc ctcatggcat cctccctgta cccaggtcag    6960
gctgtccaca ccacatggga gcccagagga ggaggggccc gccttagcca tgtgaaggtg    7020
gattggtcgc catctgcacg ccaggcggca tccttttcta tgaagtgttg actttgtaaa    7080
tctgcccaca cccagctggc catatccacc cctcgacgcc gggatgagcc ggctctgcct    7140
gtgtcacagt ggaggggtcc tttagggcca ggctcacccc tcacccttt tttggttgct    7200 tttctaataa agatggaaca gtt                                           7223
```

<210> SEQ ID NO 9
<211> LENGTH: 552
<212> TYPE: DNA
<213> ORGANISM: Homo sapiens

<400> SEQUENCE: 9

```
caggtgaaga tggcccccac aagttccccg gcagagccac actgctggcc ggcagaggct      60
gccctgggca caggcgctga gcccacctgc agccaggagg ggaaactgag gcctgagccg     120
agaagggatg ggaggctca ggaggctgcg agtgagactc agcccctgag ctctccccca     180
acagctgcca gctccaaggc ccccagcagt gggagtgccc agccaccaga gggtcaccca     240
ggcaagcctg agcccagccg ggctaagtcc cgccccctgc ccaacatgcc aaagctggtc     300
atcccctccg ccgccaccaa gttcccccct gagatcaccg tcacgccacc caccccaacc     360
ctgctctccc ccaaaggcag catctcggag gagaccaagc agaagctgaa gtcagccatc     420
ctttctgccc agtctgctgc caacgtgagg aaggagagcc tatgccagcc agccctggag     480
gtcctggaga catccagcca ggagtcctcg ctggagagcg agacagacga ggacgacgac     540
tacatggaca tt                                                        552
```

<210> SEQ ID NO 10
<211> LENGTH: 504
<212> TYPE: DNA
<213> ORGANISM: Homo sapiens

<400> SEQUENCE: 10

| | | | | | |
|---|---|---|---|---|---|
| gcagaggctg | ccctgggcac | aggcgctgag | cccacctgca | gccaggaggg | gaaactgagg | 60 |
| cctgagccga | gaagggatgg | ggaggctcag | gaggctgcga | gtgagactca | gcccctgagc | 120 |
| tctcccccaa | cagctgccag | ctccaaggcc | cccagcagtg | ggagtgccca | gccaccagag | 180 |
| ggtcacccag | gcaagcctga | gcccagccgg | gctaagtccc | gccccctgcc | caacatgcca | 240 |
| aagctggtca | tcccctccgc | cgccaccaag | ttcccccctg | agatcaccgt | cacgccaccc | 300 |
| accccaaccc | tgctctcccc | caaaggcagc | atctcggagg | agaccaagca | gaagctgaag | 360 |
| tcagccatcc | tttctgccca | gtctgctgcc | aacgtgagga | aggagagcct | atgccagcca | 420 |
| gccctggagg | tcctggagac | atccagccag | gagtcctcgc | tggagagcga | gacagacgag | 480 |
| gacgacgact | acatggacat | ttga | | | | 504 |

<210> SEQ ID NO 11
<211> LENGTH: 294
<212> TYPE: DNA
<213> ORGANISM: Homo sapiens

<400> SEQUENCE: 11

| | | | | | |
|---|---|---|---|---|---|
| gctaagtccc | gccccctgcc | caacatgcca | aagctggtca | tcccctccgc | cgccaccaag | 60 |
| ttcccccctg | agatcaccgt | cacgccaccc | accccaaccc | tgctctcccc | caaaggcagc | 120 |
| atctcggagg | agaccaagca | gaagctgaag | tcagccatcc | tttctgccca | gtctgctgcc | 180 |
| aacgtgagga | aggagagcct | atgccagcca | gccctggagg | tcctggagac | atccagccag | 240 |
| gagtcctcgc | tggagagcga | gacagacgag | gacgacgact | acatggacat | ttga | 294 |

<210> SEQ ID NO 12
<211> LENGTH: 237
<212> TYPE: DNA
<213> ORGANISM: Homo sapiens

<400> SEQUENCE: 12

| | | | | | |
|---|---|---|---|---|---|
| aagttccccc | ctgagatcac | cgtcacgcca | cccacccccaa | ccctgctctc | ccccaaaggc | 60 |
| agcatctcgg | aggagaccaa | gcagaagctg | aagtcagcca | tcctttctgc | ccagtctgct | 120 |
| gccaacgtga | ggaaggagag | cctatgccag | ccagccctgg | aggtcctgga | gacatccagc | 180 |
| caggagtcct | cgctggagag | cgagacagac | gaggacgacg | actacatgga | catttga | 237 |

<210> SEQ ID NO 13
<211> LENGTH: 69
<212> TYPE: DNA
<213> ORGANISM: Homo sapiens

<400> SEQUENCE: 13

| | | | | | |
|---|---|---|---|---|---|
| ttcccccctg | agatcaccgt | cacgccaccc | accccaaccc | tgctctcccc | caaaggcagc | 60 |
| atctcggag | | | | | | 69 |

<210> SEQ ID NO 14
<211> LENGTH: 39
<212> TYPE: DNA
<213> ORGANISM: Homo sapiens

<400> SEQUENCE: 14

-continued ttcccccctg agatcaccgt cacgccaccc accccaacc    39

<210> SEQ ID NO 15
<211> LENGTH: 6663
<212> TYPE: DNA
<213> ORGANISM: Homo sapiens

<400> SEQUENCE: 15

```
atgattcgaa ttgcagcctt aaatgccagc tccaccattg aggatgatca tgaaggaagc    60
tttaaaagtc acaaaaccca gacaaaggag gctcaggaag cagaggcttt tgcattgtac   120
cacaaggccc ttgatctgca gaaacatgac cggtttgagg agtctgccaa agcctaccat   180
gagctcttgg aggcgagcct gctgcgggag gcagtttcat ccggtgatga aaagagggg    240
ttgaaacacc ctgggctgat actgaaatat cccacttata agaacttggc ccagctggca   300
gcccagcggg aggatctgga gacagccatg gagttctact tagaggcagt gatgctggac   360
tccacagatg tcaacctctg gtataagatt ggacatgtgg ccctgaggct catccggatc   420
cccctggctc gccatgcttt tgaggaaggg ctgcggtgca atcctgacca ctggccctgt   480
ttggataacc taatcactgt cctgtacacc ctcagtgatt acacaacatg tctgtacttc   540
atctgcaaag ctttggagaa ggattgccgg tacagcaaag ggctggtcct caaggagaag   600
atttttgagg agcagccttg tctccggaag gactctctca gaatgttcct caaatgtgac   660
atgtcgattc acgatgtttc ggtgagtgca gctgagacac aggcgattgt agatgaggcc   720
ttggggctgc gaaaaagag gcaagcgctg attgtgcggg agaaggagcc ggacctgaaa   780
cttgtgcagc ccattccttt cttcacctgg aagtgcctcg agagagctt gctggccatg    840
tacaatcatc tcaccacctg tgaccccca cgtcccagcc ttggcaaaag gattgatttg   900
tcggactacc aggaccccag ccagcctctt gagtcctcca tggtggtgac gccagttaac   960
gtgatccagc aagcactgtc agcaccaac ccagctgtgg ctgtcgccga gcctgtggtc   1020
tcctacacct ctgtggctac aaccagcttc ccactgcaca gtcctggtct gttggagaca   1080
ggcgctcctg tgggtgatat ttctggggga gataaatcca agaaagggt aaaacgaag    1140
aagatttcag aagagagtgg agaaacagca agcggcggt ctgcccgtgt ccgaaacacc   1200
aagtgcaaaa agaagagaa agtagacttc caggagcttc tgatgaagtt cttgccgtcc   1260
aggttaagaa agctggaccc tgaggaggaa gatgattcct ttaataacta tgaagtccag   1320
tcagaagcca aactggaaag cttcccaagc attgggcctc aaaggctgtc atttgactca   1380
gccacattca tggaatctga aaagcaggac gtgcatgagt tcctgctgga aacctaacc   1440
aacgggggca tcctggagct gatgatgcgc tacctgaaag ccatgggcca aagttcttg   1500
gtaaggtggc ctccaggctt ggcggaggtc gtgctcagcg tctaccacag ctggaggagg   1560
cacagcacca gcctgccaa cccgctgctg agggactgca gcaacaagca catcaaggac   1620
atgatgctga tgtctctctc ctgcatggaa ctccagctgg accagtggct gctgaccaaa   1680
ggcagaagct ctgcagtgtc tcctcggaac tgccctgctg gtatggtgaa tggcagattt   1740
ggacctgact tcccagggac ccactgcctg ggtgacctcc tacagctgtc atttgcctcg   1800
tcccagcgcg acctgttcga ggatggttgg ctggagtttg tggtccgtgt ttactggctg   1860
aaggctcgct tcctggcgct gcagggagac atggagcagg ccctggagaa ctatgacatc   1920
tgcacagaaa tgctccagag ttccaccgcc atccaggtgg aggcagggc tgaacgaaga   1980
gacattgtca tccggctgcc caacctccat aatgactctg tggtttccct ggaggagatt   2040
gataagaacc tgaagtcgct ggagcggtgc cagtccctgg aggagattca gcggctgtat   2100
```

```
gaagcaggcg actacaaggc tgttgtgcat ctgctccgcc ccactttgtg caccagtggg    2160
tttgaccggg ccaaacacct ggagtttatg acttccattc ctgagaggcc agcccagctg    2220
cttcttctgc aggactcctt gctccggctg aaggactatc ggcagtgttt tgagtgttcc    2280
gatgtggctc tgaacgaggc tgtccagcag atggtgaact caggtgaggc tgccgccaag    2340
gaggagtggg tggccacagt gacccaactg ctgatgggca tcgagcaggc cctctctgcg    2400
gacagcagtg gtagcatcct gaaggtatca tcctccacca ctggccttgt gcggctcacc    2460
aacaacctca tccaggtcat tgactgcagc atggctgtgc aggaggaggc caaggagccc    2520
cacgtctctt cagtgctacc ctggatcatt ctacaccgga tcatctggca ggaggaagac    2580
accttccatt ctctgtgcca ccagcagcag ctccaaaacc cagcggagga agggatgtca    2640
gagacgccca tgctcccatc ctccctcatg ctgctgaaca cagcccacga gtatttgggc    2700
agaaggtcct ggtgctgcaa ttcagatggg gctctgctgc gattctatgt gcgagtactc    2760
cagaaggaac tggctgcatc cacctctgaa gacacgcacc cttacaagga ggagctggag    2820
acagccttgg agcagtgctt ctactgcctg tacagcttcc ccagcaagaa gagtaaggcc    2880
aggtacctgg aggaacactc ggcccagcag gtggatctta tgggagga tgcactgttc      2940 atgtttgagt attttaagcc caagacccct cctgaatttg acagctataa gaccagcacc    3000
gtgtctgctg acttggccaa cctactgaag agaattgcca ccattgtgcc tcgcacagag    3060
aggccagccc ttagcctgga caaagtctct gcctacattg agggaacttc aactgaggta    3120
ccctgcctcc cagaggggggc tgaccctcc cctccagtgg tgaacgagct ttactacctc    3180
ctggctgatt atcatttcaa aaacaaggag cagtccaagg ccatcaagtt ctacatgcat    3240
gacatctgca tctgccccaa taggtttgat tcctgggcag gcatggctct ggcccgggcc    3300
agccgcattc aggacaagct gaactccaat gagctgaaga gtgatgggcc catttggaag    3360
catgccacgc ccgtcttgaa ctgcttccgt cgggcctgg agattgacag ctccaacttg      3420
tccctatgga ttgagtatgg caccatgtcc tatgccttgc actcattcgc ctcacgtcaa    3480
ttgaagcagt ggagaggcga gctgcccct gagctcgtgc agcagatgga gggccggcgc      3540
gacagcatgc tagagacagc caagcactgt tcacatcag cagcccgctg cgagggtgat       3600
ggtgacgagg aggagtggct catccactac atgctgggca aggtggctga aagcagcag      3660 cagccaccca ccgtttactt gctgcactac aggcaggctg ccactacct gcacgaggag       3720 gctgcccgct acccccaaga ggatccactac cacaaccccac ctgagctggc catggaggcc    3780
ctggaggtgt actttcggct ccatgcttcc atcctgaagc tcctggggaa gcccgattct    3840
ggggttggtg cagaggtcct ggtcaactt atgaaggagg ctgcagaagg accctttgcc      3900 agggcgagg agaagaacac acccaaagct tcagaaaagg agaaggcctg cctggtggac      3960
gaggactccc actcttcagc tgggacactg ccggggcccg gagcctccct ccctcctcc      4020 tctggcccag gtctgacatc cccaccttac acagccactc cgattgacca cgattacgtc    4080
aaatgtaaaa aaccccacca gcaggcaacg ccggacgacc gaagccagga cagcacagcc    4140
gtagcactct cagactctag ctcaacgcag gacttcttta atgagcccac cagcttactg    4200
gaaggctcca ggaaatccta cacagagaag aggctgccca ttctcagttc ccaagcagga    4260
gcgacgggta agatcttca ggggccaca gaagaaagag gaaaaaacga ggagtcattg       4320
gagagtacaa aaggcttccg ggctgcagag caaggtgtcc agaagcctgc tgcagaaacc    4380
ccagcctctg cttgcatccc tggcaagccc tcagcatcca cacccaccct gtgggatggg    4440
```

-continued

| | | | | |
|---|---|---|---|---|
| aagaagagag | gggacctccc | aggggagcca | gtggccttcc | cccagggct gccggctggt | 4500 |
| gctgaggagc | agcggcagtt | tctcacagag | cagtgcatcg | cctccttccg cctgtgcctg | 4560 |
| agccgcttcc | cccagcacta | taagagtctc | taccgtctgg | ccttcctcta cacctacagc | 4620 |
| aagacccacc | ggaacctcca | gtgggcccgc | gacgtgttgc | taggcagcag tatcccgtgg | 4680 |
| caacaactgc | agcacatgcc | ggcacagggg | ctcttctgcg | agaggaacaa gaccaatttc | 4740 |
| ttcaacggca | tctggcggat | ccccgtggac | gagattgacc | ggccgggcag ctttgcctgg | 4800 |
| cacatgaacc | gctccatcgt | gctgctgctc | aaggtgctgg | cccagctgcg ggaccacagc | 4860 |
| accctgctga | aggtgtcctc | catgcttcag | cggaccccag | accagggcaa gaagtatctg | 4920 |
| cgagatgctg | accgccaggt | cctggcgcag | cgggccttca | tcctcactgt gaaggtgctc | 4980 |
| gaagacacgc | tgagcgagct | cgcagagggg | tcagaacgcc | cagggcccaa ggtctgtggc | 5040 |
| ctccccggag | ccaggatgac | caccgatgtc | tcacacaagg | ccagtcctga ggatggccag | 5100 |
| gagggcctcc | cccagccgaa | gaagcccccct | ctggctgatg | gctcagggcc agggcccgag | 5160 |
| ccaggaggca | aagtgggcct | cctcaaccac | cggcctgtgg | ccatggatgc aggagacagt | 5220 |
| gcagaccaaa | gcggggagcg | gaaggataaa | gagagcccac | gggcagggcc cactgagccc | 5280 |
| atggacacga | gtgaggccac | tgtttgccac | tcagacttgg | agcggacacc accctgctg | 5340 |
| ccaggtcgcc | ccgcaaggga | ccggggcccc | gagagccggc | ccactgagct gtccctggag | 5400 |
| gagctgagca | tcagtgcccg | gcagcagccc | accccgctca | ccccagccca gccagccccc | 5460 |
| gccccgccc  | ccgccaccac | cacagggacc | agggcagggg | gccacccgga ggagccgctc | 5520 |
| tcccggctca | gccgcaagag | gaagctcctg | gaggacacag | agtcaggcaa gacacttctg | 5580 |
| ttggatgcct | accgtgtgtg | gcagcagggc | cagaaggtg  | tggcctatga cctgggccgt | 5640 |
| gtggagagga | tcatgtcgga | gacctacatg | ctcatcaagc | aggtggatga ggaggctgcg | 5700 |
| ctggagcagg | ctgtgaagtt | ctgccaggtc | catcttgggg | ctgccgccca gagacaggcc | 5760 |
| tcggggaca  | cccccaccac | tccaaagcac | cccaaagaca | gccgagagaa cttctttcct | 5820 |
| gtgacagtgg | tgcccacagc | ccctgaccct | gtgccagctg | actctgtcca gcggcccagt | 5880 |
| gatgctcaca | ccaagcctcg | ccctgcacta | gctgccgcca | caactattat cacctgccct | 5940 |
| ccgtcagcat | cagcttccac | cctggaccag | tccaaggacc | ctgggcctcc ccggccacac | 6000 |
| aggcctgaag | ctaccccag  | catggcctct | ctgggcccag | agggagaaga gctggcgaga | 6060 |
| gtggcagagg | gcaccagctt | cccgcctcag | gagccacggc | acagtccgca ggtgaagatg | 6120 |
| gcccccacaa | gttccccggc | agagccacac | tgctggccgg | cagaggctgc cctgggcaca | 6180 |
| ggcgctgagc | ccacctgcag | ccaggagggg | aaactgaggc | ctgagccgag aagggatggg | 6240 |
| gaggctcagg | aggctgcgag | tgagactcag | cccctgagct | ctcccccaac agctgccagc | 6300 |
| tccaaggccc | ccagcagtgg | gagtgccag  | ccaccagagg | gtcacccagg caagcctgag | 6360 |
| cccagccggg | ctaagtcccg | ccccctgccc | aacatgccaa | agctggtcat ccctccgcc  | 6420 |
| gccaccaagt | tccccctga  | gatcaccgtc | acgccaccca | ccaacccct gctctccccc | 6480 |
| aaaggcagca | tctcggagga | gaccaagcag | aagctgaagt | cagccatcct ttctgcccag | 6540 |
| tctgctgcca | acgtgaggaa | ggagagccta | tgccagccag | ccctggaggt cctggagaca | 6600 |
| tccagccagg | agtcctcgct | ggagagcgag | acagacgagg | acgacgacta catggacatt | 6660 |
| tga | | | | | 6663 |

US 6,686,450 B1

IMMUNOSUPPRESSIVE AGENTS THAT INHIBIT CALCINEURIN FUNCTION AND USES OF THESE AGENTS

CROSS-REFERENCE TO RELATED APPLICATION

This application claims the benefit of U.S. Provisional Application No. 60/089,786 filed Jun. 18, 1998.

The U.S. Government has a paid-up license in this invention and the right in limited circumstances to require the patent owner to license others on reasonable terms as provided for by the terms of Grant No. RO1-GM 55783 awarded by the National Institutes of Health.

FIELD OF THE INVENTION

This invention relates generally to novel immunosuppressive agents that inhibit calcineurin function, methods for identifying immunosuppressive agents, and treatments for immune system related diseases and conditions.

BACKGROUND OF THE INVENTION

While immune reactions are required to protect animals from deleterious foreign antigens, certain immune reactions can result in pathological conditions, e.g., autoimmune disease, allergies, transplant graft rejection and graft-versus-host disease.

Calcineurin plays a pivotal role in the T cell receptor (TCR)-mediated signal transduction pathway, leading to the transcriptional activation of certain cytokines, e.g., IL-2, which are required for an immune response. Calcineurin is a calcium and calmodulin-dependent protein serine/threonine phosphatase. Calcineurin has been shown to modulate the activity of several transcription factors that bind to the IL-2 promoter, including NF-AT, NF-κB and AP-1. It has been reported that calcineurin dephosphorylates the cytoplasmic subunit of NF-AT, allowing it to translocate into the nucleus to activate transcription.

The immunosuppressive drugs cyclosporin A and FK506 target calcineurin, inhibiting its protein phosphatase activity. These drugs, however, can exhibit nephrotoxic and neurotoxic effects after long term usage. There is a need for additional immunosuppressive agents which can inhibit calcineurin function.

SUMMARY OF THE INVENTION

It is an object of the invention to provide a novel immunosuppressive agent.

It is another object of the invention to provide a novel immunosuppressive agent that binds to calcineurin.

It is yet another object of the invention to provide a novel immunosuppressive agent that inhibits interaction between calcineurin and NF-AT.

It is yet another object of the invention to provide a method for inhibiting an immune reaction using a novel immunosuppressive agent that inhibits calcineurin function.

According to the invention, an isolated polypeptide, called Cabin 1, comprising the amino acid sequence as set forth in SEQ ID NO:1, or biologically active analogs thereof, is provided. In certain embodiments, the Cabin 1 polypeptide, or biologically active analogs thereof, is capable of binding to calcineurin and/or inhibiting calcineurin function.

Another aspect of the invention is an isolated polypeptide fragment of Cabin 1 polypeptide which is capable of binding to calcineurin and/or inhibiting calcineurin function, or biologically active analogs thereof. In preferred embodiments, the polypeptide fragment of Cabin 1 is a C-terminal fragment of the Cabin 1 polypeptide. For example, the invention includes fragments comprising the amino acid sequence as set forth in SEQ ID NO:2 (Cabin 1–54), SEQ ID NO:3 (Cabin 1–6), SEQ ID NO: 4 (Cabin 1–97) and SEQ ID NO:5 (Cabin 1–14). Other preferred fragments include SEQ ID NO:6 (Cabin 1-CNBD23) and SEQ ID NO:7 (Cabin1-CNBD 13).

Another aspect of the invention is an isolated polynucleotide comprising a polynucleotide encoding the polypeptide comprising the amino acid sequence as set forth in SEQ ID NO:1, SEQ ID NO:2, SEQ ID NO:3, SEQ ID NO: 4, SEQ ID NO: 5, SEQ ID NO: 6 or SEQ ID NO: 7, or biologically active analogs thereof. In certain embodiments, the polynucleotide comprises the nucleotide sequence as set forth in SEQ ID NO: 8, SEQ ID NO:9, SEQ ID NO: 10, SEQ ID NO: 11, SEQ ID NO: 12, SEQ ID NO:13, SEQ ID NO: 14 or SEQ ID NO: 15.

Another aspect of the invention is a gene therapy vector comprising a nucleotide sequence encoding Cabin 1 polypeptide or a fragment thereof capable of binding to calcineurin or inhibiting calcineurin function, or a biologically active analog thereof. In certain preferred embodiments, the fragment is a C-terminal fragment of Cabin 1.

Another aspect of the invention is a cell having a gene therapy vector described herein.

Another aspect of the invention is a method for producing a polypeptide capable of binding to calcineurin and/or inhibiting calcineurin function, comprising culturing a cell having a gene therapy vector described herein under conditions that permit expression of the polypeptide.

Another aspect of the invention is a method for treating an immune-related disease or condition in an animal. A gene therapy vector described herein is administered to the animal.

Another aspect of the invention is a method for inhibiting an immune response in an animal. An animal in need of inhibition of an immune response is provided. A therapeutically effective amount of a Cabin 1 polypeptide or a fragment thereof capable of binding to calcineurin or inhibiting calcineurin function, or a biologically active analog thereof, is provided. In certain preferred embodiments, the fragment is a C-terminal fragment of Cabin 1. The polypeptide or fragment, or biologically active analog thereof, is administered to the animal so as to inhibit the immune response in the animal. In certain embodiments, the polypeptide comprises the amino acid sequence as set forth in SEQ ID NO: 1, SEQ ID NO: 2, SEQ ID NO: 3, SEQ ID NO: 4, SEQ ID NO: 5, SEQ ID NO: 6, SEQ ID NO: 7, or biologically active analogs thereof.

Another aspect of the invention is a composition for treating an immune-related disease or condition in an animal comprising a therapeutically effective amount of Cabin 1 polypeptide or a fragment thereof capable of binding to calcineurin or inhibiting calcineurin function, or a biologically active analog thereof, and a pharmaceutically acceptable carrier.

Another aspect of the invention is a composition for treating an immune-related disease or condition in an animal, comprising a therapeutically effective amount of a recombinant nucleic acid having a nucleotide sequence encoding Cabin 1 polypeptide or a fragment thereof capable of binding to calcineurin or inhibiting calcineurin function, or a biologically active analog thereof, and a pharmaceutically acceptable carrier.

Another aspect of the invention is a method of inhibiting protein phosphatase activity by calcineurin. Calcineurin and a substrate, e.g., NF-AT, for calcineurin phosphatase activity are provided. Cabin 1 polypeptide or a fragment thereof capable of inhibiting protein phosphatase activity by calcineurin, or a biologically active analog thereof, is provided. The calcineurin and polypeptide or fragment, or biologically active analog thereof, are contacted such that the protein phosphatase activity by the calcineurin on the substrate is inhibited. In certain embodiments, the inhibiting is in vitro. In certain embodiments, the inhibiting is in vivo Another aspect of the invention is a method for identifying an agent that is immunosuppressive. A cell is provided. An agent, e.g., a fragment of Cabin 1 polypeptide, a biologically active analog thereof, or a mimetic thereof, is provided. The agent is contacted with the cell. The effect of the agent on an aspect of calcineurin function in the cell is evaluated. A change in the aspect of calcineurin function is indicative of the agent being immunosuppresive. In certain preferred embodiments, the aspect of calcineurin function is protein phosphatase activity, e.g., dephosphorylation of NF-AT. In certain preferred embodiments, the aspect of calcineurin function is binding of calcineurin to Cabin 1 polypeptide or a fragment thereof.

Another aspect of the invention is a method for identifying an agent that is immunosuppresive. Calcineurin and NF-AT are provided. An agent, e.g., a fragment of Cabin 1 polypeptide, a biologically active analog thereof, or a mimetic thereof, is provided. The agent is contacted with the calcineurin. The effect of the agent on dephosphorylation of the NF-AT by the calcineurin is evaluated. A change in the dephosphorylation is indicative of the agent being immunosuppressive.

Another aspect of the invention is a method for evaluating an agent for use in treating a disease involving an immune reaction resulting in pathology. A cell, cell-free system or animal is provided. An agent is provided. The agent is administered to the cell, cell-free system or animal in a therapeutically effective amount. The effect of the agent on an aspect of Cabin 1 metabolism is evaluated. A change in the aspect of Cabin 1 metabolism is indicative of the usefulness of the agent in treating a disease involving an immune reaction resulting in pathology.

Another aspect of the invention is an isolated antibody, e.g., monoclonal or polyclonal, which selectively binds to an antigenic determinant of a polypeptide having the amino acid sequence as set forth in SEQ ID NO: 1, SEQ ID NO: 2, SEQ ID NO: 3, SEQ ID NO: 4, SEQ ID NO: 5, SEQ ID NO: 6 or SEQ ID NO: 7.

The above and other features, objects and advantages of the present invention will be better understood by a reading of the following specification in conjunction with the drawings.

BRIEF DESCRIPTION OF THE DRAWINGS

FIG. 1D is a schematic representation of overlapping clones of Cabin1 (SEQ ID NO: 8) identified from the yeast two-hybrid screen.

FIG. 2A depicts the amino acid sequence of the putative full length Cabin1 (SEQ ID NO: 1). Highlighted are: a putative coiled coil domain (bold); putative nuclear localization sequences (boxed) (244–247, 378–381, and 1841–1848); PEST sequences (underlined); and a putative SH3 binding site (boxed). The N-termini of the four Cabin1 (SEQ ID NO: 1) clones (154, 6, 97, and 14) isolated by the yeast two-hybrid screen are highlighted.

FIG. 3E is a graph of a Western blot showing that coimmunoprecipitation of Cabin1–14 (SEQ ID NO: 5) and wild type calcineurin β2 is dependent on both PKC and calcium stimulation.

FIG. 7A–7F depicts the full length Cabin1 cDNA sequence (SEQ ID NO:8).

FIG. 8A–8G depicts the Cabin1 cDNA coding sequence (SEQ ID NO:15).

FIG. 9A–9C depicts the putative full length Cabin1 polypeptide sequence (SEQ ID NO:1).

FIG. 10 depicts the Cabin1–154 cDNA sequence (SEQ ID NO:9).

FIG. 11 depicts the Cabin1–154 polypeptide sequence (SEQ ID NO:2).

FIG. 12 depicts the Cabin1–6 cDNA sequence (SEQ ID NO:10).

FIG. 13 depicts the Cabin1–6 polypeptide sequence (SEQ ID No:3).

FIG. 14 depicts the Cabin1–97 cDNA sequence (SEQ ID NO:11).

FIG. 15 depicts the Cabin1–97 polypeptide sequence (SEQ ID NO:4).

FIG. 16 depicts the Cabin1–14 cDNA sequence (SEQ ID NO:12).

FIG. 17 depicts the Cabin1–14 polypeptide sequence (SEQ ID:NO:5).

FIG. 18 depicts the Cabin1-CNBD23 cDNA sequence (SEQ ID NO:13).

FIG. 19 depicts the Cabin1-CNBD23 polypeptide sequence (SEQ ID NO:6).

FIG. 20 depicts the Cabin1-CNBD13 cDNA sequence (SEQ ID NO:14).

FIG. 21 depicts the Cabin1-CNBD13 polypeptide sequence (SEQ ID NO:7).

DETAILED DESCRIPTION OF CERTAIN PREFERRED EMBODIMENTS

Figure 1A:
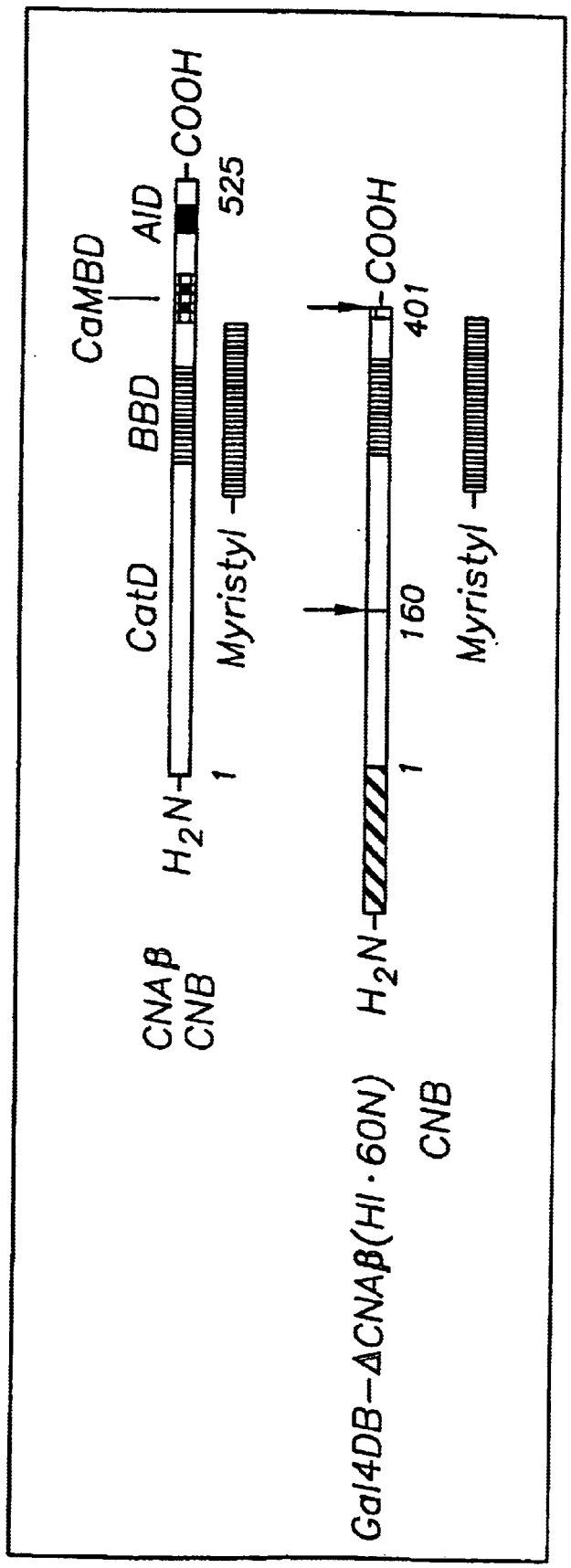
FIG. 1A is a schematic diagram of wild type calcineurin and the H160N mutant used as bait in the yeast two-hybrid screen for calcineurin interacting proteins. The leftmost arrow in the lower portion of the figure indicates the site of the H160N mutation (replacement of H by N at position 160). The rightmost arrow in the lower portion of the figure indicates the site of truncation at residue 401 of wild type calcineurin so as to remove the C-terminal portion including the autoinhibitory domain and most of the calmodulin binding domain.

This invention provides an isolated polypeptide, called Cabin 1, comprising the amino acid sequence as set forth in SEQ ID NO: 1, or biologically active analogs thereof. See FIGS. 2A and 9.

The terms polypeptides, proteins and peptides are used interchangeably herein. In certain embodiments, the Cabin 1 polypeptide or biologically active analogs thereof, are capable of binding to calcineurin, preferably activated calcineurin. Calcineurin is a calmodulin-dependent, cyclosporin A/FK506-sensitive, phosphatase. Calcineurin can be activated through its interaction with $Ca^{+2}$ activated calmodulin when intracellular calcium levels are elevated as a result of receptor crosslinking and phospholipase C activation. The activated calcineurin in turn can activate NF-AT protein from an inactive cytoplasmic pool. By NF-AT protein (nuclear factor of activated T cells) is meant a member of a family of transcription factors comprising the members NF-AT1, NF-AT2, NF-AT3 and NF-AT4, with several isoforms. Any other NF-AT proteins whose activation is calcineurin dependent is also meant to be included. NF-AT proteins can be expressed in immune cells, e.g., T lymphocytes, and play a role in eliciting immune responses. NF-AT activation includes protein-protein interaction between calcineurin and NF-AT, dephosphorylation of NF-AT by calcineurin, and translocation of NF-AT to the nucleus. NF-AT activation in turn results in induction of NF-AT dependent gene expression of, e.g., cytokine genes, e.g., IL-2, IL-3, IL-4, TNF-α and INF-γ, during the immune response.

In certain embodiments, the Cabin 1 polypeptide, or biologically active analogs thereof, are capable of inhibiting calcineurin function. Calcineurin function includes, e.g., protein phosphatase activity, e.g., dephosphorylation of NF-AT, or activation of NF-κB or AP-1. In certain embodiments, the Cabin 1 polypeptide, or biologically active analogs thereof, are capable of inhibiting transcriptional activation of calcineurin-responsive elements, e.g., certain cytokine genes, e.g., IL-2, IL-3, IL4, TNF-α or INF-γ. The Cabin 1 polypeptide thus can be used as an immunosuppressive agent.

Cabin 1 polypeptide can be obtained, e.g., from purification or secretion of a naturally occurring Cabin 1 polypeptide, from recombinant Cabin 1 polypeptide, or from synthesized Cabin 1 polypeptide.

The invention also includes an isolated polypeptide which is at least about 70%, 80%, 90%, 95%, 97%, 98% or 99%, homologous to the amino acid sequence as set forth in SEQ ID No:1, and which is capable of inhibiting calcineurin function.

The invention also includes an isolated polypeptide which is at least about 70%, 80%, 90%, 95%, 97%, 98% or 99%, homologous to the amino acid sequence as set forth in SEQ ID NO: 1, and which is capable of binding to calcineurin.

By X% homologous is meant the maximal percent homology obtained by aligning the first amino acids of the polypeptide with any amino acid in the amino acid sequence that it is being compared to, e.g., SEQ ID NO:1, and then scoring the homology of aligned amino acids for each amino acid in the polypeptide without introduction of any gaps.

The invention also includes an isolated polypeptide comprising an amino acid sequence of at least about 5, 10, 15, 20, 25, 30 or 35 consecutive amino acid residues from the amino acid sequence as set forth in SEQ ID NO: 1, and which is capable of binding to calcineurin and/or which is capable of inhibiting calcineurin function.

The invention also includes a polypeptide produced by a method comprising expressing a nucleic acid encoding the amino acid sequence as set forth in SEQ ID NO: 1, and recovering the polypeptide.

The invention also includes an isolated polypeptide fragment of Cabin 1 polypeptide which is capable of binding to calcineurin and/or inhibiting calcineurin function, or biologically active analogs thereof.

By fragment of Cabin 1 polypeptide is meant some portion of the naturally Cabin 1 polypeptide. Preferably, the fragment is less than about 200 amino acid residues, more preferably is less than about 150 amino acid residues, more preferably yet is less than about 100 amino acid residues, more preferably yet is less than about 50 amino acid residues, more preferably yet is less than about 30 amino acid residues, more preferably yet is less than about 20 amino acid residues, more preferably yet is less than about 10 amino acid residues, and most preferably is less than about 6 amino acid residues in length. Preferably, the fragment is greater than about 3 amino acid residues, more preferably is greater than about 5 amino acid residues in length. Fragments include, e.g., truncated secreted forms, cleaved fragments, proteolytic fragments, splicing fragments, other fragments, and chimeric constructs between at least a portion of the relevant gene and another molecule. Fragments of the Cabin 1 polypeptide can be generated by methods known to those skilled in the art. In preferred embodiments, the fragment is biologically active. The ability of a candidate fragment to exhibit a biological activity of the Cabin 1 polypeptide can be assessed, e.g., by its ability to bind to calcineurin, or its ability to inhibit calcineurin function, by methods, e.g., as described herein. Also included in the invention are fragments containing residues that are not required for biological activity of the fragment or that result from alternative mRNA splicing or alternative protein processing events.

Fragments of a protein can be produced by any of a variety of methods known to those skilled in the art, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNAs which encode an array of fragments. DNAs which encode fragments of a protein can also be generated, e.g., by random shearing, restriction digestion, chemical synthesis of oligonucleotides, amplification of DNA using the polymerase chain reaction, or a combination of the above-discussed methods.

Fragments can also be chemically synthesized using techniques known in the art, e.g., conventional Merrifield solid phase f-Moc or t-Boc chemistry. For example, peptides of the present invention can be arbitrarily divided into fragments of desired length with no overlap of the fragments, or divided into overlapping fragments of a desired length.

In preferred embodiments, the polypeptide fragment of Cabin 1 which is capable of binding to calcineurin or inhibiting calcineurin function is a C-terminal fragment of the Cabin 1 polypeptide. For example, the invention includes fragments comprising the amino acid sequence as set forth in SEQ ID NO: 2 (Cabin 1–54), SEQ ID NO: 3 (Cabin 1–6), SEQ ID NO: 4 (Cabin 1–97) and SEQ ID NO: 5 (Cabin 1–14). Other preferred fragments include SEQ ID NO:6 (Cabin 1-CNBD23) and SEQ ID NO: 7 (Cabin 1-CNBD13). See FIGS. 2A, 11, 13, 15, 17, 19 and 21.

By a biologically active analog of the Cabin 1 polypeptide or fragment is meant an analog that is capable of binding to calcineurin and/or inhibiting calcineurin function. The ability to assess biological activity of the analog can be determined by methods, e.g., as described herein.

By analog is meant a compound that differs from the naturally occurring Cabin 1 polypeptide or fragment in amino acid sequence or in ways that do not involve sequence, or both. Peptide analogs of the invention generally exhibit at least about 70% homology, preferably at least about 80% homology, more preferably at least about 90% homology, more preferably yet at least about 95% homology, more preferably yet at least about 97% homology, more preferably yet at least about 98% homology, and most preferably at least about 99% homology, with substantially the entire sequence of the naturally occurring Cabin 1 polypeptide or fragment, preferably with a segment of about 200 amino acid residues, more preferably with a segment of about 150 amino acid residues, more preferably yet with a segment of about 100 amino acid residues, more preferably yet with a segment of about 50 amino acid residues, more preferably yet with a segment of about 30 amino acid residues, more preferably yet with a segment of about 20 amino acid residues, more preferably yet with a segment of about 10 amino acid residues, and more preferably with a segment of about 5 amino acid residues, of the Cabin 1 polypeptide or fragment.

In certain preferred embodiments, the analog is an isolated peptide which is at least about 70%, 80%, 90%, 95%, 97%, 98% or 99% homologous to the amino acid sequence as set forth in SEQ ID NO:2, SEQ ID NO:3, SEQ ID NO:4, SEQ ID NO:5, SEQ ID NO:6 or SEQ ID NO:7, and which is capable of binding to calcineurin and/or inhibiting calcineurin function.

Non-sequence modifications include, e.g., in vivo or in vitro chemical derivatizations of the Cabin 1, polypeptide or fragment. Non-sequence modifications include, e.g., changes in phosphorylation, acetylation, methylation, carboxylation, or glycosylation. Methods for making such modifications are known to those skilled in the art. For example, phosphorylation can be modified by exposing the peptide to phosphorylation-altering enzymes, e.g., kinases or phosphatases.

Preferred analogs include a Cabin 1 polypeptide or fragment whose sequence differs from the wild-type sequence by one or more conservative amino acid substitutions or by one or more non-conservative amino acid substitutions, deletions, or insertions, which do not abolish biological activity of the polypeptide. Conservative substitutions typically include the substitution of one amino acid for another with similar characteristics, e.g., substitutions within the following groups: valine, glycine; glycine; alanine; valine; isoleucine, leucine; aspartic acid, glutamic acid; asparagine, glutamine, serine, threonine; lysine, arginine; and phenylalanine, tyrosine. Other examples of conservative substitutions are shown in Table 1.

TABLE 1

CONSERVATIVE AMINO ACID SUBSTITUTIONS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Histidine | H | D-His |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tryptophan | W | D-Trp, Phe, D-Phe, Tyr, D-Tyr |
| Tyrosine | Y | D-Tyr, Phe, D-Phe, L-Dopa, His, D-His |
| Valine | V | D-Val, Leu, D-Leu, Ile, D-Ile, Met, D-Met |

Amino acid sequence variants of a protein can be prepared by any of a variety of methods known to those skilled in the art. For example, random mutagenesis of DNA which encodes a protein or a particular domain or region of a protein can be used, e.g., PCR mutagenesis (using, e.g., reduced Taq polymerase fidelity to introduce random mutations into a cloned fragment of DNA; Leung et al., Bio-Technique 1:11–15 (1989)), or saturation mutagenesis (by, e.g., chemical treatment or irradiation of single-stranded DNA in vitro, and synthesis of a complementary DNA strand; Mayers et al., Science 229:242 (1985)). Random mutagenesis can also be accomplished by, e.g., degenerate oligonucleotide generation (using, e.g., an automatic DNA synthesizer to chemically synthesize degenerate sequences; Narang, Tetrahedron 39:3 (1983); Itakura et al., Recombinant DNA, Proc. 3rd Cleveland Sympos. Macromolecules, ed. A. G. Walter, Amsterdam: Elsevier, pp. 273–289 (1981)). Non-random or directed mutagenesis can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (i) substituting first with conserved amino acids and then with more radical choices depending upon results achieved, (ii) deleting the target residue, (iii) inserting residues of the same or a different class adjacent to the located site, or (iv) combinations of the above.

Methods for identifying desirable mutations include, e.g., alanine scanning mutagenesis (Cunningham and Wells, Science 244:1081-1-85 (1989)), oligonucleotide-mediated mutagenesis (Adelman et al., DNA 2:183 (1983)), cassette mutagenesis (Wells et al., Gene 34:315 (1985)), combinatorial mutagenesis, and phage display libraries (Ladner et al., PCT International Appln. No. WO88/06630). The Cabin 1 polypeptide or fragment analogs can be tested in physical and/or functional assays, e.g., in their ability to bind to calcineurin or to inhibit calcineurin function, as described herein.

Other analogs within the invention include, e.g., those with modifications which increase peptide stability. Such analogs can contain, e.g., one or more non-peptide bonds (which replace the peptide bonds) in the peptide sequence. Also included are, e.g., analogs that include residues other than naturally occurring L-amino acids, e.g., D-amino acids or non-naturally occurring or synthetic amino acids, e.g., β or γ amino acids and cyclic analogs.

Analogs are also mean to include peptides in which structural modifications have been introduced into the peptide backbone so as to make the peptide non-hydrolyzable. Such peptides are particularly useful for oral administration, as they are not digested. Peptide backbone modifications include, e.g., modifications of the amide nitrogen, the α-carbon, the amide carbonyl, or the amide bond, and modifications involving extensions, deletions or backbone crosslinks. For example, the backbone can be modified by substitution of a sulfoxide for the carbonyl, by reversing the peptide bond, or by substituting a methylene for the carbonyl group. Such modifications can be made by standard procedures known to those skilled in the art. See, e.g., Spatola, A. F., "Peptide Backbone Modifications: A Structure-Activity Analysis of Peptides Containing Amide Bond Surrogates, Conformational Constraints, and Related Backbone Replacements," in Chemistry and Biochemistry of Amino Acids, Peptides and Proteins, Vol. 7, pp. 267–357, B. Weinstein (ed.), Marcel Dekker, Inc., New York (1983).

An analog is also meant to include polypeptides in which one or more of the amino acid residues include a substituent group, or polypeptides which are fused with another compound, e.g., a compound to increase the half-life of the polypeptide, e.g., polyethylene glycol.

Analogs are also meant to include those produced by introduction of amino acid substitutions, or the design of constrained polypeptides, cyclic polypeptides, and other modified polypeptides or analogs, where the modifications or constraints are introduced on the basis of knowledge of the conformation of the polypeptide bound to calcineurin. The conformation of the bound polypeptide can be determined by techniques known to those skilled in the art, e.g., NMR, e.g., transferred nuclear Overhauser effect spectroscopy (transferred NOESY) of a rapidly dissociating peptide to determine distance constraints (Campbell and Sykes, J. Magn. Reson. 93:77–92 (1991); Lian et al., Methods Enzymol. 239:657–700 (1994)), with or without additional NMR techniques, followed by the use of the distance constraints and of constrained molecular dynamics simulations and energy minimization with available computer software (e.g., the NMR_Refine module of the InsightII™ suite of programs (Biosym/MSI, San Diego, Calif.), and the Discover™ or Discover 3.0™ molecular simulation programs (Biosym/MSI, San Diego, Calif.) to arrive at a structural model. Alternatively, the structure of the specified complexes can be determined by x-ray crystallography.

The invention also includes an isolated polynucleotide comprising a polynucleotide encoding the polypeptide comprising the amino acid sequence as set forth in SEQ ID NO: 1, or biologically active analogs thereof.

The terms polynucleotide, nucleotide and oligonucleotide are used interchangeably herein. By a polynucleotide encoding a polypeptide is meant a polynucleotide which includes only coding sequence for the polypeptide, as well as a polynucleotide which includes additional coding sequences, e.g., a leader, secretory or proprotein sequence, and/or non-coding sequences, e.g., introns or non-coding sequences 5' and/or 3' of the coding sequence for the mature polypeptide. The polynucleotides of the invention are also meant to include polynucleotides in which the coding sequence for the mature polypeptide is fused in the same reading frame to a polynucleotide sequence which aids in expression and/or secretion of a polypeptide from a host cell, e.g., a leader sequence. The polynucleotides are also meant to include polynucleotides in which the coding sequence is fused in frame to a marker sequence which, e.g., allows for purification of the polypeptide.

In certain embodiments, the polynucleotide comprises the nucleotide sequence as set forth in SEQ ID NO: 8. See FIG. 7. In certain embodiments, the polynucleotide is capable of hybridizing to and is at least about 70%, 80%, 90%, 95%, 97%, 98% or 99% identical to the nucleotide sequence as set forth in SEQ ID NO:8, and encodes a polypeptide having biological activity. By percent identity is meant the maximal percent identity obtained by aligning the first base of the polynucleotide with any base in the nucleotide sequence and then scoring the identity of aligned bases for each base in the polynucleotide without introduction of any gaps.

In certain embodiments, the polynucleotide comprises the nucleotide sequence as set forth in SEQ ID NO: 15. See FIG. 8. In certain embodiments, the polynucleotide is capable of hybridizing to and is at least about 70%, 80%, 90%, 95%, 97% 98% or 99% identical to the nucleotide sequence as set forth in SEQ ID NO:15, and encodes a polypeptide having biological activity.

The invention also includes an isolated polynucleotide comprising a polynucleotide encoding the polypeptide comprising the amino acid sequence as set forth in SEQ ID NO:2, SEQ ID NO:3, SEQ ID NO: 4, SEQ ID NO: 5, SEQ ID NO: 6, SEQ ID NO:7, or biologically active analogs thereof. In certain embodiments, the polynucleotide comprises the nucleotide sequence as set forth in SEQ ID NO:9, SEQ ID NO:10, SEQ ID NO:11, SEQ ID NO:12, SEQ ID NO: 13 or SEQ ID NO: 14. See FIGS. 10, 12, 14, 16, 18 and 20. In certain embodiments, the polynucleotide is capable of hybridizing to and is at least about 70%, 80%, 90%, 95%, 97%, 98% or 99% identical to the nucleotide sequence as set forth in SEQ ID NO:9, SEQ ID NO:10, SEQ ID NO:11, SEQ ID NO:12, SEQ ID NO: 13 or SEQ ID NO: 14, and which encodes a polypeptide having biological activity.

The invention also includes an isolated polynucleotide comprising a nucleotide sequence of about 9 to about 24, about 25 to about 42, or about 43 to about 60, consecutive nucleotides as set forth in SEQ ID NO: 8, wherein the polynucleotide encodes a polypeptide capable of binding to calcineurin and/or inhibiting calcineurin function.

The nucleotide sequences of the present invention can be in the form of, e.g., RNA, DNA or PNA, e.g., cRNA, cDNA, genomic DNA, or e.g., synthetic RNA, DNA or PNA. The nucleotide sequence can be double-stranded or single stranded, and if single stranded can be the coding strand or non-coding (anti-sense) strand.

The coding sequence which encodes the peptide fragments can be identical to the coding sequences as set forth above, or can be a different coding sequence, which coding sequence, as a result of the redundancy or degeneracy of the genetic code, encodes the same peptide fragments as the nucleic acids as set forth above.

The invention also includes a gene therapy vector comprising a nucleotide sequence encoding Cabin 1 polypeptide or a fragment thereof capable of binding to calcineurin or inhibiting calcineurin function, or a biologically active analog thereof. In certain preferred embodiments, the fragment is a C-terminal fragment of Cabin 1.

By a gene therapy vector is meant a vector useful for gene therapy. Gene therapy vectors carry a gene of interest that is useful for gene therapy. The gene therapy vectors are able to be transferred to the cells of an animal, e.g., a human, and are able to express the gene of interest in such cells so as to effect gene therapy. The vector can be, e.g., chromosomal, non-chromosomal or synthetic. It can be, e.g., RNA or DNA. The vector can be, e.g., a plasmid, a virus or a phage. Preferred vectors include, e.g., retroviral vectors, adenoviral vectors, adeno-associated vectors, herpes virus vectors and Semliki Forest virus vector. A preferred retroviral vector is Murine Stem Cell Virus (MSCV), which is a variant of Moloney Murine Leukemia Virus (MoMLV).

In preferred embodiments, the gene therapy vector comprises a nucleotide sequence encoding the polypeptide comprising the amino acid sequence as set forth in SEQ ID NO: 1, SEQ ID NO:2, SEQ ID NO:3, SEQ ID NO:4, SEQ ID NO:5, SEQ ID NO:6, SEQ ID NO:7, or biologically active analogs thereof. The invention also includes nucleotide sequences which are capable of hybridizing to and which are at least about 70%, 80%, 90%, 95%, 97%, 98% or 99% identical to these nucleotide sequences, and which encode a polypeptide having biological activity.

In certain embodiments, the gene therapy vector has a nucleotide sequence encoding a tag for identification of the Cabin 1 polypeptide or fragment thereof, and/or a selectable marker, and/or an inducible promoter, and/or a cell-specific promoter.

The invention also includes a cell having a gene therapy vector described herein. Preferably, the cell is an animal cell. The gene therapy vectors described herein can be introduced into a cell, e.g., by transformation, transfection, transduction, infection, or ex vivo injection. Preferably, they are targeted to a particular cell type or cell.

The invention also includes a method for producing a polypeptide capable of binding to calcineurin and/or inhibiting calcineurin function, comprising culturing a cell having a gene therapy vector described herein under conditions that permit expression of the polypeptide.

The invention also includes a method for treating an immune-related disease or condition in an animal. A gene therapy vector described herein is administered to the animal.

Treating is meant to include, e.g., preventing, treating, reducing the symptoms of, or curing the disease or condition.

Immune-related diseases or conditions include, e.g., abnormal activity of the immune system, a transplant graft rejection, and graft-versus-host disease. Abnormal activity of the immune system is meant to include, e.g., acute immune diseases, chronic immune diseases and autoimmune diseases. Examples include asthma, allergies, rheumatoid arthritis, inflammatory bowel disease, aplastic anemia, psoriasis, lupus, erythematosus, inflammatory disease, type I diabetes, pulmonary fibrosis, scleroderma, dermatomyositis, Sjogren's syndrome, postpericardiotomy syndrome, Kawasaki disease, Hashimoto's thyroiditis, Graves' disease, myasthenia gravis, pemphigus vulgaris, autoimmune hemolytic anemia, idiopathic thromboyctopenia, chronic glomerulonephritis, Goodpasture's syndrome, Wegener's granulomatosis, multiple sclerosis, cystic fibrosis, chronic relapsing hepatitis, primary biliary cirrhosis, uveitis, allergic rhinitis, allergic conjunctivitis, atopic dermatitis and autoimmune thyroiditis. Transplant graft rejection is meant to include, e.g., allogeneic or xenogeneic transplantation of organs, tissues or cells, e.g., bone marrow or stems cells. Graft-versus-host disease can result, e.g., from bone marrow or stem cell transplantation.

The invention also includes a method for inhibiting an immune response in an animal. An animal in need of inhibition of an immune response is provided. A therapeutically effective amount of a Cabin 1 polypeptide or a fragment thereof capable of binding to calcineurin or inhibiting calcineurin function, or a biologically active analog thereof, is provided. In certain preferred embodiments, the fragment is a C-terminal fragment of Cabin 1. The polypeptide or fragment, or biologically active analog thereof, is administered to the animal so as to inhibit the immune response in the animal.

An animal in need of inhibition of an immune response is meant to include an animal having, or being at risk of having, an immune related disease or condition, e.g., abnormal activity of the immune system, a transplant graft rejection, or graft-versus-host disease. Being at risk for the disease or condition can result from, e.g., a family history of the disease, a genotype which predisposes to the disease, or phenotypic systems which predispose to the disease.

The polypeptide fragment can be, e.g., any of the polypeptide fragments of the invention described herein. In certain embodiments, the polypeptide comprises the amino acid sequence as set forth in SEQ ID NO:1, SEQ ID NO:2, SEQ ID NO:3, SEQ ID NO:4, SEQ ID NO:5, SEQ ID NO:6, SEQ ID NO:7, or biologically active analogs thereof.

In certain embodiments, the therapeutically effective amount of the polypeptide or fragment, or biologically active analog thereof, is provided by providing to the animal a recombinant nucleic acid having a nucleotide sequence encoding the polypeptide or fragment, or a biologically active analog thereof, and which is capable of expressing the polypeptide or fragment, or biologically active analog thereof, in vivo. The peptide fragment is administered to the animal by administering the recombinant nucleic acid. The nucleic acid can be, e.g., any of the polynucleotides described herein. In certain embodiments, the recombinant nucleic acid is a gene therapy vector, e.g., as described herein.

In certain embodiments, the therapeutically effective amount of the polypeptide or fragment, or biologically active analog thereof, is provided by providing to the animal a composition comprising animal cells wherein a recombinant nucleic acid having a nucleotide sequence encoding the polypeptide or fragment, or biologically active analog thereof, has been introduced ex vivo into the animal cells so as to express the polypeptide or fragment, or biologically active analog thereof, in the animal cells. The polypeptide fragment is administered to the animal by administering the animal cells having the recombinant nucleic acid. Preferably, the recombinant nucleic acid is a gene therapy vector, e.g., as described herein. Preferably, the animal cells are derived from the animal to be treated or allogeneic cells.

Administration of an agent, e.g., a polypeptide or nucleic acid can be accomplished by any method which allows the agent to reach the target cells. These methods include, e.g., injection, deposition, implantation, suppositories, oral ingestion, inhalation, topical administration, or any other method of administration where access to the target cells by the agent is obtained. Injections can be, e.g., intravenous, intradermal, subcutaneous, intramuscular or intraperitoneal. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral injection doses can be enterically coated. Inhalation includes administering the agent with an aerosol in an inhalator, either alone or attached to a carrier that can be absorbed. The agent can be suspended in liquid, e.g., in dissolved or colloidal form. The liquid can be a solvent, partial solvent or non-solvent. In many cases, water or an organic liquid can be used.

In certain embodiments of the invention, the administration can be designed so as to result in sequential exposures to the agent over some time period, e.g., hours, days, weeks, months or years. This can be accomplished by repeated administrations of the agent, e.g., by one of the methods described above, or alternatively, by a controlled release delivery system in which the agent is delivered to the animal over a prolonged period without repeated administrations. By a controlled release delivery system is meant that total release of the agent does not occur immediately upon administration, but rather is delayed for some time. Release can occur in bursts or it can occur gradually and continuously. Administration of such a system can be, e.g., by long acting oral dosage forms, bolus injections, transdermal patches or subcutaneous implants. Examples of systems in which release occurs in bursts include, e.g., systems in which the agent is entrapped in liposomes which are encapsulated in a polymer matrix, the liposomes being sensitive to a specific stimulus, e.g., temperature, pH, light, magnetic field, or a degrading enzyme, and systems in which the agent is encapsulated by an ionically-coated microcapsule with a microcapsule core-degrading enzyme. Examples of systems in which release of the agent is gradual and continuous include, e.g., erosional systems in which the agent is contained in a form within a matrix, and diffusional system in which the agent permeates at a controlled rate, e.g., through a polymer. Such sustained release systems can be, e.g., in the form of pellets or capsules.

The agents can be administered prior to or subsequent to the appearance of disease symptoms. In certain embodiments, the agent is administered to patients with familial histories of the disease, or who have phenotypes that may indicate a predisposition to the disease, or who have been diagnosed as having a genotype which predisposes the patient to the disease, or who have other risk factors.

The agent is administered to the animal in a therapeutically effective amount. By therapeutically effective amount is meant that amount which is capable of at lest partially preventing or reversing the disease. A therapeutically effective amount can be determined on an individual basis and will be based, at least in part, on consideration of the species of animal, the animal's size, the animal's age, the efficacy of the particular agent used, the longevity of the particular agent used, the type of delivery system used, the time of administration relative to the onset of disease symptoms, and whether a single, multiple, or controlled release dose regimen is employed. A therapeutically effective amount can be determined by one of ordinary skill in the art employing such factors and using no more than routine experimentation.

In certain preferred embodiments, the concentration of the agent if it is a polypeptide is at a dose of about 0.1 to about 1000 mg/kg body weight/day, more preferably at about 0.1 to about 500 mg/kg/day, more preferably yet at about 0.1 to about 10 mg/kg/day, and most preferably at about 0.1 to about 100 mg/kg/day. Preferably, the dosage form is such that it does not substantially deleteriously affect the animal.

In certain embodiments, a therapeutically effective amount of an agent which is a polypeptide an be administered by providing to the animal a nucleic acid encoding the polypeptide and expressing the polypeptide in vivo. Preferably, the dosage form is such that it does not substantially deleteriously affect the animal. Nucleic acids encoding the polypeptide can be administered in any biologically effective carrier, e.g. any formulation or composition capable of effectively delivering the nucleotide sequence for the polypeptide to cells in vivo. Approaches include, e.g., insertion of the nucleic acid into viral vectors, including, e.g. retrovirus, adenovirus, adeno-associated virus, herpes virus and Semliki Forest virus vectors. Viral vectors can be delivered to the cells, e.g., by infection or transduction using the virus. Viral vectors can also be delivered to the cells, e.g., by physical means, e.g., by electroporation, lipids, cationic lipids, liposome, DNA gun, $Ca_3(PO_4)_2$ precipitation, or delivery of naked DNA. In certain preferred embodiments, the virus is administered by injection, e.g., intramuscular injection, in a dose range of about $10^3$ to about $10^{10}$ infectious particles per injection per treatment, more preferably in a dose range of about $10^5$ to about $10^8$ infectious particles per injection per treatment. Single or multiple doses can be administered over a given period of time, depending, e.g., upon the disease. An alternative is insertion of the nucleic acid encoding the peptide into a bacterial or eukaryotic plasmid. Plasmid DNA can be delivered to cells with the help of, e.g., cationic liposomes (lipofectin™; Life Technologies, Inc., Gaithersburg, Md.) or derivatized (e.g., antibody conjugated) polylysine conjugates, gramicidin S, streptolysin O, artificial viral envelopes or other such carriers or delivery aids, as well as direct injection of the gene construct or $Ca_3(PO_4)_2$ precipitation carried out in vivo, or by use of a gene gun. The above-described methods are known to those skilled in the art and can be performed without undue experimentation.

In certain embodiments, the nucleic acid is administered to the animal by introducing ex vivo the nucleic acid into cells of the animal or allogeneic cells, and administering the cells having the nucleic acid to the animal. Any cell type can be used. In certain embodiments, the cells having the introduced nucleic acid are expanded and/or selected after the nucleic acid transfer. The cells having the transferred nucleic acid are subsequently administered to the animal. Preferably, the cells are administered to the animal in a dose range of about $1\times10^6$ to about $1\times10^9$ cells/dosage/treatment, and most preferably at about $1\times10^7$ to about $1\times10^8$ cells/dosage/treatment. The cells can be administered by any method which results in delivering the transferred nucleic acid in the cells to the desired target. For example, the cells can be implanted directly into a specific tissue of the animal, or implanted after encapsulation within an artificial polymer matrix.

Choice of the particular delivery system will depend on such factors as the intended target and the route of administration, e.g., locally or systemically. Targets for delivery of the agent can be, e.g., specific target cells which are causing or contributing to disease. Administration can be directed to one or more cell types, and to one or more subsets of cells within a cell type, so as to be therapeutically effective, by methods known to those skilled in the art. For example, the agent can be coupled to an antibody, to a liquid, to a cell surface receptor, or to a toxin component, or can be contained in a particle which is selectively internalized into cells, e.g., liposomes, or a virus where the viral receptor binds specifically to a certain cell type, or a viral particle lacking the viral nucleic acid, or can be administered by local injection. In certain embodiments, administration is done in a prenatal animal or embryonic cell.

In certain embodiments, other therapy is additionally administered. For example, another therapeutic agent, chemotherapy, radiation or surgery, is additionally administered to the animal, either simultaneously or at different times.

The invention also includes a composition for treating an immune-related disease or condition in an animal comprising a therapeutically effective amount of Cabin 1 polypeptide or a fragment thereof capable of binding to calcineurin or inhibiting calcineurin function, or a biologically active analog thereof, and a pharmaceutically acceptable carrier. The polypeptide fragment can be, e.g., any of the fragments described herein. In certain preferred embodiments, the fragment is a C-terminal fragment of Cabin 1. In certain embodiments, the composition is a pharmaceutical composition. Pharmaceutically acceptable carriers include, e.g., water, saline, dextrose, glycerol, ethanol, liposomes and lipid emulsions.

The invention also includes a composition for treating an immune-related disease or condition in an animal, comprising a therapeutically effective amount of a recombinant nucleic acid having a nucleotide sequence encoding Cabin 1 polypeptide or a fragment thereof capable of binding to calcineurin or inhibiting calcineurin function, or a biologically active analog thereof, and a pharmaceutically acceptable carrier. In certain preferred embodiments, the fragment is a C-terminal fragment of Cabin 1. The nucleic acid can be e.g., any of the polynucleotides described herein. In certain embodiments, the composition is a pharmaceutical composition.

The invention also includes a method for inhibiting protein phosphatase activity by calcineurin. Calcineurin and a substrate for calcineurin phosphates activity are provided. Cabin 1 polypeptide or a fragment thereof capable of inhibiting protein phosphatase activity by calcineurin, or a biologically active analog thereof, is provided. The calcineurin and polypeptide or fragment, or biologically active analog thereof, are contacted such that the protein phosphatase activity by the calcineurin on the substrate is inhibited. In certain embodiments, the inhibiting is in vitro. In certain embodiments, the inhibiting is in vivo. In certain preferred embodiments, the fragment is a C-terminal fragment of Cabin 1. A preferred substrate is NF-AT.

The invention also includes a method for identifying an agent that is immunosuppressive. A cell is provided. An agent, e.g., a fragment of Cabin 1 polypeptide, a biologically active analog thereof, or a mimetic thereof, is provided. The agent is contacted with the cell. The effect of the agent on an aspect of calcineurin function in the cell is evaluated. A change in the aspect of calcineurin function is indicative of the agent being immunosuppressive. In certain preferred embodiments, the aspect of calcineurin function is protein phosphatase activity, e.g., dephosphorylation of NF-AT. In certain preferred embodiments, the aspect of calcineurin function is binding of calcineurin to Cabin 1 polypeptide or a fragment thereof.

By cell is meant a cell or a group of cells, or a cell that is part of an animal. The cell can be a human or non-human cell. Cell is also meant to include a transgenic cell.

By mimetic is meant a molecule which resembles in shape and/or charge distribution of Cabin 1. The mimetic can be a peptide or a non-peptide. By employing, e.g., scanning mutagenesis, e.g., alanine scanning mutagenesis, linker scanning mutagenesis or saturation mutagenesis, to map the amino acid residues of a particular Cabin 1 polypeptide involved in binding a binding molecule, peptide mimetics, e.g., diazopine or isoquinoline derivatives, can be generated which mimic those residues in binding to a binding molecule, and which therefore can inhibit binding of the Cabin 1 to a binding molecule and thereby interfere with the function of Cabin 1. For example, non-hydrolyzable peptide analogs of such residues can be generated using benzodiazepine (See, e.g., Freidinger et al., in Peptides: Chemistry and Biology, G. R. Marshall ed., ESCOM Publisher: Leiden, Netherlands (1988)); azepine See, e.g., Huffman et al., in Peptides: Chemistry and Biology, G. R. Marshall ed., ESCOM Publisher: Leiden, Netherlands (1988)) substituted gamma lactam rings (See, e.g., Garvey et al., in Peptides: Chemistry and Biology, G. R. Marshall ed., ESCOM Publisher: Leiden, Netherlands (1988)); keto-methylene pseudopeptides (See, e.g., Ewenson et al., J. Med. Chem. 29:295 (1986); Ewenson et al., in Peptides: Structure and Function (Proceedings of the 9th American Peptide Symposium) Pierce Chemical Co. Rockland, Ill. (1985)); β-turn dipeptide cores (See, e.g., Nagai et al., Tetrahedron Lett. 26:647 (1985); Sato et al., J. Chem. Soc. Perkin Trans. 1:1231 (1986)); or β-aminoalcohols (See, e.g., Gordon et al., Biochem. Biophys. Res. Commun. 126:419 (1985)); Dann et al., Biochem. Biophys. Res. Commun. 134:71 (1986)).

The invention also includes a method for identifying an agent that is immunosuppressive. Calcineurin and NF-AT are provided. An agent, e.g., a fragment of Cabin 1 polypeptide, a biologically active analog thereof, or a mimetic thereof, is provided. The agent is contacted with the calcineurin. The effect of the agent on dephosphorylation of the NF-AT by the calcineurin is evaluated. A change in the dephosphorylation is indicative of the agent being immunosuppressive.

The invention also includes a method for evaluating an agent for use in treating a disease involving an immune reaction resulting in pathology. A cell, cell-free system or animal is provided. An agent is provided. The agent is administered to the cell, cell-free system or animal in a therapeutically effective amount. The effect of the agent on an aspect of Cabin 1 metabolism is evaluated. A change in the aspect of Cabin 1 metabolism is indicative of the usefulness of the agent in treating a disease involving an immune reaction resulting in pathology.

By Cabin 1 metabolism is meant any aspect of the production, release, expression, function, action, interaction or regulation of Cabin 1. These aspects are meant to include e.g., temporal, site or distribution aspects. The metabolism of Cabin 1 includes modifications e.g., covalent or non-covalent modifications of Cabin 1 polypeptide, or covalent or non-covalent modifications that Cabin 1 induces in other substances. Any aspect of Cabin 1 metabolism can be evaluated. In certain embodiments, as aspect of Cabin 1 structure, e.g., gene or protein structure, is evaluated.

The invention also includes an isolated antibody, e.g., monoclonal or polyclonal, which selectively binds to an antigenic determinant of a polypeptide having the amino acid sequence as set forth in SEQ ID NO:1, SEQ ID NO:2, SEQ ID NO:3, SEQ ID NO:4, SEQ ID NO:5, SEQ ID NO:6 or SEQ ID NO:7.

The following non-limiting examples further illustrate the present invention.

EXAMPLES

Example 1

Identification of Cabin 1 as a Calcineurin Binding Protein Using the Yeast Two-Hybrid System This example illustrates the use of the year two-hybrid system to identify proteins that interact with calcineurin.

A catalytically inactive calcineurin mutant was used as an affinity probe, reasoning that it would associate with substrates more stably than the wild type enzyme, as has been demonstrated for protein tyrosine phosphatases (Sun et al., Cell 75:487–493 (1993); Furukawa, T., J. NIH Res. 7:52–53 (1995)). Through site-directed mutagenesis of residues at the putative active site of calcineurin, a number of mutants were isolated which were catalytically inactive but retained structural integrity as judged by their interactions with the FKBP-FK506 complex (Mondragon et al., Biochemistry 36:4934–4942 (1997)). One such mutant was H 160N, a mutant of the β2 isoform of calcineurin, the predominant isoform in T lymphocytes (Jiang et al., Mol. Immunol., 34:663–669 (1997). When expressed in T cells, this mutant was found to be dominant negative, blocking PMA and ionomycin-stimulated IL-2 promoter activation by over 60%. The H160-N mutant was chosen as the bait in the yeast two-hybrid system (Fields and Song, Nature 340:245–246 (1989); Durfee et al., Genes Dev. 7:555–569 (1993)), to identify its substrates and binding proteins.

To alleviate the dependence of full length calcineurin on calcium in yeast, the C-terminal autoinhibitory domain and most of the calmodulin building domain were removed from the catalytic submit in the calcineurin bait. See FIG. 1A which depicts schematic diagrams of wild type calcineurin and the HI 60N mutant used as bait. Abbreviations used are: CN, calcineurin; CNB, calcineurin B; CatD, catalytic domain; BBD, CNB binding domain; CaMBD, calmodulin binding domain; AID, autoinhibitory domain. To validate this strategy, a fish plasmid was constructed encoding a fusion protein between the N-terminal domain of NF-AT1 and the Gal4 activation domain, and was tested to determine whether the fusion protein interacted with the calcineurin bait in the two-hybrid system. Significant activation of the LacZ reporter gene was observed in yeast expressing the calcineurin bait and NF-AT fish fusion proteins, indicating that the use of the catalytically inactive mutant of calcineurin was fruitful for identifying its substrates and interacting proteins in the yeast two-hybrid system.

Cabin 1 cDNA fragments were isolated by a yeast two-hybrid screen of a mouse T cell cDNA library (Elledge et al., Proc. Natl. Acad. Sci. USA 88:1731–1735 (1991)). The bait plasmid was constructed by the insertion of a cDNA fragment encoding the first 410 amino acids of CNβ2 with the H160N mutation into the BamHI and XhoI sites in pAS2 (Jain et al., Nature 365:352–355 (1993)), to give pAS-CNβ2m. Subsequently, an expression cassette of CNB under the control of yeast ADH promoter was inserted into a blunted SacI site of pAS-CNβ2m. The calcineurin bait plasmid was transformed into the yeast strain Y190 (Elledge et al., Proc. Natl. Acad. Sci. USA 88:1731–1735 (1991)), followed by transformation with the mouse T cell cDNA library (Elledge et al., Proc. Natl. Acad. Sci. USA 88:1731–1735 (1991)). The transformed yeast were selected on dropout plates (His, Leu, Trp) with 50 mM 3-Amino-1, 2,4-triazole. Positive colonies were picked 5 days after plating and streaked onto X-gal (Leu, Trp) plates. Colonies that turned blue overnight were further subjected to liquid β-gal assay to confirm the LacZ reporter gene expression. Upon screening 1.6 million independent transformants from the mouse T cell cDNA library (Elledge et al., Proc. Natl. Acad. Sci. USA 88:1731–1735 (1991)), six clones were identified which exhibited significant activation of the LacZ reporter gene.

Figure 1B:
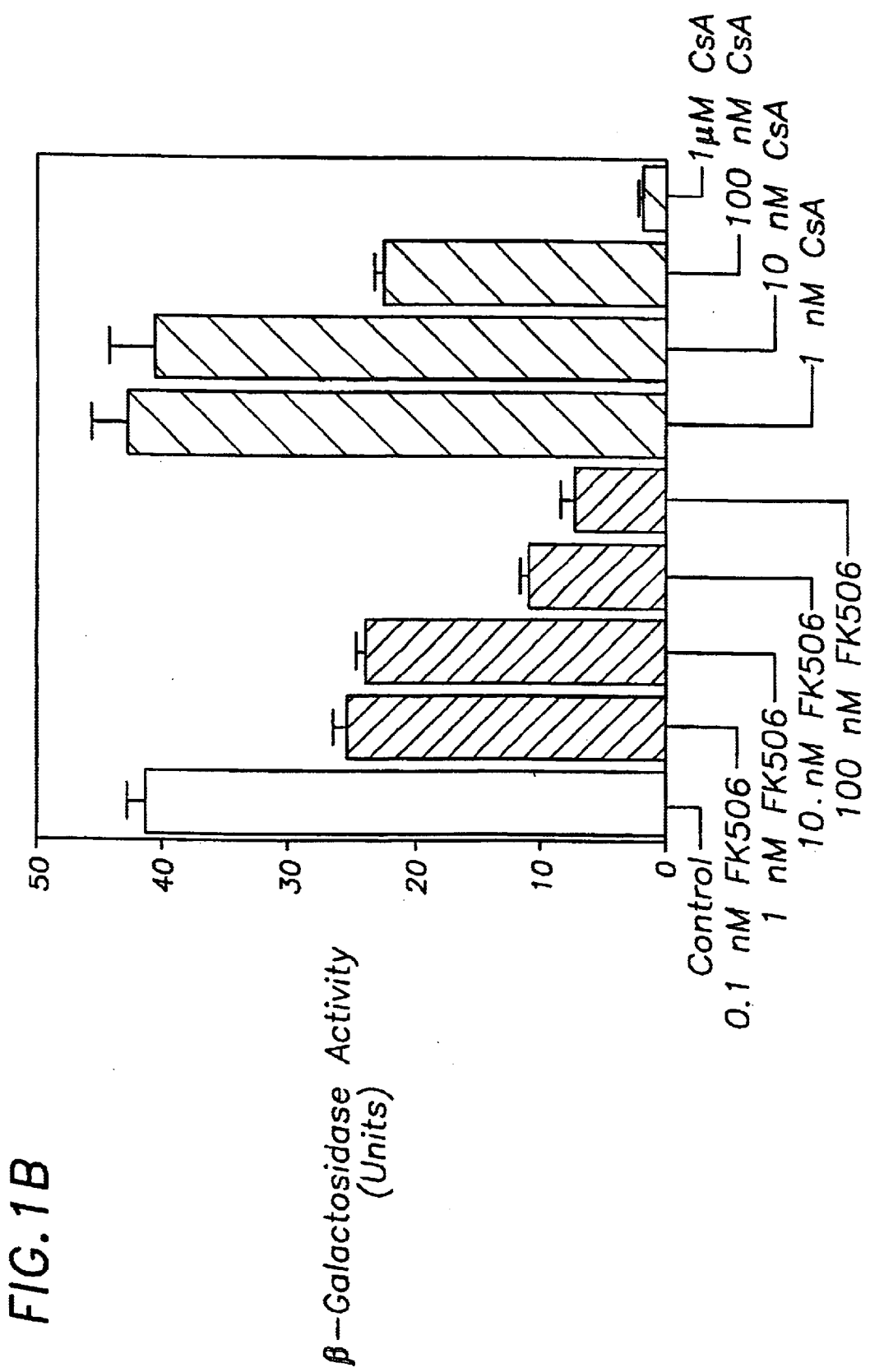
FIG. 1B is a graph depicting the sensitivity of interaction between Gal4-ΔCNβ2 (H160N) and Cabin 1–14 (SEQ ID NO: 5) to FK506 and CsA.
Figure 1C:
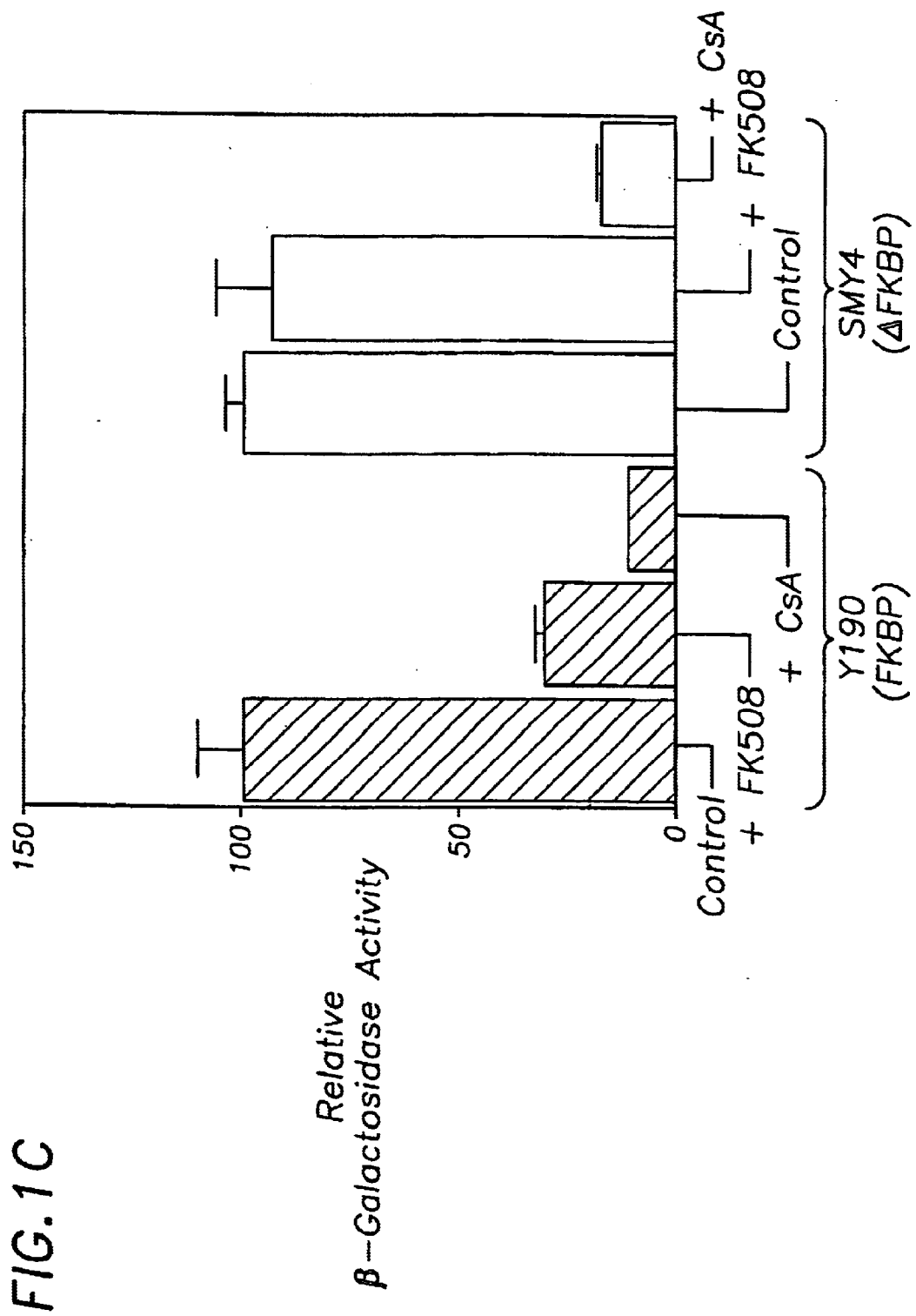
FIG. 1C is a graph depicting the sensitivity of interaction between Gal4-ΔCNβ2 (H160N) and Cabin 1–14 (SEQ ID NO: 5) to FK506 in the presence of endogenous FKBP12.

To determine the specificity of these clones for calcineurin, the yeast two-hybrid assay was performed in the presence of FK506 and CsA, which inhibit binding of substrates to calcineurin (Liu et al., Cell 66:807–815 (1991)). As shown in FIG. 1B, the interaction between one of the clones and the mutant calcineurin bait was inhibited by FK506 and CsA in a dose dependent manner. The remaining five clones exhibited similar sensitivity to FK506 and CsA. FK506 was found to be over 10-fold more potent than CsA, in agreement with the relative potencies of these drugs in T cells (Kino et al., J. Antibiotics 40:1249–1255 (1987)), indicating that the interactions were specific for calcineurin. To further assess the specificity of the interaction, the two-hybrid assay was performed in the yeast strain SMY4 that lacks FKBP12 (Cardenas et al., EMBO J. 13:5944–5957 (1994)). In SMY4, the interaction became resistant in FK506 while remaining sensitive to CsA, indicating that the sensitivity to FK506 is mediated by FKBP12 and is specific for calcineurin (See FIG. 1C).

Sequence analysis revealed that four of the six clones encoded overlapping cDNAs of the same gene (See FIG. 1D). The corresponding calcineurin binding protein was named Cabin 1.

Example 2

Cabin 1 is a Novel Nuclear Protein with Multiple Structural Motifs

This example illustrates the identification of the full-length human Cabin 1 cDNA and its putative translated polypeptide. Cabin 1 was shown to be a nuclear protein with multiple structural motifs.

The longest mouse Cabin 1 cDNA fragment obtained from the yeast two-hybrid screen was used to search a human EST database. Two overlapping cDNA fragments encoding human Cabin 1 were identified (obtained from Kazusa DNA Research Institute, Chiba, Japan, and Genome System Inc, Livermore, Calif., respectively). Using a combination of EST database searching and PCR cloning, the full-length human Cabin 1 was cloned to give a complete open reading frame encoding 2220 amino acids with a consensus Kozak initiation sequence preceded by stop codons. See FIG. 2A. Highlighted are: a putative coiled coil domain (bold); putative nuclear localization sequences (boxed and shaded) ("RKKR", KRKK", and "RLSRKRK"); PEST sequences (underlined); and a putative SH3 binding site (boxed). The N-termini of the four Cabin 1 clones isolated by the yeast two-hybrid screen 154, 6, 97 and 14, are highlighted. A database search revealed that Cabin 1 is a novel protein.

Amino acid analysis of the putative translated sequence revealed a leucine zipper, a putative SH3 binding site, and three putative nuclear localization sequences in Cabin 1 (See FIG. 2A). In addition, Cabin 1 contains several PEST sequences which have been proposed to target a wide variety of cellular proteins for degradation, including nuclear protein kinase C, IκBA, Fos, p53 and G1 cyclins (Rechsteiner and Rogers, Trends Biochem. Sci. 21:267–271 (1996)) (See FIG. 2A). There are also a number of consensus phosphorylation sites for various kinases including PKA, PKC, and MAP kinases.

Figure 2B:
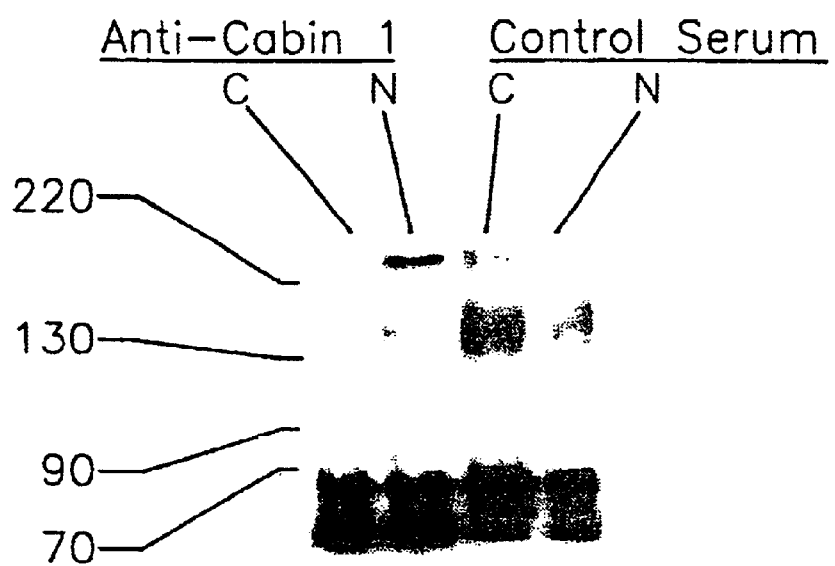
FIG. 2B is a Western blot showing that Cabin1 (SEQ ID NO: 1) is a nuclear protein.

Immunoprecipitation of Cabin 1 from fractionated cell lysates followed by Western blot using polyclonal anti-Cabin 1 antibodies confirmed that Cabin 1 was a nuclear protein (see FIG. 2B). Jurkat T cell lysates were fractionated into cytosolic (C) and nuclear (N) fractions and Cabin 1 was immunoprecipitated using anti-Cabin 1 antibodies. After SDS-PAGE, the immunoprecipitated Cabin 1 was blotted onto a nitrocellulose membrane and probed with anti-Cabin 1 antibodies or control serum.

In addition, Cabin 1 remained in the nucleus upon treatment of Jurkat T cells with PMA and ionomycin. Nuclear extract was prepared from Jurkat cells as previously described in Digman et al., Nuc. Acids Res. 11:1475–1489 (1983), with slight modifications. Exponentially growing Jurkat T cells were harvested and dounce homogenized in a homogenization buffer (20 mM Hepes, pH 7.9, 1.5 mM MgCl$_2$, 10 mM KCl, 0.5 mM EDTA and 1 mM PMSF). Nuclei were precipitated by centrifugation at 1,000×g for 10 min. (the supernatant was taken as the cytosolic fraction) washed twice and lysed in a lysis buffer (20 mM Hepes, pH 7.9, 0.1M NaCl, 1.5 mM MgCl$_2$ 10 mM KCl, 0.5 mM EDTA 1 mM PMSF, 1% Triton-X100, and 0.5% NP-400. Immunoprecipitation was carried out using both nuclear and cytosolic fractions with anti-Cabin 1 polyclonal antibodies. This was followed by immunoblotting with anit-Cabin 1 antibodies or a control serum.

Figure 2C:
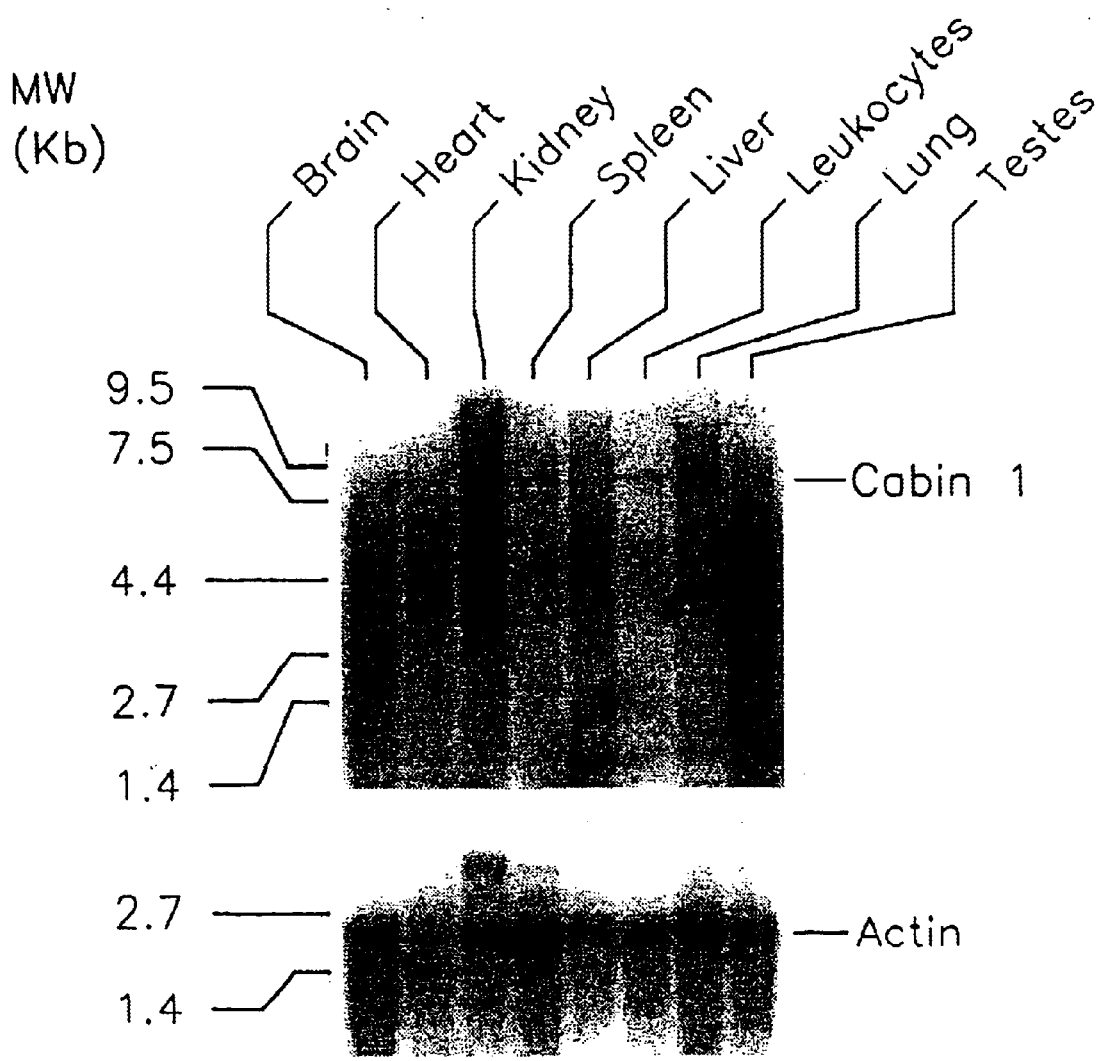
FIG. 2C is a Northern blot showing that mRNA encoding Cabin1 (SEQ ID NO: 1) is widely expressed in different tissues.

Northern analysis indicated that Cabin 1 was widely expressed in a variety of tissues including the spleen and leukocytes (See FIG. 2C). A 4-Kb fragment (EcoRI, BamHI) from the 5' region of mouse Cabin 1 cDNA was labeled with [$\alpha$-$^{32}$P] dCTP by random priming using the T7 Quick-Prime Kit (Pharmacia, Piscataway, N.J.) according to the manufacturer's instructions. Radiolabeled Cabin 1 fragment was purified through NucTrap Probe Purification column (Stratagene, La Jolla, Calif.) and used to probe a human multiple-tissue Northern blot (OriGene, Rockville, Md.). The membrane was hybridized at 42° C. for 20 hours, then washed at 65° in 2×SSC/0.1% SDS for 1 hour followed by another wash in 0.2×SSC/0.1% SDS for 30 min and a final wash in 0.1×SSC/0.1% SDS for 30 min.

Example 3

Interaction Between Cabin 1 and Calcineurin is Dependent on Both PKC and Calcineurin Signals This example illustrates that Cabin 1 interacts with calcineurin in T cells in a PKC- and calcium-dependent manner.

A mammalian two-hybrid system was established in Jurkat T cells by fusing calcineurin with the Gal4 DNA binding domain and Cabin 1–14 with the VP16 activation domain (Hsu et al., Proc. Natl. Acid Sci. USA 91:3181–3185 (1994)). The fusion plasmids for mammalian two-hybrid assays were constructed as follows: The cDNAs of calcineurin Aβ2 wild type and H160N mutant were fused to the GAL4 DB in the pM vector (obtained from Clontech, Palo Alto, Calif.) (pMCNβ2 and PMCNβ2 (H160N), and the cDNA of Cabin 1–14 was fused to the VP16 AD in the pVP16 vector (pVPCabin 1–14). Jurkat T cells were transfected with 5 μg of pMCβ2 or pMCβ2 (H160N), 5 μg of pVPCabin 1–14, 1 μg of pCMV-βGal, and 2 μg of pg5Luc, a luciferase reporter plasmid containing GAL4 promoter, by electroporation (960 μF, 250V). After 48 hr, cells were stimulated with 40 nM PMA and 2.5 μM ionomycin, either alone or in combination, for 6 hr before luciferase activity was measured for each sample. The luciferase reporter gene assay reagents were obtained from Promega, Madison, Wis., and the assay was performed per manufacturer's instructions. The transient transfection was performed using electroporation. 1×10$^7$ Jurkat cells were harvested, washed once in RPMI medium and mixed with 2 μg luciferase reporter plasmid and 0–5 μg expression plasmid for Cabin 1–14 in 300 μl RPMI in a sterile cuvette. An electric pulse (250 V, 960 mF) was applied (Bio-Rad Gene Pulser II, Hercules, Calif.). Where appropriate, the transfection efficiency was measured by co-transfecting 2 μg of CMV-driven β-galactosidase expression vector and measuring enzymatic β-galactosidase activity (Ausubel et al., Current Protocols in Molecular Biology (John Wiley & Sons, Inc., New York, 1994)). Where applied, FK506, rapamycin, cyclosporin A, and bisindolylmaleimide were added to Jurkat cells 30 min prior to the stimulation.

Figure 3A:
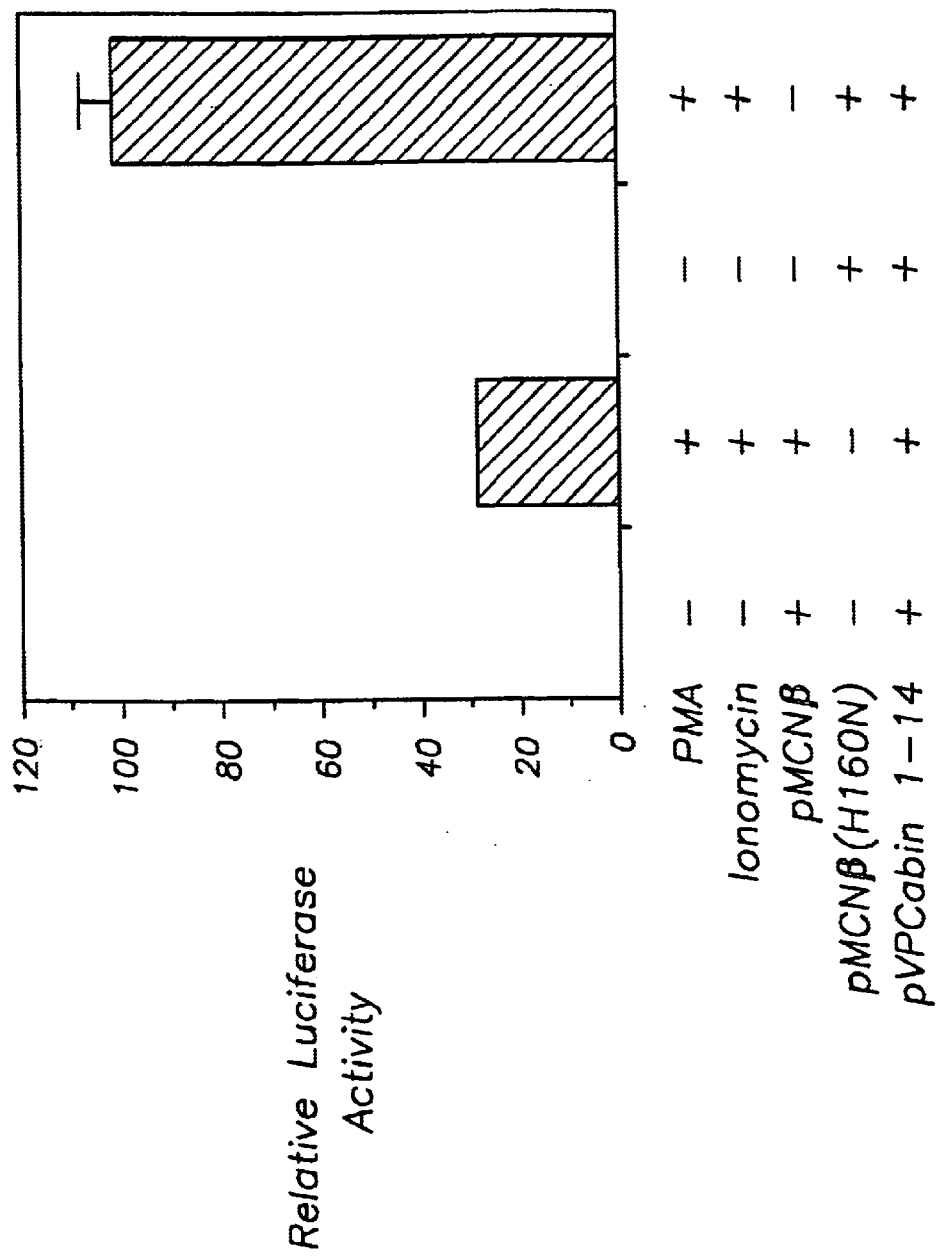
FIG. 3A is a graph showing that interaction between Cabin1–14 (SEQ ID NO: 5) and full length wild type of H160N calcineurin β2 in Jurkat T cells can be detected by a mammalian two-hybrid assay.
Figure 3B:
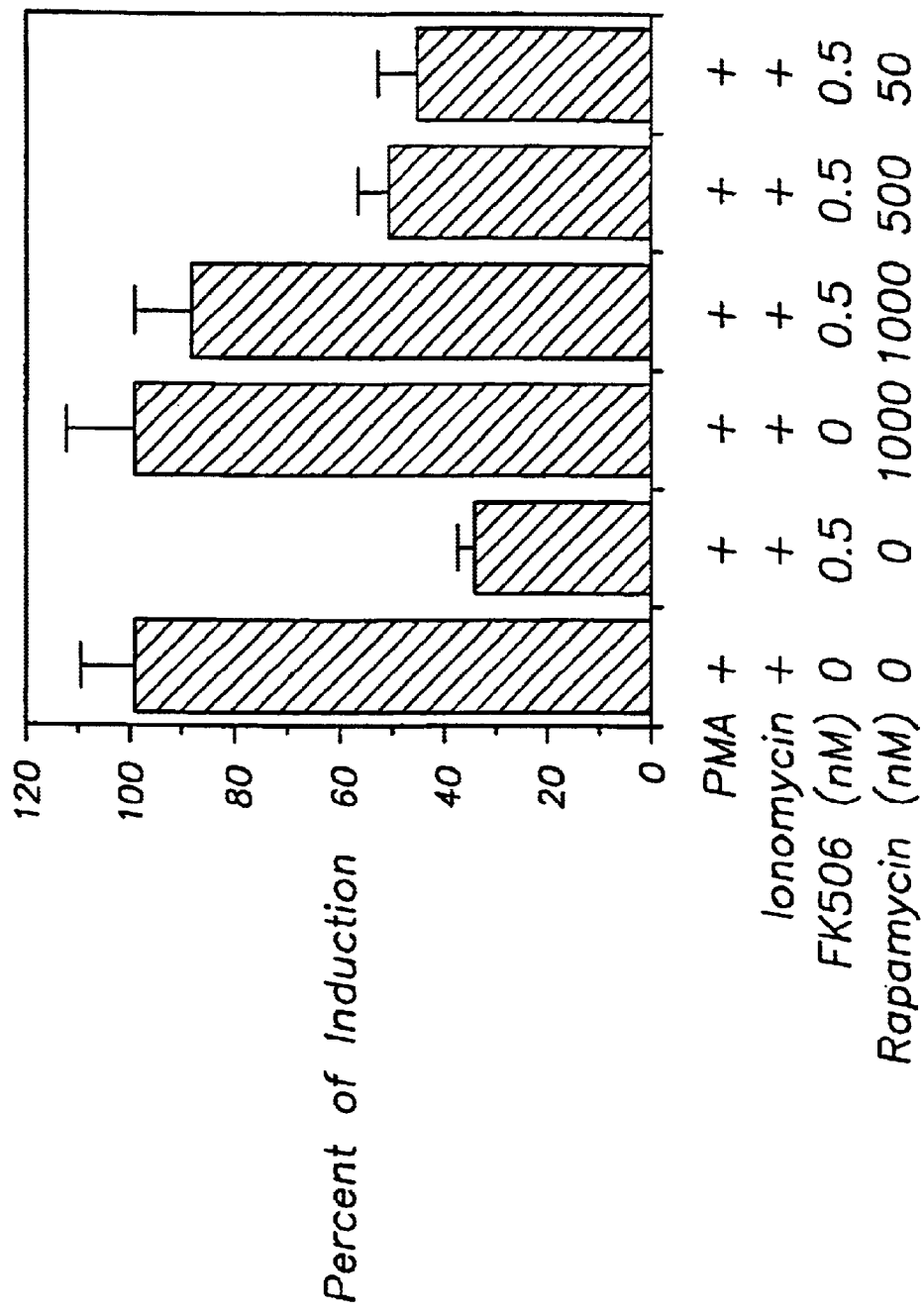
FIG. 3B is a graph showing that interaction between Cabin1–14 (SEQ ID NO: 5) and full length calcineurin β2 (H160N) is sensitive to FK506 and this inhibition is antagonized by an excess of rapamycin.

One advantage of this system is that it allows for the use of various forms of full length calcineurin that can be activated by calcium signal. When stimulated with PMA and ionomycin, the full length calcineurin β2 (H160N) mutant showed strong interaction with Cabin 1–14 (See FIG. 3A). While the wild type calcineurin also interacted with Cabin 1–14, the interaction is several fold weaker than that for the mutant enzyme. The alteration of the active site structure in the mutant appeared to have caused an increase in affinity of calcineurin for Cabin 1. Similar to the observation made in the yeast two-hybrid assay (See FIG. 1B), the interaction between the full length calcineurin β2 (H160N) mutant and Cabin 1–14 was sensitive to FK506 (See FIG. 3B) and CsA. Addition of rapamycin, an immunosuppressant that binds FKBP12 but does not inhibit TCR-mediated signaling or calcineurin (Sehgal et al., J. Antibiot. 28:727–742 (1975); Bierer et al. Proc. Natl. Acad. Sci. USA 87:9231–9235 (1990); Liu et al., Cell 66:807–815 (1991)), reverts the inhibitory effect of FK506 in a dose dependent manner, indicating that the interaction between Cabin 1 and calcineurin is highly specific (See FIG. 3B).

Figure 3C:
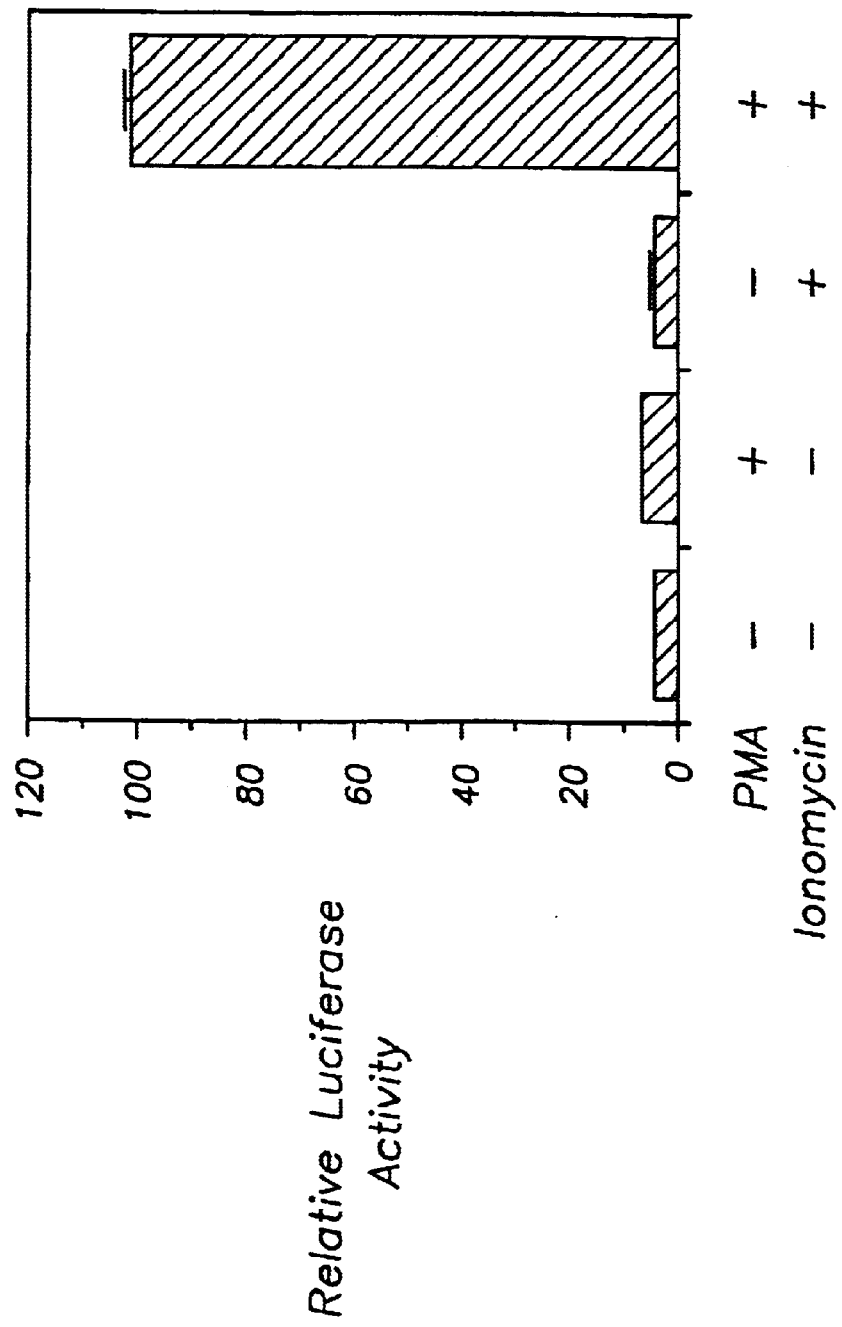
FIG. 3C is a graph showing that the interaction between Cabin1–14 (SEQ ID NO: 5) and full length calcineurin β2 (H160N) requires stimulation by both PMA and ionomycin in the mammalian two-hybrid assay.
Figure 3D:
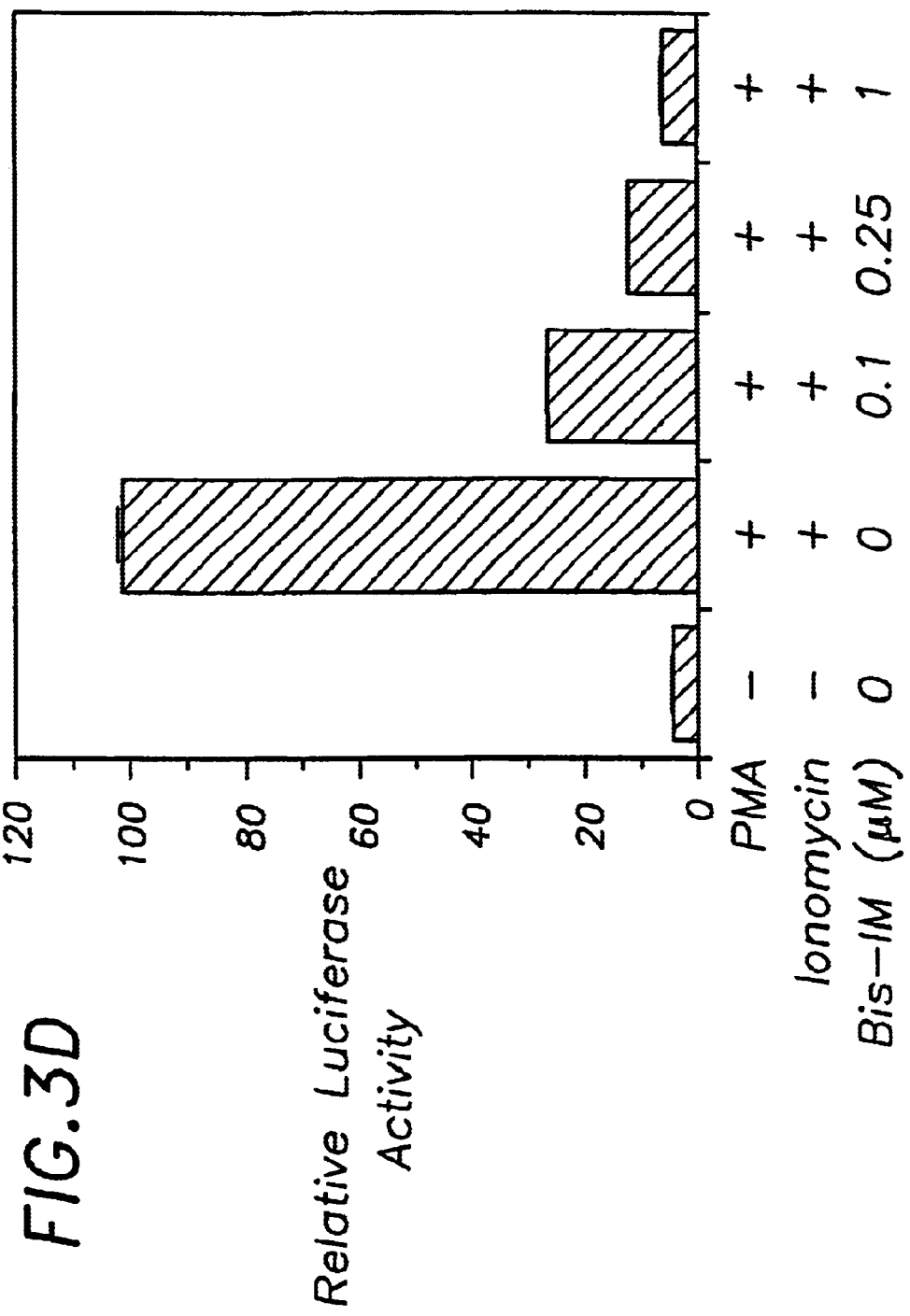
FIG. 3D is a graph showing that the interaction between Cabin1–14 (SEQ ID NO: 5) and full length calcineurin β2 (H160N) is sensitive to the PKC inhibitor bisindolylmaleimide.
Figure 3E:
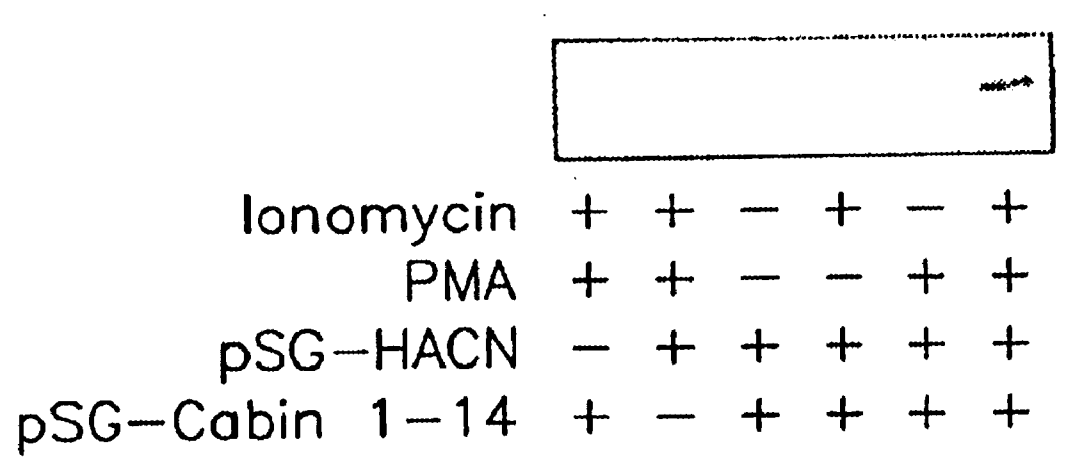

In the mammalian two-hybrid system, the interaction between full-length calcineurin and Cabin 1–14 required ionomycin, which is consistent with the activation of full-length calcineurin by calcium and calmodulin. Unexpectedly, this interaction also required PMA (see FIG. 3C). Since PMA is known to activate PKC, the effect of a PKC-specific inhibitor, bisindolylmaleimide (Toullec et a., J. Biol. Chem. 266:15771–15781 (1991)), was examined on the PMA/ionomycin-stimulated interaction between Cabin 1–14 and calcineurin. Bisidolylmaleimide inhibited the interaction between calcineurin and Cabin 1–14 in a dose-dependent manner, indicating that the requirement for PMA was mediated through PKC activation (See FIG. 3D). In addition to the mammalian two-hybrid system, the interaction of Cabin 1–14 and the wild type full-length calcineurin was also confirmed by co-immunoprecipitation (See FIG. 3E). In agreement with the observations made in the mammalian two-hybrid system, Cabin 1–14 and calcineurin coprecipitated only upon stimulation of Jurkat T cells with both PMA and ionomycin (See FIG. 3E). Jurkat T cells transfected with pSG-HACNAβ2 and pSG-Cabin 1–14 were stimulated with PMA, ionomycin or both for 3 hrs. The cells were lysed in a lysis buffer (20 mM TrisHCl, pH 7.4, 0.1M NaCl, 1% Triton X-100, 0.5% NP-40 and 0.5 mM PMSF). Cell lysates thus prepared were incubated with anti-Cabin 1 polyclonal antibodies and protein A/G agarose (Santa Cruz) for 2 hr., washed with lysis buffer and boiled in SDS sample buffer. The samples were subjected to 10% SDS-PAGE, transferred to nitrocellulose which was probed with anti-HA monoclonal antibodies and developed with ECL reagents (Amersham, Arlington Heights, Ill.). Cabin 1 interacted with calcineurin in T cells in a calcium and PKC-dependent manner.

Example 4

PKC Activation Leads to Hyperphosphorylation of Cabin 1

This example illustrates that activation of PKC induces hyperphosphorylation of Cabin 1–14.

Figure 4A:
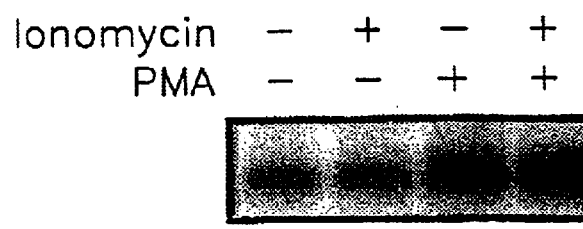
FIG. 4A is an autoradiogram showing $^{32}P$ labeling of Cabin1–14 (SEQ ID NO: 5) in the presence of PMA and ionomycin in Jurkat T cells.
Figure 4B:
FIG. 4B is a Western blot of transfected Cabin1–14 (SEQ ID NO: 5) in the presence or absence of PMA and ionomycin.

The dual requirement of Cabin 1-calcineurin interaction for calcium and PKC signals raised the question of whether PKC modulates this interaction by acting on calcineurin or Cabin 1. Calcineurin is not known to be subject to regulation by phosphorylation. The presence of multiple putative kinase phosphorylation sites in Cabin 1 suggested that Cabin 1 was subject to PKC-stimulated phosphorylation. To test this possibility and to determine whether the phosphorylation state of Cabin 1 was regulated during T cell activation, Jurkat T cells tranfected with an expression plasmid for Cabin 1–14 were labeled with $^{32}$P-inorganic phosphate in the presence of PMA, ionomycin or both. Cabin 1–14 was phosphorylated in unstimulated Jurkat T cells (see FIG. 4A). Treatment with PMA led to hyperphosphorylation of Cabin 1–14 as evidenced by a higher level of $^{32}$P incorporation and a shift in gel mobility. In contrast, the expression level of Cabin 1–14 was only slightly affected by PMA (see FIG. 4B). Treatment with ionomycin did not affect the phosphorylation state of Cabin 1–14, indicating that calcium-calcineurin signaling does not dephosphorylate Cabin 1–14. Consistent with these observations, immunoprecipitated Cabin 1–14 was not dephosphorylated by recombinant calcineurin in vitro. These results also indicated that the dependence of calcineurin-Cabin 1 interaction on PKC was likely mediated by the PKC-induced hyperphosphorylation of Cabin 1.

Example 5

Expression of Cabin 1 or Its C-terminal Fragments Blocks IL-2 Promoter Activation in Response to PMA and Ionomycin This example illustrates that the inhibitory effect of Cabin 1–14 upon T cell activation results from inhibition of calcineurin.

Figure 5A:
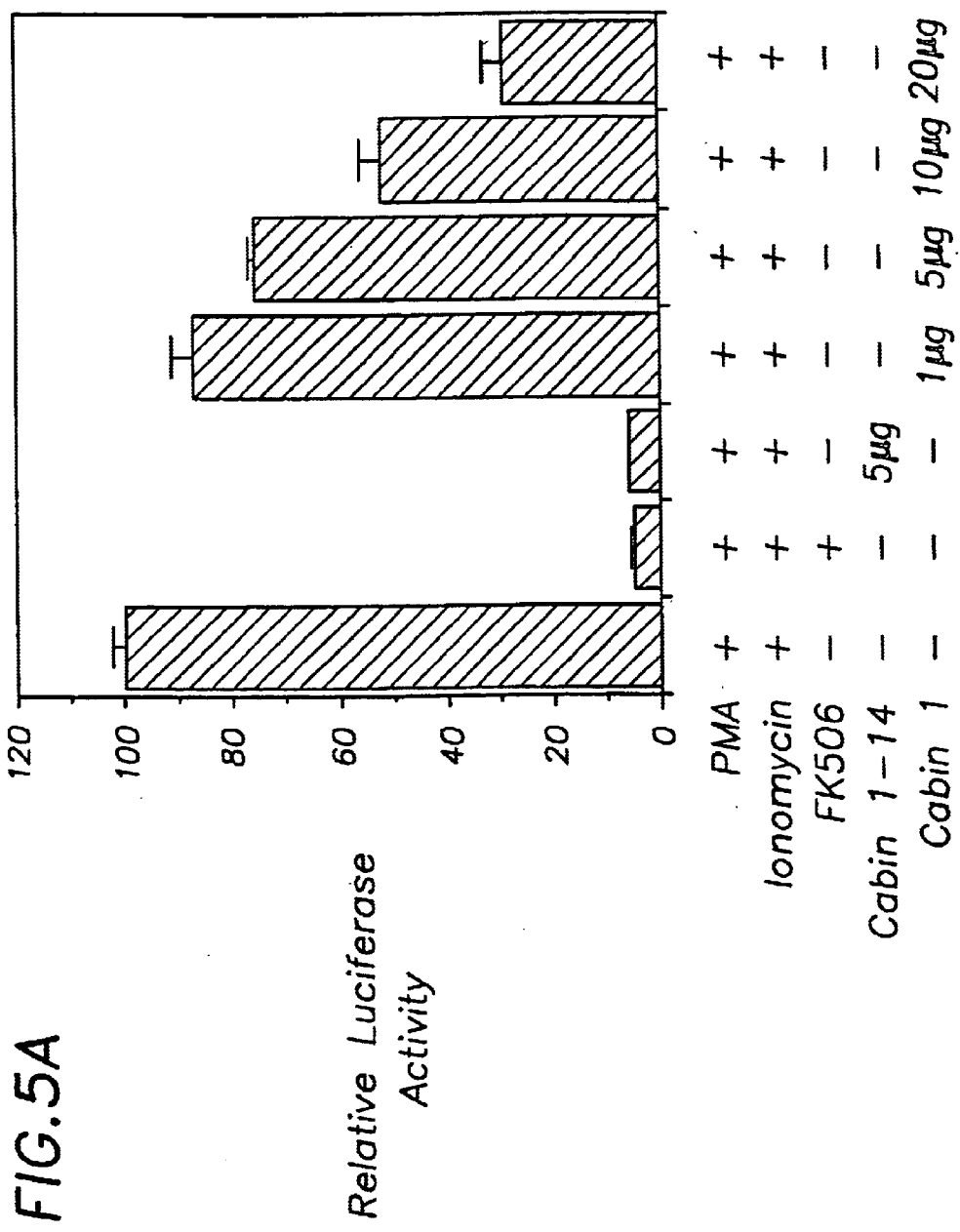
FIG. 5A is a graph showing that both Cabin1–14 (SEQ ID NO: 5) and Cabin1 (SEQ ID NO: 1) inhibit the activation of the IL-2/Luc reporter gene in response to PMA/ionomycin stimulation.

Given that Cabin 1 binds to calcineurin in T cells, it was determined whether expression of Cabin 1 or the C-terminal fragment of Cabin 1–14 affected calcineurin signaling upon T cell activation. Thus, Cabin 1–14 or the empty vector were cotransfected into Jurkat T cells with a luciferase reporter gene under the control of the IL-2 promoter. Upon treatment with PMA and ionomycin, the IL-2 reporter gene was activated (See FIG. 5A). This activation was inhibited by FK506, but was unaffected by cotransfection of the empty vector. Coexpression of Cabin 1–14, however, potently inhibited the activation of the IL-2 reporter gene (See FIG. 5A). Similar to Cabin 1–14, the full length Cabin 1 was also capable of inhibiting the IL-2 reporter gene activation, albeit with lower potency, indicating that inhibition of calcineurin signaling is an intrinsic activity of Cabin 1 (See FIG. 5A). Furthermore, as Cabin 1 is localized in the nucleus (See FIG. 2C), the inhibitory effect of full length Cabin 1 on the IL-2 reporter gene also implied that the presence of activated calcineurin in the nucleus was required for IL-2 reporter gene activation in response to PMA and ionomycin.

Figure 5B:
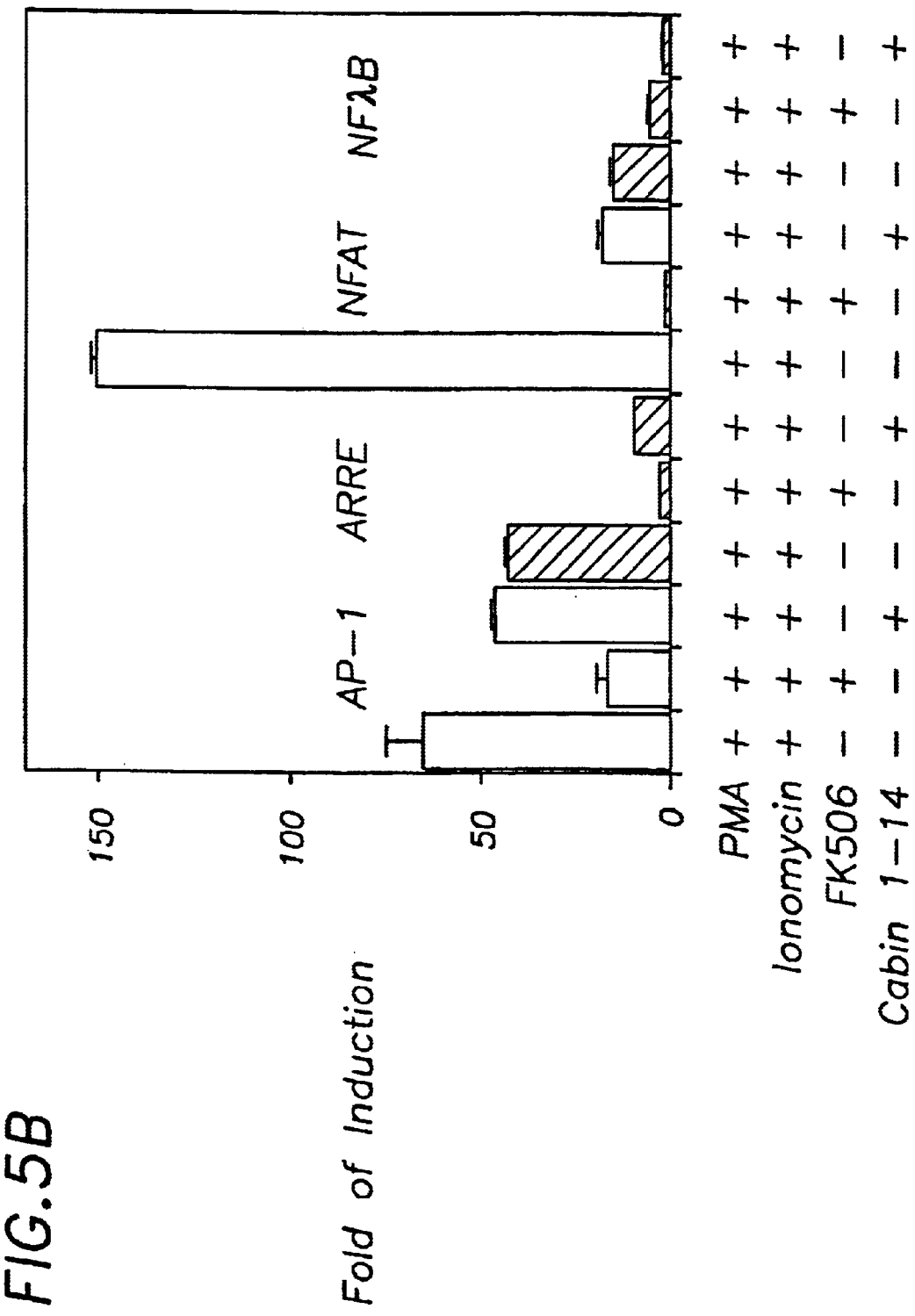
FIG. 5B is a graph showing that Cabin1–14 (SEQ ID NO: 5) inhibits the activation of AP/Luc, APRE/Luc, NF-AT/Luc and NF-κB/Luc reporter genes.

To further identify the specific elements in the IL-2 promoter that were sensitive to the inhibition by Cabin 1–14, reporter genes under the control of multimerized AP-1, ARRE (Oct1/AP-1), NF-AT, and NF-κB binding sites derived from the IL-2 promoter were tested (See FIG. 5B). All four reporter genes were inhibited by coexpression of Cabin 1–14, indicating that the inhibitory effect of Cabin 1–14 resulted from inhibiting of calcineurin since these reporters are known to be sensitive to FK506 and CsA.

Example 6

Cabin 1–14 Inhibits Dephosphorylation of NF-AT by Calcineurin In Vivo

This example illustrates that Cabin 1–14 directly inhibits the phosphatase activity of calcineurin in vivo.

To determine if the inhibition of IL-2 promoter by Cabin1–14 is mediated through the inhibition of calcineurin phosphatase activity in vivo, the effect of Cabin 1–14 on the calcineurin-mediated dephosphorylation of the N-terminal fragment of NF-ATI (ΔNF-AT1), upon treatment with ionomycin and PMA, was examined. Jurkat T cells were transfected with expression vectors for Cabin 1–14 (pSGCabin 1–14) and for HA-epitope tagged, truncated NF-AT1 (1–460) fused to green fluorescent protein (pSG-ΔNF-AT1 (1–460) by electroporation as described above. After 48 hrs, cells were treated with PMA and ionomycin, either alone or in combination, for another 1 hr. Whole-cell lysates were prepared and subjected to 8% SDS-polyacrylamide gel electrophoresis, transferred to nitrocellulose membrane (Schleicher & Schuell, New Hampshire), probed with anti-HA epitope monoclonal antibody, and developed with ECL reagents (Amersham, Arlington Heights, Ill.).

Figure 6:
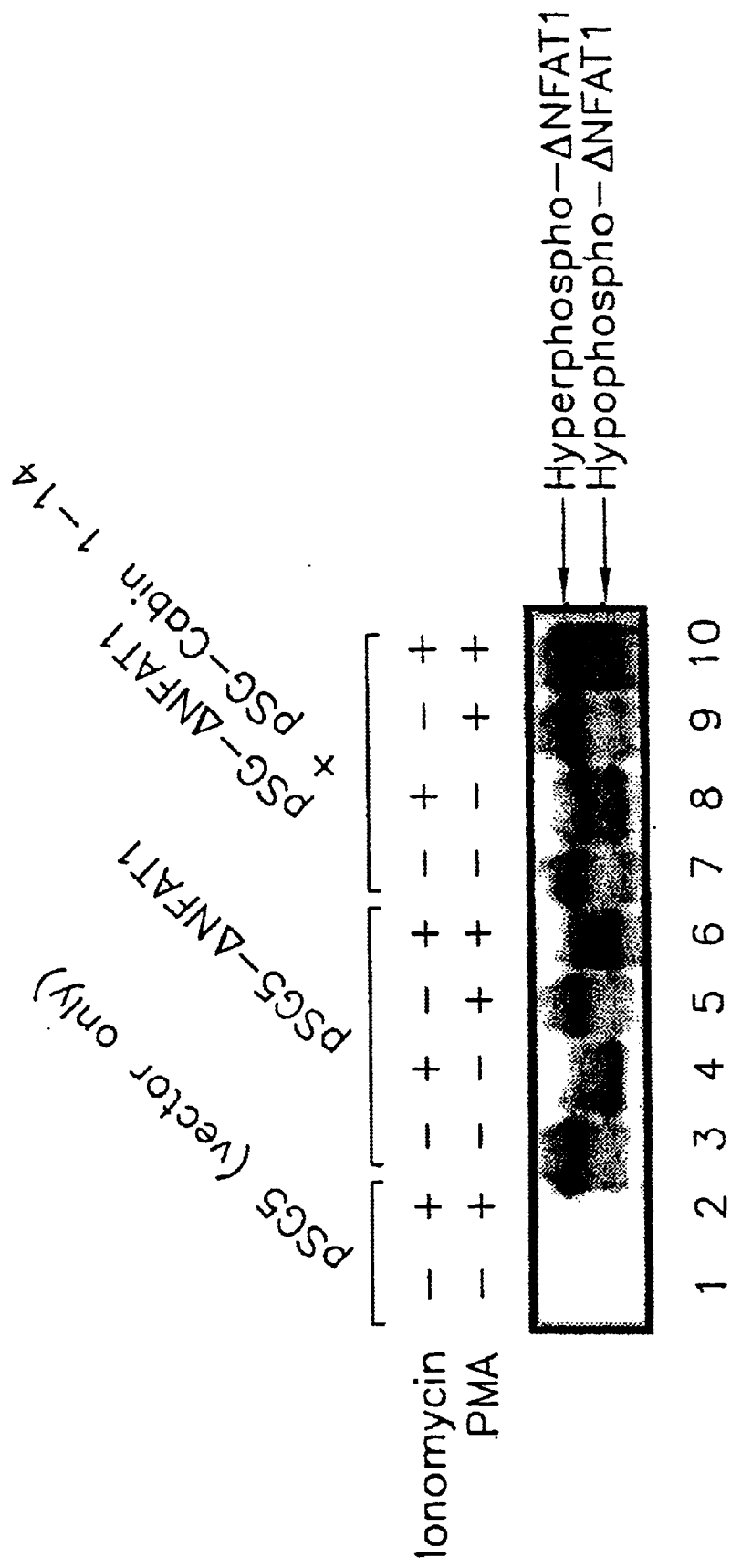
FIG. 6 is a graph of a Western blot showing that dephosphorylation of ΔNF-AT1 in response to ionomycin/PMA treatment is inhibited by Cabin1–14 (SEQ ID NO: 5).

Overexpression of Cabin 1–14 inhibited the dephosphorylation of ΔNF-AT 1 upon treatment with ionomycin in the presence or absence of PMA (See FIG. 6). It is noteworthly, however, that Cabin 1–14 inhibited ΔNF-AT1 dephosphorylation to a larger extent in the presence of PMA than in its absence (See FIG. 6, lane 8 versus 10). These observations were consistent with the PKC-dependence of the mammalian two-hybrid interaction between Cabin 1–14 and calcineurin (See FIG. 3D), and indicate that normally phosphorylated Cabin 1–14 can interact with calcineurin with low affinity, and that hyperphosphorylation of Cabin 1–14 upon PKC activation leads to higher affinity for calcineurin. They also support the conclusion that hyperphosphorylated Cabin 1–14 bind to, and inhibits the protein phosphatase activity of calcineurin in vivo.

Those skilled in the art will be able to ascertain using no more than routine experimentation, many equivalents of the specific embodiments of the invention described herein. These and all other equivalents are intended to be encompassed by the following claims.

What is claimed is:

1. An isolated polypeptide comprising the amino acid sequence as set forth in SEQ ID NO:1.

2. The polypeptide of claim 1 wherein said polypeptide is capable of binding to calcineurin.

3. The polypeptide of claim 2 wherein said calcineurin is activated calcineurin.

4. The polypeptide of claim 1 wherein said polypeptide is capable of inhibiting calcineurin function.

5. The polypeptide of claim 4 wherein said calcineurin function is protein phosphatase activity.

6. The polypeptide of claim 5 wherein said protein phosphatase activity is dephosphorylation of NF-AT.

7. The polypeptide of claim 1 wherein said polypeptide is capable of inhibiting transcriptional activation of calcineurin-responsive elements.

8. A polypeptide produced by a method comprising expressing a nucleic acid encoding the amino acid sequence as set forth in SEQ ID NO:1, and recovering said polypeptide.

9. A polypeptide produced by a method comprising expressing a nucleic acid encoding the amino acid sequence as set forth in SEQ ID NO:2, SEQ ID NO:3, SEQ ED NO:4, SEQ ID NO:5, SEQ ID NO:6 or SEQ ID NO:7.

* * * * *